United States Patent
Andrews et al.

(10) Patent No.: US 6,867,293 B2
(45) Date of Patent: *Mar. 15, 2005

(54) POLYNUCLEOTIDE CONSTRUCTS HAVING AT LEAST ONE TRANSCRIPTIONAL ENHANCER AND ENCODING A MODIFIED RICE EPSPS ENZYME

(75) Inventors: Christopher John Andrews, Bracknell (GB); Satvinder Bachoo, Bracknell (GB); Timothy Robert Hawkes, Bracknell (GB); Andrew Paul Pickerill, Bracknell (GB); Simon Anthony James Warner, Bracknell (GB)

(73) Assignee: Syngenta Limited, Guilford (GB)

( * ) Notice: Subject to any disclaimer, the term of this patent is extended or adjusted under 35 U.S.C. 154(b) by 95 days.

This patent is subject to a terminal disclaimer.

(21) Appl. No.: 10/012,070

(22) Filed: Oct. 29, 2001

(65) Prior Publication Data

US 2003/0077801 A1 Apr. 24, 2003

Related U.S. Application Data

(63) Continuation of application No. PCT/GB00/01573, filed on Apr. 20, 2000.
(51) Int. Cl.$^7$ .................. C12N 15/82; C12N 15/29; C12N 15/31
(52) U.S. Cl. .................. 536/23.6; 536/24.1; 536/24.2; 536/23.7; 536/23.72
(58) Field of Search .................. 536/23.2, 23.6, 536/24.1, 24.2, 23.7, 23.72; 800/300, 320.2, 278

(56) References Cited

FOREIGN PATENT DOCUMENTS

| | | |
|---|---|---|
| EP | 0459643 | 12/1991 |
| GB | 2326163 | 12/1998 |
| WO | WO 91/04323 | 4/1991 |
| WO | WO 92/06201 | 4/1992 |
| WO | WO 97/04103 | 2/1997 |
| WO | WO 97/20056 | 6/1997 |
| WO | WO 98/39419 | 9/1998 |
| WO | WO 98/44140 | 10/1998 |
| WO | WO 99/10513 | 3/1999 |
| WO | WO 00/66748 | 11/2000 |

OTHER PUBLICATIONS

1983 Genes, Benjamin Lewin editor, John Wiley & Sons, New York, ISBN 0-471-09316-5, pp. 191-192.*

Gasser, C.S. et al. *Structure, Expression, and Evolution of the 5-enolpyruvylshikimate-3phosphate synthase genes of petunia and tomato* Journal of Biological Chemistry, vol. 263(9) (Mar. 1988) pp. 4280-4287.

Accession No. AB016765, published Feb. 6, 1999, GenBank.

* cited by examiner

*Primary Examiner*—David H Kruse
(74) *Attorney, Agent, or Firm*—Syngenta Limited

(57) ABSTRACT

The invention is directed to polynucleotide constructs having at least one transcriptional enhancer operably liked to a rice EPSPS promoter and to a sequence encoding the rice EPSPS chloroplast transit peptide and rice EPSPS enzyme, the encoded enzyme having a modified region that confers herbicide resistance.

31 Claims, 15 Drawing Sheets

Figure 1:
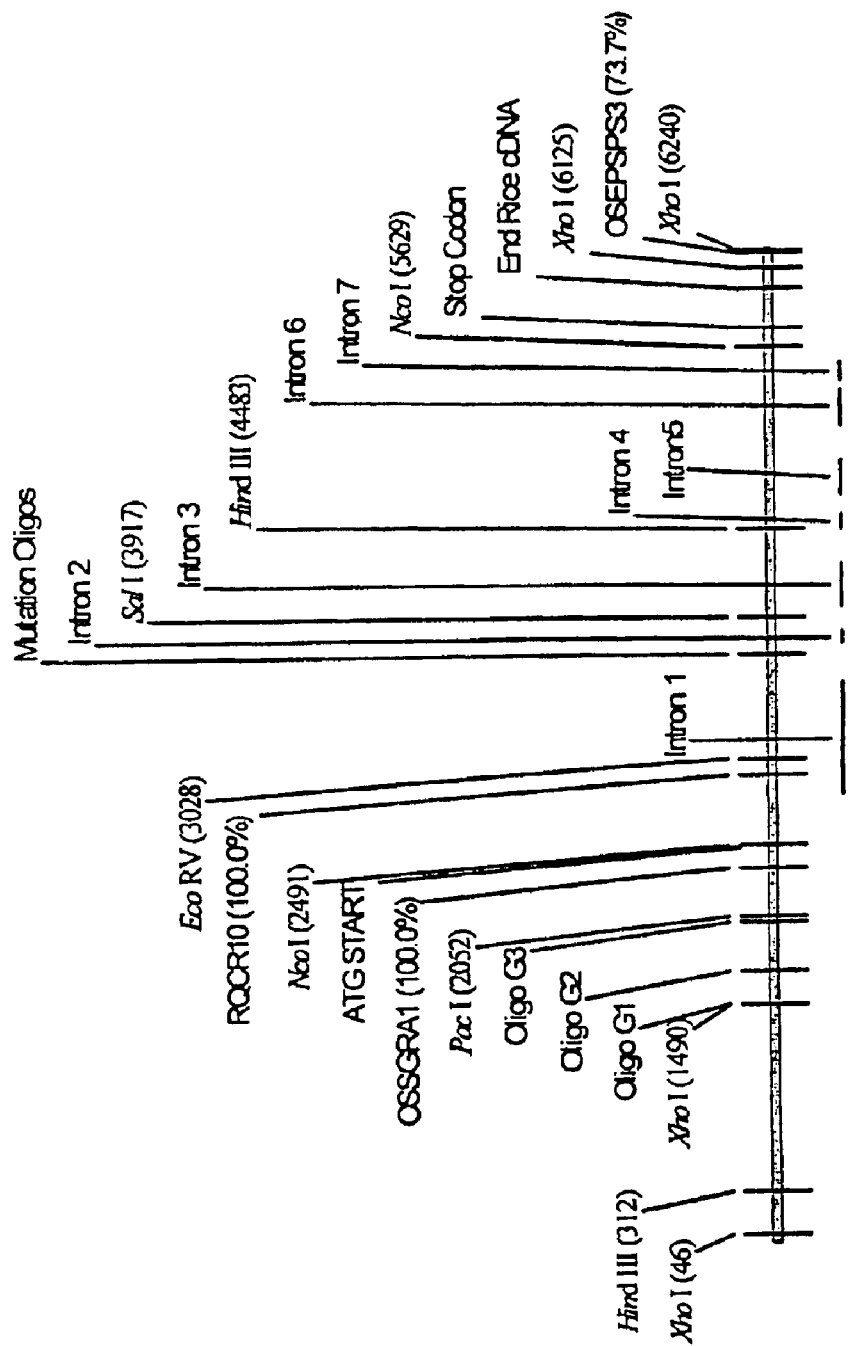

SEQUENCE LISTING

<160> NUMBER OF SEQ ID NOS: 57

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:primer
<221> NAME/KEY: misc_feature
<222> LOCATION: (1)..(32)
<223> OTHER INFORMATION: n is Inosine

<400> SEQUENCE: 1
gcacargcng caagngaraa ngccatngcc at        32

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:primer
<221> NAME/KEY: misc_feature
<222> LOCATION: (1)..(29)
<223> OTHER INFORMATION: n is Inosine

<400> SEQUENCE: 2
gcwggaacwg cmatgcgncc rytnacngc                                29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 3
atttcttctt cttcctccct tctccgcctc                               30

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 4
gagctccccg ggcgagtgtt gttgtgttct gtctaatg                      38

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 5
gcttacgaag gtatgatatc ctcctacatg tcaggc                        36

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 6
gcagtcacgg ctgctgtcaa tgatcgcatt gcaattccag cgttcc             46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 7
ggaacgctgg aattgcaatg cgatcattga cagcagccgt gactgc             46

<210> SEQ ID NO 8
<211> LENGTH: 55

```
<212> TYPE: DNA
<213> ORGANISM: Artificial Sequence
<220> FEATURE:
<223> OTHER INFORMATION: Description of Artificial Sequence:primer

<400> SEQUENCE: 8
ggtgggcatt cagtgccaag gaaacagtcg acatccgcac caagttgttt caacc        55

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 9
cgcctgcagc tcgaggttgg ttggtgagag tgagacacc                          39

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 10
cgcctgcagc tcgaggccac accaatccag ctggtgtgg                          39

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 11
gaacctcagt tatatctcat cg                                            22

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence:primer

<400> SEQUENCE: 12
cgctctagag gccggccaac atggtggagc acgacacact tgtctac                 47

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 13
cgctgcagct cgagcatcaa tccacttgct ttgaagacg                          39

<210> SEQ ID NO 14
<211> LENGTH:
<212> TYPE:
<213> ORGANISM:

<400> SEQUENCE: 14

000
```

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 15
cgctctagag gccggcccca aaatctccca tgaggagcac c                 41

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 16
cgctgcagct cgagccgcct ctccatccgg atgagg                      36

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence:primer

<400> SEQUENCE: 17
cgctctagag gccggccgaa tccgaaaagt ttctgcaccg ttttcacc         48

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 18
cgctgcagct cgaggctgtc ctccgttaga tcatcg                      36

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 19
gactagtggc cggccatcag cggccagctt ttgttc                      36

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 20
ttaactagtg aggaggccgc ctgccgtgc                              29

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 21
cgcctctaga ggccggccga tatccctcag ccgcctttca ctatc              45

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 22
cgctgcagtg ctcgcgatcc tcctcgcttt tcc                           33

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 23
ctgcagctcg agaacatggt ggagcacgac acacttgtct ac                 42

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 24
ttaattaaca tcaatccact tgctttgaag acg                           33

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 25
ctcgagggcc ggccgcagct ggcttg                                   26

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 26
ctcgagtttt gtggtcgtca ctgcgttcg                                29

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 27
ttaattaatt ttgtggtcgt cactgcgttc g                             31

<210> SEQ ID NO 28

```
<211> LENGTH: 66
<212> TYPE: DNA
<213> ORGANISM: Artificial Sequence
<220> FEATURE:
<223> OTHER INFORMATION: Description of Artificial Sequence:primer

<400> SEQUENCE: 28
cccatcctcc cgacctccac gccgccggca ggatcaagtg caaaggtccg ccttgtttct      60
cctctg                                                                66

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence:primer

<400> SEQUENCE: 29
gacgccatgg tcgccgccat ccgcagctgc acgggtccag gaaagcaatc                 50

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 30
cgagttctta tagtagattt caccttaatt aaaac                                 35

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 31
ggacccgtgc agctgcggta ccatggcggc gaccatggc                             39

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence:primer

<400> SEQUENCE: 32
gccatggtcg ccgccatggt accgcagctg cacgggtcc                             39

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 33
gcgctcgagt cagttcctga cgaaagtgct tagaacgtcg                            40

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:primer
```

```
<400> SEQUENCE: 34
gcgcatatga aggcggagga gatcgtgc                                    28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 35
gcgcatatga aggcggagga gatcgtgc                                    28

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 36
gcagtcacgg ctgctgtcaa tgatcgcatt gcaattccag cgttcc                46

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 37
gcgctcgagt cagttcctga cgaaagtgct tagaacgtcg                       40

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 38
ggaacgctgg aattgcaatg cgatcattga cagcagccgt gactgc                46

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 39
gtggaacgct ggaattgcaa tgcaat                                      26

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 40
gttgcatttc caccagcagc agt                                         23

<210> SEQ ID NO 41
```

<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 41
cccttcctct tgcgtgaatt ccatttc					27

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 42
gttgtgcccc taataaccag ag					22

<210> SEQ ID NO 43
<211> LENGTH: 3763
<212> TYPE: DNA
<213> ORGANISM: Oryza sp.

<400> SEQUENCE: 43

| | | | | | |
|---|---|---|---|---|---|
| atggcggcga | ccatggcgtc | caacgccgcg | gctgcggcgg | cggtgtccct | ggaccaggcc | 60 |
| gtggcggcgt | cggcggcgtt | ctcgtcgcgg | aagcagctgc | ggctgcccgc | cgcggcgcgc | 120 |
| ggggggatgc | gggtgcgggt | gcgggcgckg | ggcggcgggg | aggcggtggt | ggtggcgtcc | 180 |
| gcgtcgtcgt | cgtcggtggc | agcgccggcg | gcgaaggcgg | aggagatcgt | gctccagccc | 240 |
| atcagggaga | tctccggggc | ggttcagctg | ccagggtcca | agtcgctctc | caacaggatc | 300 |
| ctcctcctct | ccgccctctc | cgaggtgaga | cgcggatccc | ttcctcttgc | gtgaattcca | 360 |
| tttctggaga | tgagatttta | gggggtttat | taggtgaggt | ggctgtgttt | gtgaaatcct | 420 |
| aggaattatc | tctcaagtca | atctaacgat | gagatataac | tgaggttctg | gttttaatca | 480 |
| cacactcata | taaccaattt | attgaaacat | tttggtttgg | cataagaaac | tgcttacgaa | 540 |
| ggtatgatat | cctcctacat | gtcaggctac | taaattttca | cgacggtatg | atccactcaa | 600 |
| aacaagtttc | ttaacgagtc | tggtgaggtc | tgttatgaaa | tttgtgtaaa | ctaaggcaac | 660 |
| tttggaggtt | tcgcactgta | ccaatgttat | gtttgaacat | tttgcaagca | gtgctttctc | 720 |
| ccaaaattat | gcaattttga | ggctcctcta | catcattata | attccccaat | acattgctct | 780 |
| ttattcttaa | tagctttgat | cgcgaaattt | aacattttaa | ttcttgagct | gttattttgt | 840 |
| agcatcagtt | tatcatgagc | catgtttggt | actaaaatata | caatcccttg | ggtttatttg | 900 |
| tttccaagca | tgtcattaac | ttatcttaat | gtggacaaga | aactgatgcc | tgcttacatt | 960 |
| gctattattt | caagcgggta | ttgatccttt | gacatgtgat | tgatcatttt | tttttctctg | 1020 |
| gttattaggg | cacaacagtg | gtggacaact | tgctgaacag | tgaggatgtt | cactacatgc | 1080 |
| ttgaggccct | gaaagccctc | gggctctctg | tggaagcaga | taaagttgca | aaaagagctg | 1140 |
| tagtcgttgg | ctgtggtggc | aagtttcctg | ttgagaagga | tgcgaaagag | gaagtgcaac | 1200 |
| tcttcttggg | gaacgctgga | actgcaatgc | gaccattgac | agcagccgtg | actgctgctg | 1260 |
| gtggaaatgc | aacgtatgtt | ttttttttta | atgtttatga | aaatatgtat | ggaattcatg | 1320 |
| gggtatgttt | tatgaccttt | ttctttacca | tcagttatgt | gcttgatgga | gtgccacgaa | 1380 |
| tgagggagag | accgattggt | gacttggttg | tcggttgaa | acaacttggt | gcggatgtcg | 1440 |
| actgtttcct | tggcactgaa | tgcccacctg | ttcgtgtcaa | gggaattgga | ggacttcctg | 1500 |

-continued

```
gtggcaaggt tagttactcc taaactgcat cctttgtact tctgtatgca cctcaattct    1560
ttgtcaacct tctgcattta taaggaacat tctatgatgc aattcgacct tacactgcac    1620
agtaacttga aatgtttcat gcttaatcaa tatgccatat tcctgccaag ctcaagcgag    1680
caatatttgt ttgaatttgg taccatattt ttgtatattt gggcattcct ttttggtctt    1740
gatgtcttct tttgaattag catttaactg aattacactc aacaggttaa gctctctggt    1800
tccatcagca gtcagtactt gagtgccttg ctgatggctg ctcctttggc ccttggggat    1860
gtggagatcg aaatcattga caaactaatc tccattcctt acgttgaaat gacattgaga    1920
ttgatggagc gttttggtgt gaaggcagag cattctgata gttgggacag attctatatt    1980
aagggagggc agaagtacaa gtaagcttct acctgcctta ctgagctgaa ttattcgggt    2040
gtttatgatt aactccctaa actaaccctt tttcttttct ttggcattga cagatctcct    2100
ggaaatgcct atgttgaagg tgatgcctca agcgcgagct atttcttggc tggtgctgca    2160
atcactggag gcactgtgac agttcaaggt tgtggtacga ccagtttgca ggtataactg    2220
tagtgcctgt tttgacattc taccgtttag tcaagtttag tcagtagtca catattcaga    2280
atatagcaca atctgtatta tgccactgtt aatcaaatac gcttgaccta gagagtgcta    2340
tataccctag cttaatcttc aaactaaaca gttctcttgt ggcttgctgt gctgttatgt    2400
tccctgacct acatgttaat attacagggt gatgtcaaat ttgctgaggt acttgagatg    2460
atggagcaa aggttacatg gactgacacc agtgtaaccg taactggtcc accacgtgag    2520
ccttatggga agaaacacct gaaagctgtt gatgtcaaca tgaacaaaat gcctgatgtt    2580
gccatgaccc ttgccgttgt tgcactcttc gctgatggtc caactgctat cagagatggt    2640
aaacattaag gcctattata cctgttctat catactagca attactgctt agcattgtga    2700
caaaacaaat aaccaaactt tcttcaaaat aacttagaaa tataagaaag gttcgttttg    2760
tgtggtaaac agtactactg tagtttcagc tatgaagttt gctgctggca attttctgaa    2820
cggtttcagc taaattgcat gtttgttcat catacttatc cattgtcttc cacagtggct    2880
tcctggagag taaggaaac cgaaaggatg gttgcaattc ggaccgagct aacaaaggta    2940
aattcattag gtcccgtgtc ctttcattct tcaagtagtt tgttcataag ttgaattctc    3000
cttcaatgat gtttaaattc atcatcttct tttttggtgt tgtgccagct gggagcatcg    3060
gttgaagaag gtcctgacta ctgcatcatc accccaccgg agaagctgaa catcacggca    3120
atcgacacct acgatgatca caggatggcc atggccttct ccctcgctgc ctgcgccgac    3180
gtgcccgtga cgatcaggga ccctggttgc acccgcaaga ccttccccaa ctacttcgac    3240
gttctaagca ctttcgtcag gaactgaact gagcttttaa aagagtgagg tctaggttct    3300
gttgtctgtc tgtccatcat ccatgtgttg actgttgagg gaactcgttt cttcttttct    3360
tcacgagatg agttttgtg tgcctgtaat actagtttgt agcaaaggct gcgttacata    3420
aggtgatgag aattgaggta aaatgagatc tgtacactaa attcattcag actgttttgg    3480
cataaagaat aatttggcct tctgcgattt cagaagctat aaattgccat ctcactaaat    3540
tctccttggt cctcatggca atgcaacgac agtgtgaagc actgaagccc gtaatgctct    3600
atcaccacca tgtacgacag aaccatatat gtccatatgt acaactcgag tgttgtttga    3660
gtggccagca aactggctga ccaagccaca cgagagagaa tactataaac tcaatcatac    3720
ataacaagcc caagcaacat tagacagaac acaacaacac tcg                     3763
```

<210> SEQ ID NO 44

<211> LENGTH: 3763
<212> TYPE: DNA
<213> ORGANISM: Oryza sp.

<400> SEQUENCE: 44

| | | | | | |
|---|---|---|---|---|---|
| atggcggcga | ccatggcgtc | caacgccgcg | gctgcggcgg | cggtgtccct | ggaccaggcc    60 |
| gtggcggcgt | cggcggcgtt | ctcgtcgcgg | aagcagctgc | ggctgcccgc | cgcggcgcgc   120 |
| gggggatgc | gggtgcgggt | gcgggcgckg | ggcggcggg | aggcggtggt | ggtggcgtcc   180 |
| gcgtcgtcgt | cgtcggtggc | agcgccggcg | gcgaaggcgg | aggagatcgt | gctccagccc   240 |
| atcaggagga | tctccgggc | ggttcagctg | ccagggtcca | agtcgctctc | caacaggatc   300 |
| ctcctcctct | ccgccctctc | cgaggtgaga | cgcggatccc | ttcctcttgc | gtgaattcca   360 |
| tttctggaga | tgagatttta | ggggttat | taggtgaggt | ggctgtgttt | gtgaaatcct   420 |
| aggaattatc | tctcaagtca | atctaacgat | gagatataac | tgaggttctg | gttttaatca   480 |
| cacactcata | taaccaattt | attgaaacat | tttggtttgg | cataagaaac | tgcttacgaa   540 |
| ggtatgatat | cctcctacat | gtcaggctac | taaattttca | cgacggtatg | atccactcaa   600 |
| aacaagtttc | ttaacgagtc | tggtgaggtc | tgttatgaaa | tttgtgtaaa | ctaaggcaac   660 |
| tttggaggtt | tcgcactgta | ccaatgttat | gtttgaacat | tttgcaagca | gtgctttctc   720 |
| ccaaaattat | gcaattttga | ggctcctcta | catcattata | attccccaat | acattgctct   780 |
| ttattcttaa | tagctttgat | cgcgaaattt | aacatttaa | ttcttgagct | gttattttgt   840 |
| agcatcagtt | tatcatgagc | catgtttggt | actaaatata | caatcccttg | ggtttatttg   900 |
| tttccaagca | tgtcattaac | ttatcttaat | gtggacaaga | aactgatgcc | tgcttacatt   960 |
| gctattattt | caagcgggta | ttgatccttt | gacatgtgat | tgatcatttt | tttttctctg  1020 |
| gttattaggg | cacaacagtg | gtggacaact | tgctgaacag | tgaggatgtt | cactacatgc  1080 |
| ttgaggccct | gaaagccctc | gggctctctg | tggaagcaga | taaagttgca | aaaagagctg  1140 |
| tagtcgttgg | ctgtggtggc | aagtttcctg | ttgagaagga | tgcgaaagag | gaagtgcaac  1200 |
| tcttcttggg | gaacgctgga | attgcaatgc | gatcattgac | agcagccgtg | actgctgctg  1260 |
| gtggaaatgc | aacgtatgtt | ttttttttta | atgtttatga | aaatatgtat | ggaattcatg  1320 |
| gggtatgttt | tatgaccttt | ttcttttacca | tcagttatgt | gcttgatgga | gtgccacgaa  1380 |
| tgagggagag | accgattggt | gacttggttg | tcgggttgaa | acaacttggt | gcggatgtcg  1440 |
| actgtttcct | tggcactgaa | tgcccacctg | ttcgtgtcaa | gggaattgga | ggacttcctg  1500 |
| gtggcaaggt | tagttactcc | taaactgcat | cctttgtact | tctgtatgca | cctcaattct  1560 |
| ttgtcaacct | tctgcatttta | taaggaacat | tctatgatgc | aattcgacct | tacactgcac  1620 |
| agtaacttga | aatgtttcat | gcttaatcaa | tatgccatat | tcctgccaag | ctcaagcgag  1680 |
| caatatttgt | ttgaatttgg | taccatattt | ttgtatattt | gggcattcct | ttttggtctt  1740 |
| gatgtcttct | tttgaattag | catttaactg | aattacactc | aacaggttaa | gctctctggt  1800 |
| tccatcagca | gtcagtactt | gagtgccttg | ctgatggctg | ctcctttggc | ccttggggat  1860 |
| gtggagatcg | aaatcattga | caaactaatc | tccattcctt | acgttgaaat | gacattgaga  1920 |
| ttgatggagc | gttttggtgt | gaaggcagag | cattctgata | gttgggacag | attctatatt  1980 |
| aagggagggc | agaagtacaa | gtaagcttct | acctgcctta | ctgagctgaa | ttattcgggt  2040 |
| gtttatgatt | aactcccctaa | actaaccctt | tttcttttct | ttggcattga | cagatctcct  2100 |
| ggaaatgcct | atgttgaagg | tgatgcctca | agcgcgagct | atttcttggc | tggtgctgca  2160 |
| atcactggag | gcactgtgac | agttcaaggt | tgtggtacga | ccagtttgca | ggtataactg  2220 |

-continued

```
tagtgcctgt tttgacattc taccgtttag tcaagtttag tcagtagtca catattcaga    2280
atatagcaca atctgtatta tgccactgtt aatcaaatac gcttgaccta gagagtgcta    2340
tataccctag cttaatcttc aaactaaaca gttctcttgt ggcttgctgt gctgttatgt    2400
tccctgacct acatgttaat attacagggt gatgtcaaat ttgctgaggt acttgagatg    2460
atgggagcaa aggttacatg gactgacacc agtgtaaccg taactggtcc accacgtgag    2520
ccttatggga agaaacacct gaaagctgtt gatgtcaaca tgaacaaaat gcctgatgtt    2580
gccatgaccc ttgccgttgt tgcactcttc gctgatggtc aactgctat cagagatggt    2640 aaacattaag gcctattata cctgttctat catactagca attactgctt agcattgtga    2700
caaaacaaat aaccaaactt tcttcaaaat aacttagaaa tataagaaag gttcgttttg    2760
tgtggtaaac agtactactg tagtttcagc tatgaagttt gctgctggca atttttctgaa   2820 cggtttcagc taaattgcat gtttgttcat catacttatc cattgtcttc cacagtggct    2880
tcctggagag taaaggaaac cgaaaggatg gttgcaattc ggaccgagct aacaaaggta    2940
aattcattag gtcccgtgtc ctttcattct tcaagtagtt tgttcataag ttgaattctc    3000
cttcaatgat gtttaaattc atcatcttct tttttggtgt tgtgccagct gggagcatcg    3060
gttgaagaag gtcctgacta ctgcatcatc accccaccgg agaagctgaa catcacggca   3120
atcgacacct acgatgatca caggatggcc atggccttct ccctcgctgc ctgcgccgac    3180
gtgcccgtga cgatcaggga ccctggttgc acccgcaaga ccttccccaa ctacttcgac    3240
gttctaagca ctttcgtcag gaactgaact gagcttttaa aagagtgagg tctaggttct    3300
gttgtctgtc tgtccatcat ccatgtgttg actgttgagg gaactcgttt cttcttttct    3360
tcacgagatg agttttgtg tgcctgtaat actagtttgt agcaaaggct gcgttacata     3420
aggtgatgag aattgaggta aaatgagatc tgtacactaa attcattcag actgttttgg    3480
cataaagaat aatttggcct tctgcgattt cagaagctat aaattgccat ctcactaaat   3540
tctccttggt cctcatggca atgcaacgac agtgtgaagc actgaagccc gtaatgctct    3600
atcaccacca tgtacgacag aaccatatat gtccatatgt acaactcgag tgttgtttga    3660
gtggccagca aactggctga ccaagccaca cgagagagaa tactataaac tcaatcatac    3720
ataacaagcc caagcaacat tagacagaac acaacaacac tcg                     3763
```

```
<210> SEQ ID NO 45
<211> LENGTH: 217
<212> TYPE: DNA
<213> ORGANISM: Figwort mosaic virus

<400> SEQUENCE: 45
tctagaggcc ggccgcagct ggcttgtggg gaccagacaa aaaaggaatg gtgcagaatt    60
gttaggcgca cctaccaaaa gcatctttgc ctttattgca aagataaagc agattcctct    120
agtacaagtg gggaacaaaa taacgtggaa aagagctgtc ctgacagccc actcactaat    180
gcgtatgacg aacgcagtga cgaccacaaa actcgag                             217
```

```
<210> SEQ ID NO 46
<211> LENGTH: 323
<212> TYPE: DNA
<213> ORGANISM: Cauliflower mosaic virus

<400> SEQUENCE: 46
aacatggtgg agcacgacac acttgtctac tccaagaata tcaaagatac agtctcagaa    60
```

```
gaccagaggg ctattgagac ttttcaacaa aggtaatat cgggaaacct cctcggattc      120
cattgcccag ctatctgtca cttcatcgaa aggacagtag aaaaggaaga tggcttctac      180
aaatgccatc attgcgataa aggaaaggct atcgttcaag atgcctctac cgacagtggt      240
cccaaagatg gacccccacc cacgaggaac atcgtggaaa agaagacgt tccaaccacg       300 tcttcaaagc aagtggattg atg                                             323
```

<210> SEQ ID NO 47
<211> LENGTH: 309
<212> TYPE: DNA
<213> ORGANISM: Cauliflower mosaic virus

<400> SEQUENCE: 47

```
tgagactttt caacaaaggg taatatccgg aaacctcctc ggattccatt gcccagctat      60
ctgtcacttt attgtgaaga tagtggaaaa ggaaggtggc tcctacaaat gccatcattg      120
cgataaagga aaggccatcg ttgaagatgc ctctgccgac agtggtccca agatggacc       180 cccacccacg aggagcatcg tggaaaaaga agacgttcca accacgtctt caaagcaagt      240
ggattgatgt gatatctcca ctgacgtaag ggatgacgca caatcccact atccttcgca      300
agacccttc                                                             309
```

<210> SEQ ID NO 48
<211> LENGTH: 870
<212> TYPE: DNA
<213> ORGANISM: Zea mays

<400> SEQUENCE: 48

```
ttcagccttc gatgtggatg caacagcttc acaggattcc attaaatcgt agccattgtg      60
tcaaagtttg ctttgccaac gttatttatt tatttattta gaaaaccagc tttgaccagc      120
cgccctcttt acgtttggca caatttagct gaatccggcg gcatggcaag gtagactgca      180
gtgcagcgtg acccggtcgt gcccctctct agagataatg agcattgcat gtctaagtta      240
taaaaaatta ccacatattt ttttgtcaca cttgtttgaa gtgcagttta tctatcttta      300
tacatatatt taaactttac tctacgaata atataatcta tagtactaca ataatatcag      360
tgttttagag aatcatataa atgaacagtt agacatggtc taaaggacaa ttgagtattt      420
tgacaacagg actctacagt tttatctttt tagtgtgcat gtgttctcct ttttttttg       480 caaatagctt cacctatata atacttcatc cattttatta gtacatccat ttagggttta      540
gggttaatgg ttttatag actaattttt tagtacatct atttttattct attttagcct       600 ctaaattaag aaaactaaaa ctctatttta gtttttttat ttaataattt agatataaaa      660
tagaataaaa taaagtgact aaaaattaaa caaatacct ttaagaaatt aaaaaaacta       720
aggaaacatt tttcttgttt cgagtagata atgccagcct gttaaacgcc gtcgacgagt      780
ctaacggaca ccaaccagcg aaccagcagc gtcgcgtcgg gccaagcgaa gcagacggcg      840
cggcatctct gtcgctgcct ctggaccct                                       870
```

<210> SEQ ID NO 49
<211> LENGTH: 1501
<212> TYPE: DNA
<213> ORGANISM: Oryza sp.

<400> SEQUENCE: 49

```
gatatccctc agccgccttt cactatcttt tttgcccgag tcattgtcat gtgaaccttg      60
gcatgtataa tcggtgaatt gcgtcgattt tcctcttata ggtgggccaa tgaatccgtg     120
```

-continued

```
tgatcgcgtc tgattggcta gagatatgtt tcttccttgt tggatgtatt ttcatacata      180
atcatatgca tacaaatatt tcattacact ttatagaaat ggtcagtaat aaaccctatc      240
actatgtctg gtgtttcatt ttatttgctt ttaaacgaaa attgacttcc tgattcaata      300
tttaaggatc gtcaacggtg tgcagttact aaattctggt ttgtaggaac tatagtaaac      360
tattcaagtc ttcacttatt gtgcactcac ctctcgccac atcaccacag atgttattca      420
cgtcttaaat ttgaactaca catcatattg acacaatatt ttttttaaat aagcgattaa      480
aacctagcct ctatgtcaac aatggtgtac ataaccagcg aagtttaggg agtaaaaaac      540
atcgccttac acaaagttcg ctttaaaaaa taaagagtaa attttacttt ggaccaccct      600
tcaaccaatg tttcactttta gaacgagtaa tttattatt gtcactttgg accaccctca      660 aatcttttt ccatctacat ccaatttatc atgtcaaaga aatggtctac atacagctaa      720
ggagatttat cgacgaatag tagctagcat actcgaggtc attcatatgc ttgagaagag      780
agtcgggata gtccaaaata aaacaaaggt aagattacct ggtcaaaagt gaaaacatca      840
gttaaaaggt ggtataaagt aaaatatcgg taataaaagg tggcccaaag tgaaatttac      900
tcttttctac tattataaaa attgaggatg tttttgtcgg tactttgata cgtcatttt      960 gtatgaattg gttttaagt ttattcgctt tggaaatgc atatctgtat ttgagtcggg     1020
ttttaagttc gtttgctttt gtaaatacag agggatttgt ataagaaata tcttaaaaaa    1080
aacccatatg ctaatttgac ataatttttg agaaaaatat atattcaggc gaattctcac   1140
aatgaacaat aataagatta aaatagcttt cccccgttgc agcgcatggg tattttttct   1200
agtaaaaata aaagataaac ttagactcaa acatttaca aaaacaaccc ctaaagttcc     1260
taaagcccaa agtgctatcc acgatccata gcaagcccag cccaacccaa cccaacccaa   1320
cccaccccag tccagccaac tggacaatag tctccacacc ccccactat caccgtgagt     1380 tgtccgcacg caccgcacgt ctcgcagcca aaaaaaaaa aagaaagaaa aaaagaaaa     1440 agaaaaaaca gcaggtgggt ccgggtcgtg ggggccggaa acgcgaggag gatcgcgagc   1500
a                                                                   1501
```

<210> SEQ ID NO 50
<211> LENGTH: 898
<212> TYPE: DNA
<213> ORGANISM: Oryza sp.

<400> SEQUENCE: 50

```
gaatccgaaa agtttctgca ccgttttcac gttctaacta acaatatagg gaacgtgtgc       60
taaatataaa atgagacctt atatatgtag cgctgataac tagaactatg taagaaaaac     120
tcatccacct actttagtgg caatcgggct aaataaaaaa gagtcgctac actagtttcg     180
ttttccttag taattaagtg ggaaaatgaa atcattattg cttagaatat acgttcacat     240
ctctgtcatg aagttaaatt attcgaggta gccataattg tcatcaaact cttcttgaat     300
aaaaaaatct ttctagctga actcaatggg taaagagaga tattttttt aaaaaaatag     360 aatgaagata ttctgaacgt atcggcaaag atttaaacat ataattatat aatttttatag     420 tttgtgcatt cgttatatcg cacgtcatta aggacatgtc ttactccatc tcaatttta       480 tttagtaatt aaagacaatt gacttatttt tattatttat cttttttcga ttagatgcaa     540
ggtacttacg cacacacttt gtgctcatgt gcatgtgtga gtgcacctcc tcaatacacg     600
ttcaactagc gacacatctc taatatcact cgcctattta atacatttag gtagcaatat     660
```

```
ctgaattcaa gcactccacc atcaccagac cacttttaat aatatctaaa atacaaaaaa    720
taattttaca gaatagcatg aaaagtatga aacgaactat ttaggttttt cacatacaaa    780 aaaaaaaga attttgctcg tgcgcgagcg ccaatctccc atattgggca cacaggcaac    840
aacagagtgg ctgcccacag aacaacccac aaaaaacgat gatctaacgg aggacagc     898

<210> SEQ ID NO 51
<211> LENGTH: 754
<212> TYPE: DNA
<213> ORGANISM: Hordeum sp.
<220> FEATURE:
<221> NAME/KEY: misc_feature
<222> LOCATION: (1)..(754)
<223> OTHER INFORMATION: n = a, t, c or g

<400> SEQUENCE: 51
ccaaaatctc ccatgaggag cacctcaatg ccctcgggtg ccgtgtagat ttccacccga     60
cacatatttg ttactccttc cgtcacagtt tataaggcat gcacgtatac ctaggtcgtc    120
aatttgacca acttaatgag agacatatat tacaaaaaat atatcattaa aaacttttag    180
atgtactatt ttgtaatgat ataattttta tgttaaacaa tatatttnat ttaagttaag    240
ttgacgacct aggtacacgt gtacgcctta tnaactgtga cggagggagt attgtagtta    300
tgaataactt tttctataca ctttttttgtg ggggaacttt ttctataaac ttgaccacga    360
taataactgc aattttatc taaaacaata cttatgttgt tccttgtcac ggtaagatac    420
gtaccatggt taatgatgga ggtagtttca aaataaaat ctcaagttta atacacattt     480
atatactaga gttaatacaa agttaagaca attatgttga aacggaagaa gtatatatat    540
acaaagttaa tagaatgagt tggtacatac actatataaa tagtggagcg tggaggcgat    600
cgagtgaatg tatacgttgc agccgtggag aagacgagga ggggatcatg tgtttgtgga    660
ccatatatat tatgatgagg acatgcatgt ggagatatat atatatggat gggatgatat    720
tgggctacct cacctcatcc ggatggagag gcgg                                754

<210> SEQ ID NO 52
<211> LENGTH: 982
<212> TYPE: DNA
<213> ORGANISM: Oryza sp.

<400> SEQUENCE: 52
gttggttggt gagagtgaga caccgacgga acggaaggag aaccacgccg cttggatttt     60
tcttttttac cttttcaaat tttaatttaa aaaataaaac catttttaaaa acttatcttc    120 aaatacaaat ctttttaaaaa cactaacacg tgacacacag cgggcacgtc acccaaacgg    180
gcgtgacaat attgttttgc cacaccaatc cagctggtgt ggacaaaatg ttcatatatt    240
gaaaataaaa tttaaaacaa tttatatttt ttatctatat cattataaaa attgaagatg    300
tttttaccgg tattttgtta ctcatttgtg catgagtcgg ttttttaagtt tgttcgcttt    360 tggaaataca tatccgtatt tgagtatgtt tttaagttcg ttcgtttttt gaaatacaaa    420
aggaatcgta aaataaatct attttaaaaa actcgcatgc taacttgaga cgatcgaact    480
gctaattgca gctcataatt ttccaaaaaa aaatatatcc aaacgagttc ttatagtaga    540
tttcacctta attaaaacat ataaatgttc acccggtaca acgcacgagt attttttataa    600 gtaaaattaa agtttaaaa taaataaaaa tcccgccacc acggcgcgat ggtaaaaggg    660
ggacgcttct aaacgggccg ggcacgggac gatcggcccc gaacccggcc catctaaccg    720
ctgtaggccc accgcccacc aatccaactc cgtactacgt gaagcgctgg atccgcaacc    780
```

```
cgttaagcag tccacacgac tcgactcgac tcgcgcactc gccgtggtag gtggcaaccc      840
ttcttcctcc tctatttctt cttcttcctc ccttctccgc ctcaccacac caaccgcacc      900
aaccccaacc ccgcgcgcgc tctccctct ccctcccac caaccccacc ccatcctccc        960
gacctccacg ccgccggcaa tg                                                982

<210> SEQ ID NO 53
<211> LENGTH: 435
<212> TYPE: DNA
<213> ORGANISM: Oryza sp.

<400> SEQUENCE: 53
ttaattaaaa catataaatg ttcacccggt acaacgcacg agtattttta taagtaaaat       60
taaaagttta aaataaataa aaatcccgcc accacggcgc gatggtaaaa gggggacgct     120
tctaaacggg ccgggcacgg gacgatcggc ccgaacccg gcccatctaa ccgctgtagg      180
cccaccgccc accaatccaa ctccgtacta cgtgaagcgc tggatccgca acccgttaag    240
cagtccacac gactcgactc gactcgcgca ctcgccgtgg taggtggcaa cccttcttcc    300
tcctctattt cttcttcttc ctcccttctc cgcctcacca caccaaccgc accaaccccca   360 accccgcgcg cgctctcccc tctccctcc caccaacccc accccatcct cccgacctcc     420
acgccgccgg caatg                                                     435

<210> SEQ ID NO 54
<211> LENGTH: 1343
<212> TYPE: DNA
<213> ORGANISM: Oryza sp.

<400> SEQUENCE: 54
gccacaccaa tccagctggt gtggacaaaa tgttcatata ttgaaaataa aatttaaaac       60
aatttatatt ttttatctat atcattataa aaattgaaga tgttttttacc ggtattttgt    120 tactcatttg tgcatgagtc ggttttttaag tttgttcgct tttggaaata catatccgta    180
tttgagtatg tttttaagtt cgttcgtttt ttgaaataca aaaggaatcg taaaataaat    240
ctattttaaa aaactcgcat gctaacttga gacgatcgaa ctgctaattg cagctcataa    300
ttttccaaaa aaaatatat ccaaacgagt tcttatagta gatttcacct taattaaaac     360
atataaatgt tcacccggta caacgcacga gtatttttat aagtaaaatt aaaagtttaa   420
aataaataaa aatcccgcca ccacggcgcg atggtaaaag ggggacgctt ctaaacgggc    480
cgggcacggg acgatcggcc ccgaacccgg cccatctaac cgctgtaggc ccaccgccca    540
ccaatccaac tccgtactac gtgaagcgct ggatccgcaa cccgttaagc agtccacacg    600
actcgactcg actcgcgcac tcgccgtggt aggtggcaac ccttcttcct cctctatttc    660
ttcttcttcc tcccttctcc gcctcaccac accaaccgca ccaaccccaa ccccgcgcgc    720
gctctcccct ctccctccc accaaccccca ccccatcctc ccgacctcca cgccgccggc    780
aggatcaagt gcaaaggtcc gccttgtttc tcctctgtct cttgatctga ctaatcttgg    840
tttatgattc gttgagtaat tttggggaaa gctagcttcg tccacagttt tttttttcgat   900 gaacagtgcc gcagtggcgc tgatcttgta tgctatcctg caatcgtggt gaacttattt    960
cttttatatc cttcactccc atgaaaaggc tagtaatctt tctcgatgta acatcgtcca   1020
gcactgctat taccgtgtgg tccatccgac agtctggctg aacacatcat acgatattga  1080
gcaaagatct atcctcccctg ttctttaatg aaagacgtca ttttcatcag tatgatctaa  1140
```

```
gaatgttgca acttgcaagg aggcgtttct ttctttgaat ttaactaact cgttgagtgg    1200
ccctgtttct cggacgtaag gcctttgctg ctccacacat gtccattcga attttaccgt    1260
gtttagcaag agcgaaaagt ttgcatcttg atgatttagc ttgactatgc gattgctttc    1320
ctggacccgt gcagctgcgg atg                                           1343

<210> SEQ ID NO 55
<211> LENGTH: 538
<212> TYPE: DNA
<213> ORGANISM: Zea sp.
<220> FEATURE:
<223> OTHER INFORMATION: Description of Artificial Sequence:primer

<400> SEQUENCE: 55
gtccgccttg tttctcctct gtctcttgat ctgactaatc ttggtttatg attcgttgag     60
taattttggg gaaagctagc ttcgtccaca gttttttttt cgatgaacag tgccgcagtg    120
gcgctgatct tgtatgctat cctgcaatcg tggtgaactt atttcttta tatccttcac    180 tcccatgaaa aggctagtaa tctttctcga tgtaacatcg tccagcactg ctattaccgt    240
gtggtccatc cgacagtctg gctgaacaca tcatacgata ttgagcaaag atctatcctc    300
cctgttcttt aatgaaagac gtcattttca tcagtatgat ctaagaatgt tgcaacttgc    360
aaggaggcgt ttctttcttt gaatttaact aactcgttga gtggccctgt ttctcggacg    420
taaggccttt gctgctccac acatgtccat tcgaatttta ccgtgtttag caagagcgaa    480
aagtttgcat cttgatgatt tagcttgact atgcgattgc tttcctggac ccgtgcag     538

<210> SEQ ID NO 56
<211> LENGTH: 14
<212> TYPE: PRT
<213> ORGANISM: Oryza sp.

<400> SEQUENCE: 56

Gly Asn Ala Gly Thr Ala Met Arg Pro Leu Thr Ala Ala Val
1               5                   10

<210> SEQ ID NO 57
<211> LENGTH: 14
<212> TYPE: PRT
<213> ORGANISM: Oryza sp.

<400> SEQUENCE: 57

Gly Asn Ala Gly Ile Ala Met Arg Ser Leu Thr Ala Ala Val
1               5                   10
```

POLYNUCLEOTIDE CONSTRUCTS HAVING AT LEAST ONE TRANSCRIPTIONAL ENHANCER AND ENCODING A MODIFIED RICE EPSPS ENZYME

This application is a continuation of International Application No. PCT/GB00/01573, filed 20 Apr. 2000.

FIELD OF THE INVENTION

The present invention relates to recombinant DNA technology, and in particular to the production of transgenic plants which exhibit substantial resistance or substantial tolerance to herbicides when compared with non transgenic like plants. The invention also relates, inter alia, to the nucleotide sequences (and expression products thereof) which are used in the production of, or are produced by, the said transgenic plants.

BACKGROUND OF THE INVENTION

Plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agricultural community to kill weeds in the field in which crops are to be grown for commercial purposes.

It is particularly preferred that the plants are substantially resistant or substantially tolerant to herbicides (hereinafter "glyphosate") which have 5-enol pyruvyl shikimate phosphate synthetase (hereinafter "EPSPS") as their site of action, of which N-phosphonomethylglycine (and its various salts) is the pre-eminent example.

The herbicide may be applied either pre- or post emergence in accordance with usual techniques for herbicide application to fields comprising crops which have been rendered resistant to the herbicide. The present invention provides, inter alia, nucleotide sequences useful in the production of such herbicide tolerant or resistant plants.

DESCRIPTION OF THE INVENTION

According to the present invention there is provided an isolated polynucleotide comprising the sequence depicted in SEQ ID No. 43. The invention also provides a polynucleotide, excluding the cDNA encoding the rice and corn EPSPS, which encodes an EPSPS and which is complementary to one which when incubated at a temperature of between 65 and 70° C. in 0.1 strength citrate buffered saline containing 0.1% SDS followed by rinsing at the same temperature with 0.1 strength citrate buffered saline containing 0.1% SDS still hybridises with the sequence depicted in SEQ ID No. 43. An EPSPS encoding polynucleotide according to the invention may, however, be obtained by screening plant genomic DNA libraries with a nucleotide constituting an intron within the SEQ ID No. 43 sequence, and the invention also includes such a sequence obtainable from that screening.

The invention also includes an isolated polynucleotide comprising a region encoding a chloroplast transit peptide and a glyphosate resistant 5-enolpyruvylshikimate phosphate synthase (EPSPS) 3' of the peptide, the said region being under expression control of a plant operable promoter, with the provisos that the said promoter is not heterologous with respect to the said region, and the chloroplast transit peptide is not heterologous with respect to the said synthase.

By "heterologous" is meant from a different source, and correspondingly "non-heterologous" means derived from the same source—but at a gene rather than organism or tissue level. For example the CaMV35S promoter is clearly heterologous with respect to a petunia EPSPS coding sequence insofar as the promoter is derived from a virus and the sequence—the expression of which it controls—from a plant. The term "heterologous" according to the present invention has a still narrower meaning, however. For example "heterologous" as it relates to the present invention means that the petunia EPSPS coding sequence is "heterologous" with respect to, for example, a promoter also derived from petunia—other than that which controls expression of the EPSPS gene. In this sense the petunia promoter derived from the petunia EPSPS gene then used to control expression of an EPSPS coding sequence likewise-derived from petunia is "non-heterologous" with respect to the said coding sequence. "Non-heterologous" does not mean, however, that the promoter and coding sequence must necessarily have been obtained from one and the same (original or progenitor) polynucleotide. Likewise with respect to transit peptides. For example, a rubisco chloroplast transit peptide derived from sunflower is "heterologous" with respect to the coding sequence of an EPSPS gene likewise derived from sunflower (the same plant, tissue or cell). A rubisco transit peptide encoding sequence derived from sunflower is "non-heterologous" with respect to a rubisco enzyme encoding-sequence also derived from sunflower even if the origins of both sequences are different polynucleotides which may have been present in different cells, tissues or sunflower plants.

A preferred form of the polynucleotide comprises the following components in the 5' to 3' direction of transcription:

(i) At least one transcriptional enhancer being that enhancing region which is upstream from the transcriptional start of the sequence from which the enhancer is obtained and which enhancer per se does not function as a promoter either in the sequence in which it is endogenously comprised or when present heterologously as part of a construct;

(ii) The promoter from the rice EPSPS gene;

(iii) The rice genomic sequence which encodes the rice EPSPS chloroplast transit peptide;

(iv) The genomic sequence which encodes the rice EPSPS;

(v) A transcriptional terminator;

wherein the rice EPSPS coding sequence is modified in that a first position is mutated so that the residue at this position is Ile rather than Thr and a second position is mutated so that the residue at this position is Ser rather than Pro, the mutations being introduced into EPSPS sequences which comprise the following conserved region GNAGTAMRPLTAAV (SEQ ID NO:56) in the wild type enzyme such that modified sequence reads GNAGIAMRSLTAAV (SEQ ID NO:57).

The enhancing region preferably comprises a sequence the 3' end of which is at least 40 nucleotides upstream of the closest transcriptional start of the sequence from which the enhancer is obtained. In a further embodiment of the polynucleotide, the enhancing region comprises a region the 3' end of which is at least 60 nucleotides upstream of the said closest start, and in a still further embodiment of the polynucleotide the said enhancing region comprises a sequence the 3' of which is at least 10 nucleotides upstream from the first nucleotide of the TATA consensus of the sequence from which the enhancer is obtained.

The polynucleotide according to the invention may comprise two or more transcriptional enhancers, which in a particular embodiment of the polynucleotide may be tandemly present.

In the present inventive polynucleotide the 3' end of the enhancer, or first enhancer if there is more than one present, may be between about 100 to about 1000 nucleotides upstream of the codon corresponding to the translational start of the EPSPS transit peptide or the first nucleotide of an intron in the 5' untranslated region in the case that the said region contains an intron. In a more preferred embodiment of the polynucleotide, the 3' end of the enhancer, or first enhancer, is between about 150 to about 1000 nucleotides upstream of the codon corresponding to the translational start of the EPSPS transit peptide or the first nucleotide of an intron in the 5' untranslated region, and in a still more preferred embodiment the 3' end of the enhancer, or first enhancer, may be between about 300 to about 950 nucleotides upstream of the codon corresponding to the translational start of the EPSPS transit peptide or the first nucleotide of an intron in the 5' untranslated region. In a yet more preferred embodiment, the 3' end of the enhancer, or first enhancer, may be located between about 770 and about 790 nucleotides upstream of the codon corresponding to the translational start of the EPSPS transit peptide or the first nucleotide of an intron in the 5' untranslated region.

In an alternative inventive polynucleotide, the 3' end of the enhancer, or first enhancer, may be located between about 300 to about 380 nucleotides upstream of the codon corresponding to the translational start of the EPSPS transit peptide or the first nucleotide of an intron in the 5' untranslated region, and in a preferred embodiment of this alternative polynucleotide the 3' end of the enhancer, or first enhancer, is located between about 320 to about 350 nucleotides upstream of the codon corresponding to the translational start of the EPSPS transit peptide, or the first nucleotide of an intron in the 5' untranslated region.

In the polynucleotide according to the invention, the region upstream of the promoter from the rice EPSPS gene may comprise at least one enhancer derived from a sequence which is upstream from the transcriptional start of either the CaMV35S or FMV35S promoters.

Accordingly the polynucleotide may comprise in the 5' to 3' direction a first enhancer comprising a transcriptional enhancing region derived from a sequence which is upstream from the transcriptional start of the GOS 2 promoter and a second enhancer comprising a transcriptional enhancing region derived from a sequence which is upstream from the transcriptional start of either the CaMV35S or FMV35S promoters.

Alternatively, the polynucleotide may comprise in the 5' to 3' direction a first enhancer comprising a transcriptional enhancing region derived from a sequence which is upstream from the transcriptional start of the rice actin promoter and a second enhancer comprising a transcriptional enhancing region derived from a sequence which is upstream from the transcriptional start of either of the FMV35S or CaMV35S promoters.

Alternatively, the polynucleotide may comprise in the 5' to 3' direction a first enhancer comprising a transcriptional enhancing region derived from a sequence which is upstream from the transcriptional start of the barley plastocyanin promoter and a second enhancer comprising a transcriptional enhancing region derived from a sequence which is upstream from the transcriptional start of either the CaMV35S or FMV35S promoters.

Alternatively, the polynucleotide may comprise in the 5' to 3' direction a first enhancer comprising a transcriptional enhancing region derived from a sequence which is upstream from the transcriptional start of the maize polyubuitin promoter and a second enhancer comprising a transcriptional enhancing region derived from a sequence which is upstream from the transcriptional start of either the CaMV35S or FMV35S promoters.

Alternatively, the polynucleotide may comprise in the 5' to 3' direction a first enhancer comprising a transcriptional enhancing region derived from a sequence which is upstream from the transcriptional start of the FMV35S promoter and a second enhancer comprising a transcriptional enhancing region derived from a sequence which is upstream from the transcriptional start of the CaMV35S promoter.

Whatever the identity and juxtaposition of the various enhancers present in the polynucleotide, the nucleotides 5' of the codon which constitutes the translational start of the rice EPSPS chloroplast transit peptide may be Kozack preferred. What is meant by this is well known to the skilled man and will be further apparent from the examples below.

Particularly preferred embodiments of the present inventive polynucleotide have a non-translated region which comprises a sequence which functions as an intron located 5' of the rice genomic sequence which encodes the rice EPSPS chloroplast transit peptide. The non-translated region may comprise the sequence depicted in SEQ ID No. 55. In particular, the non-translated region may comprise the maize ADHI intron which has the sequence of SEQ ID No. 55.

The polynucleotide of the invention may comprise a virally derived translational enhancer located within the non translated region 5' of the rice genonic sequence which encodes the rice EPSPS chloroplast transit peptide. The man skilled in the art is aware of the identity of such suitable translational enhancers—such as the Omega and Omega prime sequences derived from TMV and that derived from the tobacco etch virus, and how such translational enhancers can be introduced into the polynucleotide so as to provide for the desired result.

The polynucleotide according to the invention may further comprise regions encoding proteins capable of conferring upon plant material containing it at least one of the following agronomically desirable traits: resistance to insects, fungi, viruses, bacteria, nematodes, stress, dessication, and herbicides. Whilst such a polynucleotide contemplates the herbicide resistance conferring gene being other than an EPSPS, such as glyphosate oxido-reductase (GOX) for example, the herbicide may be other than glyphosate in which case the resistance conferring genes may be selected from the group encoding the following proteins: phosphinothricin acetyl transferase (PAT), hydroxyphenyl pyruvate dioxygenase (HPPD), glutathione S transferase (GST), cytochrome P450, Acetyl-COA carboxylase (ACCase), Acetolactate synthase (ALS), protoporphyrinogen oxidase (PPO), dihydropteroate synthase, polyamine transport proteins, superoxide dismutase (SOD), bromoxynil nitrilase, phytoene desaturase (PDS), the product of the tfdA gene obtainable from *Alcaligenes eutrophus*, and known mutagenised or otherwise modified variants of the said proteins. In the case that the polynucleotide provides for multiple herbicide resistance such herbicides may be selected from the group consisting of a dinitroaniline herbicide, triazolo-pyrimidines, uracil, a phenylurea, triketone, isoxazole, acetanilide, oxadiazole, triazinone, sulfonanilide, amide, anilide, RP201772, flurochloridone, norflurazon, and triazolinone type herbicide and the post-emergence herbicide is selected from the group consisting of glyphosate and salts thereof, glufosinate, asulam, bentazon, bialaphos, bromacil, sethoxydim or another cyclohexanedione, dicamba, fosamine, flupoxam, phenoxy propionate, quizalofop or another aryloxy-phenoxypropanoate, picloram, fluormetron, atrazine or another triazine, metribuzin, chlorimuron, chlorsulfuron, flumetsulam, halosulfuron, sulfometron, imazaquin, imazethapyr, isoxaben, imazamox, metosulam, pyrithrobac, rimsulfuron, bensulfuron, nicosulfuron, fomesafen, fluroglycofen, KIH9201, ET751, carfentrazone, ZA1296, sulcotrione, paraquat, diquat, bromoxynil and fenoxaprop.

In the case that the polynucleotide comprises sequences encoding insecticidal proteins, these proteins may be selected from the group consisting of crystal toxins derived from Bt, including secreted Bt toxins; protease inhibitors, lectins, Xenhorabdus/Photorhabdus toxins; the fungus resistance conferring genes may be selected from the group consisting of those encoding known AFPs, defensins, chitinases, glucanases, Avr-Cf9. Particularly preferred insecticidal proteins are cryIAc, cryIAb, cry3A, Vip 1A, Vip 1B, cystein protease inhibitors, and snowdrop lectin. In the case that the polynucleotide comprises bacterial resistance conferring genes these may be selected from the group consisting of those encoding cecropins and techyplesin and analogues thereof. Virus resistance conferring genes may be selected from the group consisting of those encoding virus coat proteins, movement proteins, viral replicases, and antisense and ribozyme sequences which are known to provide for virus resistance; whereas the stress, salt, and drought resistance conferring genes may be selected from those that encode Glutathione-S-transferase and peroxidase, the sequence which constitutes the known CBF1 regulatory sequence and genes which are known to provide for accumulation of trehalose.

The polynucleotide according to the invention may be modified to enhance expression of the protein encoding sequences comprised by it, in that mRNA instability motifs and/or fortuitous splice regions may be removed, or crop preferred codons may be used so that expression of the thus modified polynucleotide in a plant yields substantially similar protein having a substantially similar activity/function to that obtained by expression of the unmodified polynucleotide in the organism in which the protein encoding regions of the unmodified polynucleotide are endogenous. The degree of identity between the modified polynucleotide and a polynucleotide endogenously contained within the said plant and encoding substantially the same protein may be such as to prevent co-suppression between the modified and endogenous sequences. In this case the degree of identity between the sequences should preferably be less than about 70%.

The invention still further includes a biological or transformation vector comprising the present inventive polynucleotide. Accordingly, by "vector" is meant, inter alia, one of the following: a plasmid, virus, cosmid or a bacterium transformed or transfected so as to contain the polynucleotide.

The invention still further includes plant material which has been transformed with the said polynucleotide or vector, as well as such transformed plant material which has been, or is, further transformed with a polynucleotide comprising regions encoding proteins capable of conferring upon plant material containing it at least one of the following agronomically desirable traits: resistance to insects, fungi, viruses, bacteria, nematodes, stress, dessication, and herbicides.

The invention still further includes morphologically normal, fertile whole plants which have been regenerated from the material disclosed in the immediately preceding paragraph, their progeny seeds and parts, which progeny comprises the polynucleotide or vector of the invention stably incorporated into its genome and heritable in a Mendelian manner.

The invention still further includes morphologically normal fertile whole plants which contain the present inventive polynucleotide and which result from the crossing of plants which have been regenerated from material transformed with the present inventive polynucleotide or vector, and plants which have been transformed with a polynucleotide comprising regions encoding proteins capable of conferring upon plant material containing it at least one of the following agronomically desirable traits: resistance to insects, fungi, viruses, bacteria, nematodes, stress, dessication, and herbicides, the progeny of the resultant plants, their seeds and parts.

Plants of the invention may be selected from the group consisting of field crops, fruits and vegetables such as canola, sunflower, tobacco, sugar beet, cotton, maize, wheat, barley, rice, sorghum, tomato, mango, peach, apple, pear, strawberry, banana, melon, potato, carrot, lettuce, cabbage, onion, soya spp, sugar cane, pea, field beans, poplar, grape, citrus, alfalfa, rye, oats, turf and forage grasses, flax and oilseed rape, and nut producing plants insofar as they are not already specifically mentioned, their progeny, seeds and parts.

Particularly preferred such plants include maize, soybean, cotton, sugar beet and canola.

The invention still further comprises a method of selectively controlling weeds in a field, the field comprising weeds and plants of the invention or the herbicide resistant progeny thereof, the method comprising application to the field of a glyphosate type herbicide in an amount sufficient to control the weeds without substantially affecting the plants. According to this method, one or more of a herbicide, insecticide, fungicide, nematicide, bacteriocide and an antiviral may be applied to the field (and thus the plants contained within it) either before or after application of the glyphosate herbicide.

The invention still further provides a method of producing plants which are substantially tolerant or substantially resistant to glyphosate herbicide, comprising the steps of:

(i) transforming plant material with the polynucleotide or vector of the invention;

(ii) selecting the thus transformed material; and (iii) regenerating the thus selected material into morphologically normal fertile whole plants.

The transformation may involve the introduction of the polynucleotide into the material by any known means, but in particular by: (i) biolistic bombardment of the material with particles coated with the polynucleotide; (ii) by impalement of the material on silicon carbide fibres which are coated with a solution comprising the polynucleotide; or (iii) by introduction of the polynucleotide or vector into *Agrobacterium* and co-cultivation of the thus transformed *Agrobacterium* with plant material which is thereby transformed and is subsequently regenerated. Plant transformation, selection and regeneration techniques, which may require routine modification in respect of a particular plant species, are well known to the skilled man. The thus transformed plant material may be selected by its resistance to glyphosate.

The invention still further provides the use of the present inventive polynucleotide or vector in the production of plant tissues and/or morphologically normal fertile whole plants which are substantially tolerant or substantially resistant to glyphosate herbicide.

The invention still further includes a method of selecting biological material transformed so as to express a gene of interest, wherein the transformed material comprises the polynucleotide or vector of the invention, and wherein the selection comprises exposing the transformed material to glyphosate or a salt thereof, and selecting surviving material. The said material may be of plant origin, and may in particular be derived from a monocot selected from the group consisting of barley, wheat, corn, rice, oats, rye, sorghum, pineapple, sugar cane, banana, onion, asparagus and leek.

The invention still further includes a method for regenerating a fertile transformed plant to contain foreign DNA comprising the steps of:

(a) producing regenerable tissue from said plant to be transformed;

(b) transforming said regenerable tissue with said foreign DNA, wherein said foreign DNA comprises a selectable DNA sequence, wherein said sequence functions in a regenerable tissue as a selection device;

(c) between about one day to about 60 days after step (b), placing said regenerable tissue from step (b) in a medium capable of producing shoots from said tissue, wherein said medium further contains a compound used to select regenerable tissue containing said selectable DNA sequence to allow identification or selection of the transformed regenerated tissue;

(d) after at least one shoot has formed from the selected tissue of step (c) transferring said shoot to a second medium capable of producing roots from said shoot to produce a plantlet, wherein the second medium optionally contains the said compound; and (e) growing said plantlet into a fertile transgenic plant wherein the foreign DNA is transmitted to progeny plants in Mendelian fashion, characterised in that the foreign DNA is, or the selectable DNA sequence comprised by the foreign DNA comprises, the polynucleotide according to the invention, and the said compound is glyphosate or a salt thereof. The plant may be a monocot as indicated above—more preferably selected from banana, wheat, rice, corn and barley and the said regenerable tissue may consist of embryogenic calli, somatic embryos, immature embryos etc.

The present invention will be further apparent from the following description taken in conjunction with the associated drawings and sequence listings.

LIST OF SEQUENCES

SEQ ID NO. 1–42—PCR primers.
SEQ ID NO. 43—Rice genomic EPSPS sequence (from ATG).
SEQ ID NO. 44—Rice genomic EPSPS sequence containing double mutation.
SEQ ID NO. 45—FMV enhancer.
SEQ ID NO. 46—CaMV35S enhancer 1.
SEQ ID NO. 47—CaMV35S enhancer 2.
SEQ ID NO. 48—Maize polyubiquitin enhancer.
SEQ ID NO. 49—Rice actin enhancer.
SEQ ID NO. 50—Rice GOS2 enhancer.
SEQ ID NO. 51—Barley Plastocyanin enhancer.
SEQ ID NO. 52—G1 rice EPSPS promoter+5' upstream region.
SEQ ID NO. 53—G3 rice EPSPS promoter+5' upstream region.
SEQ ID NO. 54—G2 rice EPSPS promoter+Adh 1 intron in 5' upstream region.
SEQ ID NO. 55—Maize Adh1 intron.
SEQ ID NO. 56—Wild type rice EPSPS conserved region.
SEQ ID NO. 57—Modified rice EPSPS conserved region.

LIST OF FIGURES

FIG. 1 Rice EPSPS genomic schematic map.

Figure 2:
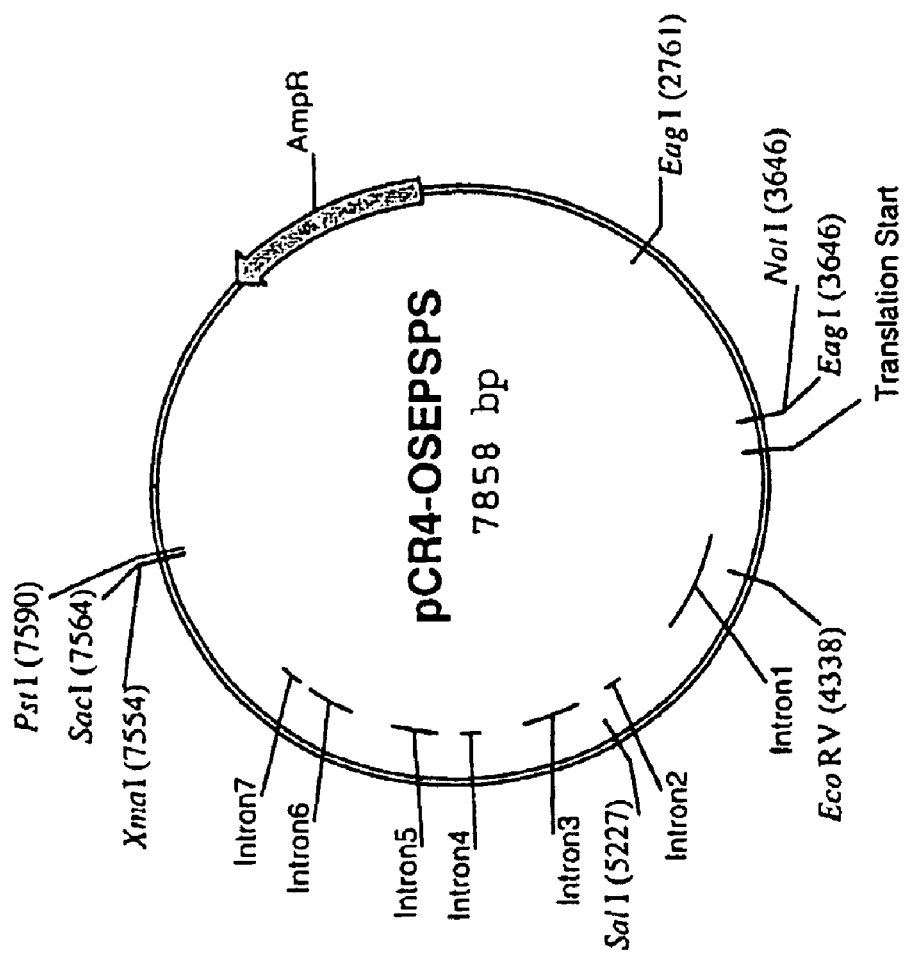

FIG. 2 Vector pCR4-OSEPSPS (rice dmEPSPS gene in vector pCR4-Blunt)

Figure 3:
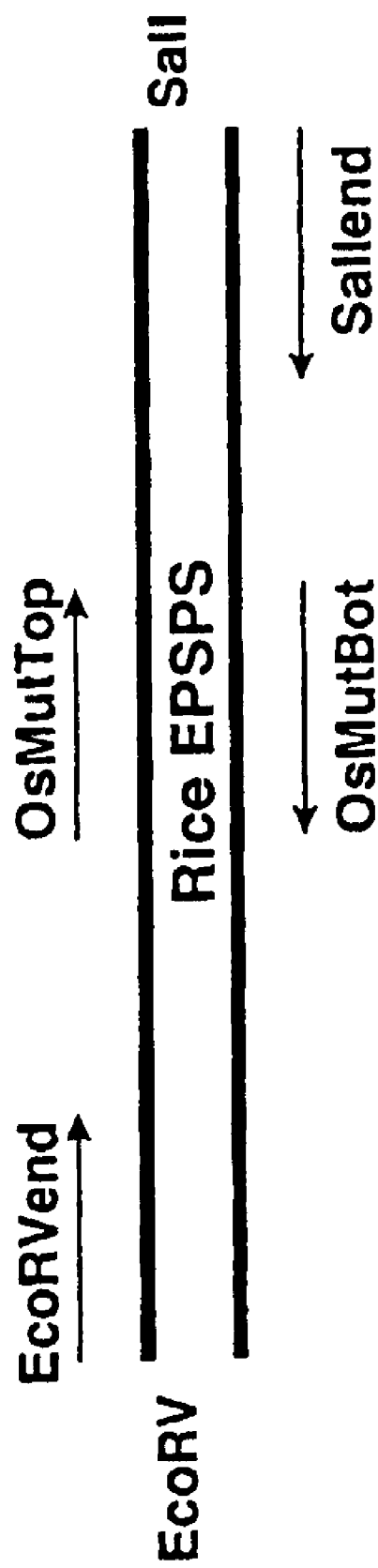

FIG. 3 Schematic representation of strategy used to introduce the double mutation.

Figure 4:
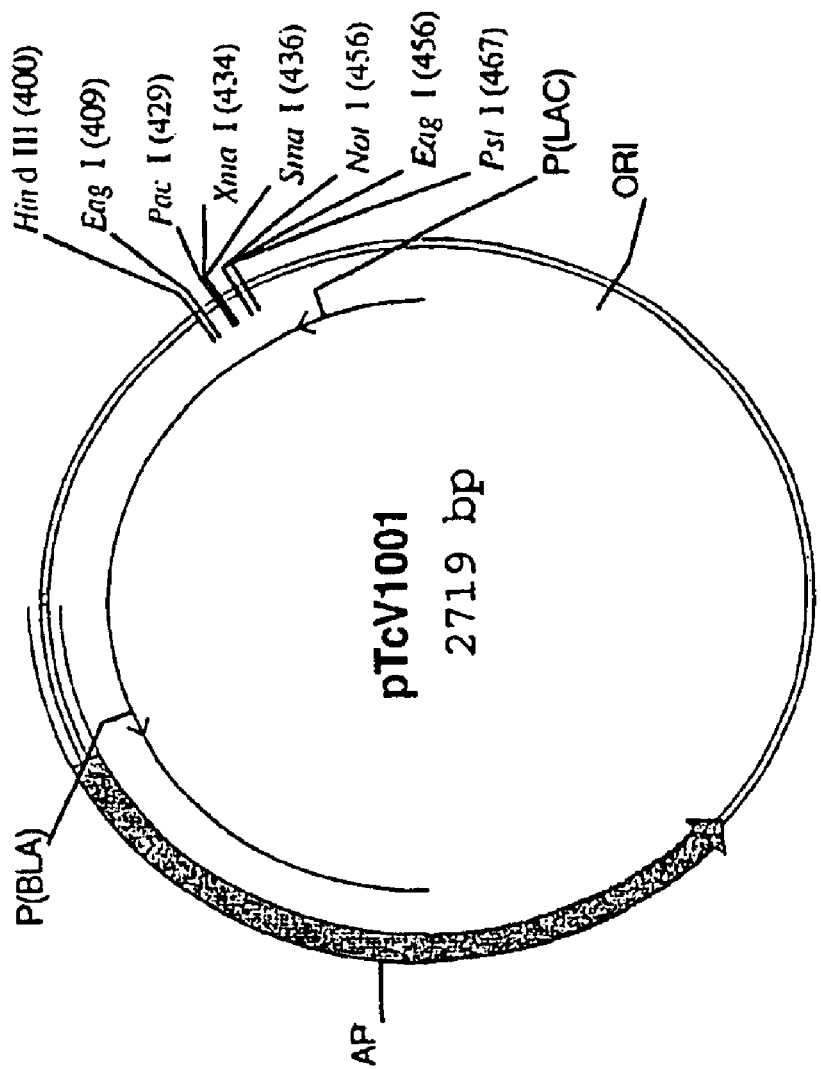

FIG. 4 Vector pTCV1001

Figure 5:
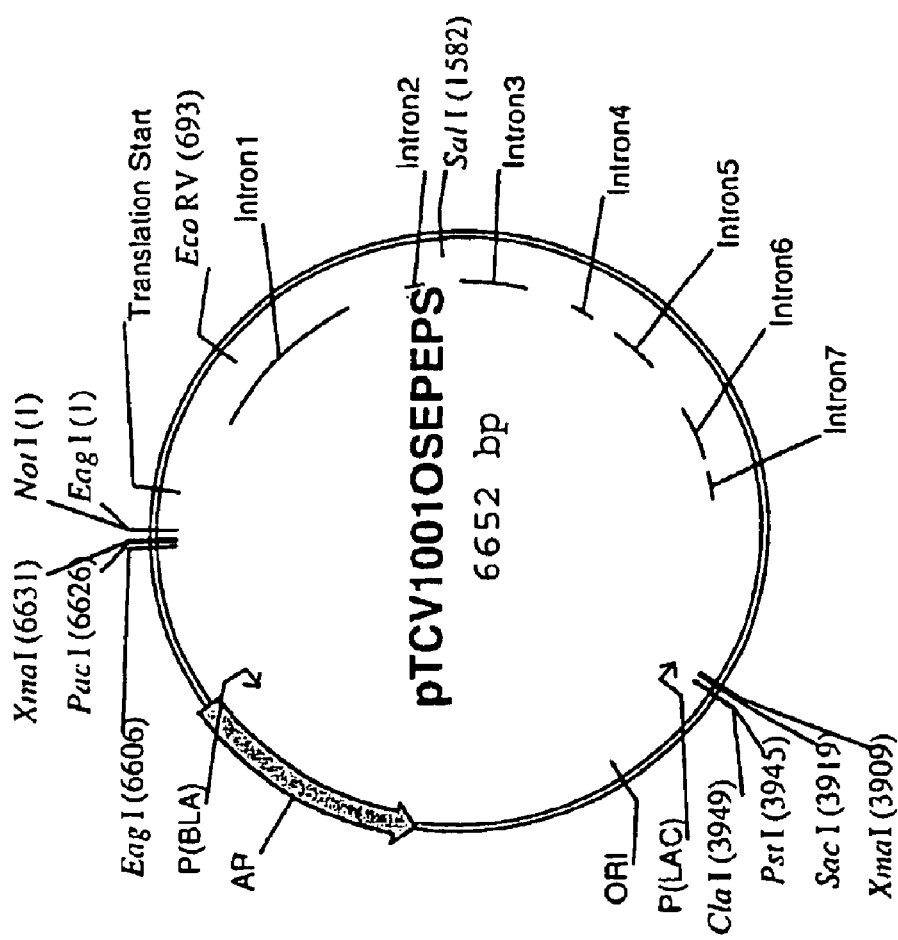

FIG. 5 Vector pTCV1001OSEPSPS (comprises rice dmEPSPS gene in vector pTCV1001).

Figures 6, 7:
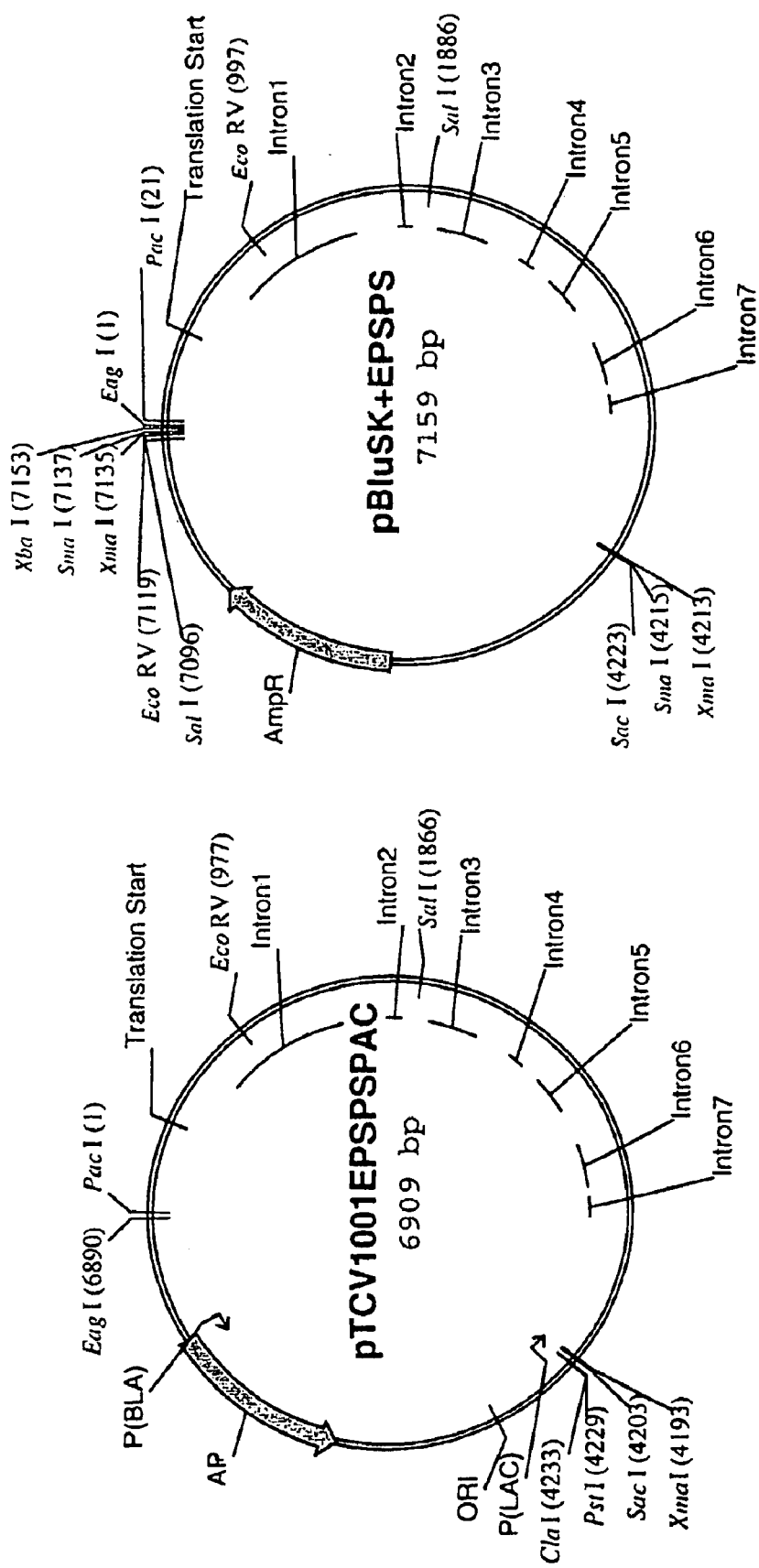

FIG. 6 Vector pTCV1001EPSPSPAC (comprises rice dmEPSPS gene in vector pTCV1001).

FIG. 7 Vector pBluSK+EPSPS (comprises rice dmEPSPS gene in vector pBluescript SK+).

Figure 8:
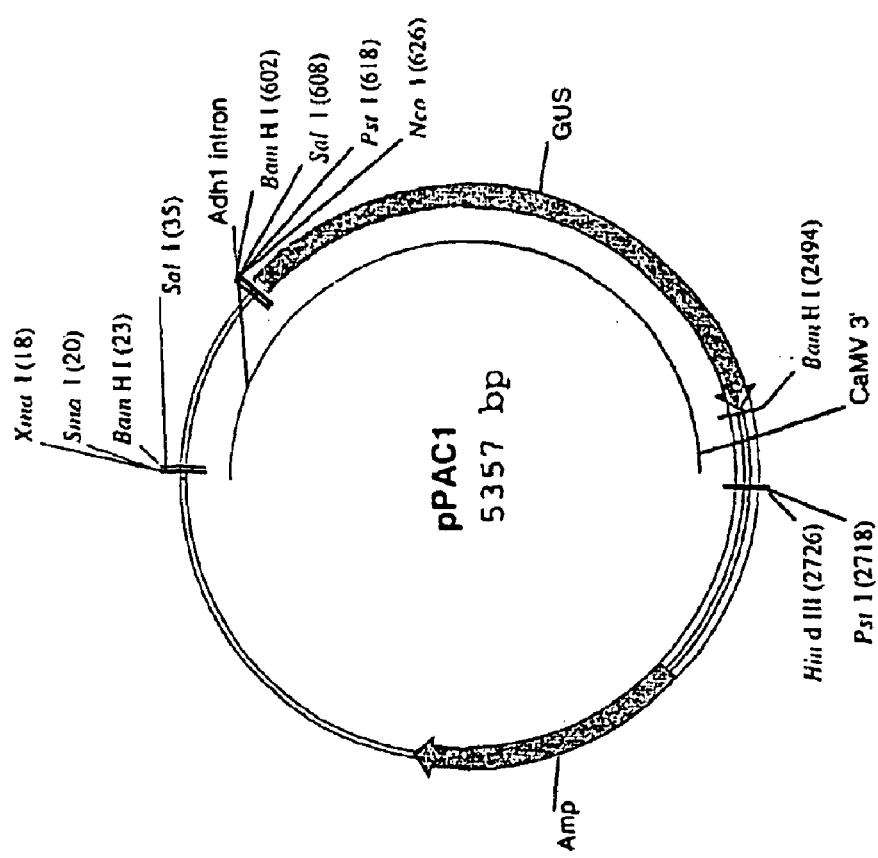

FIG. 8 Vector pPAC1

Figure 9:
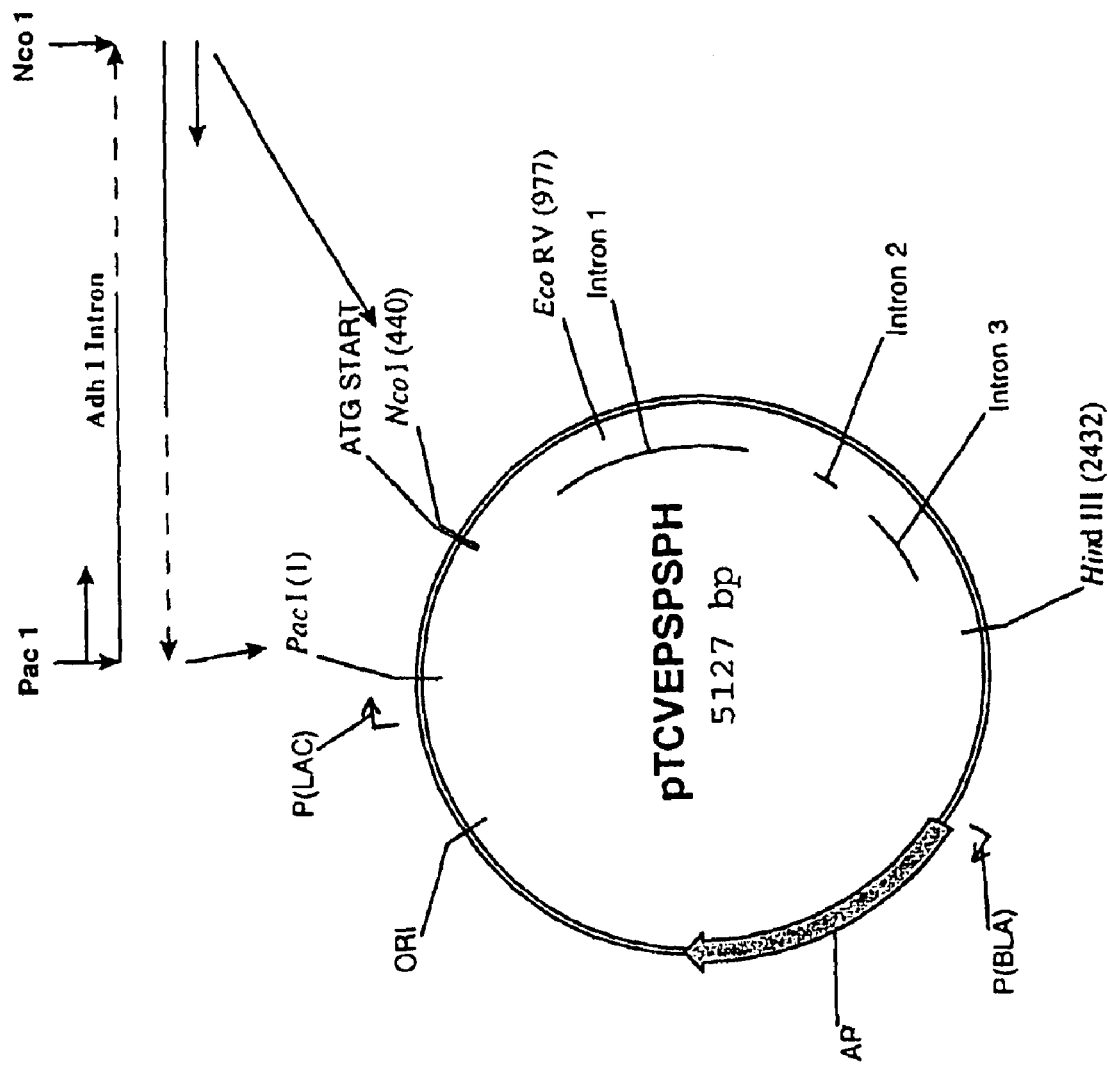

FIG. 9 Vector pTCVEPSPSPH

Figures 10, 11:
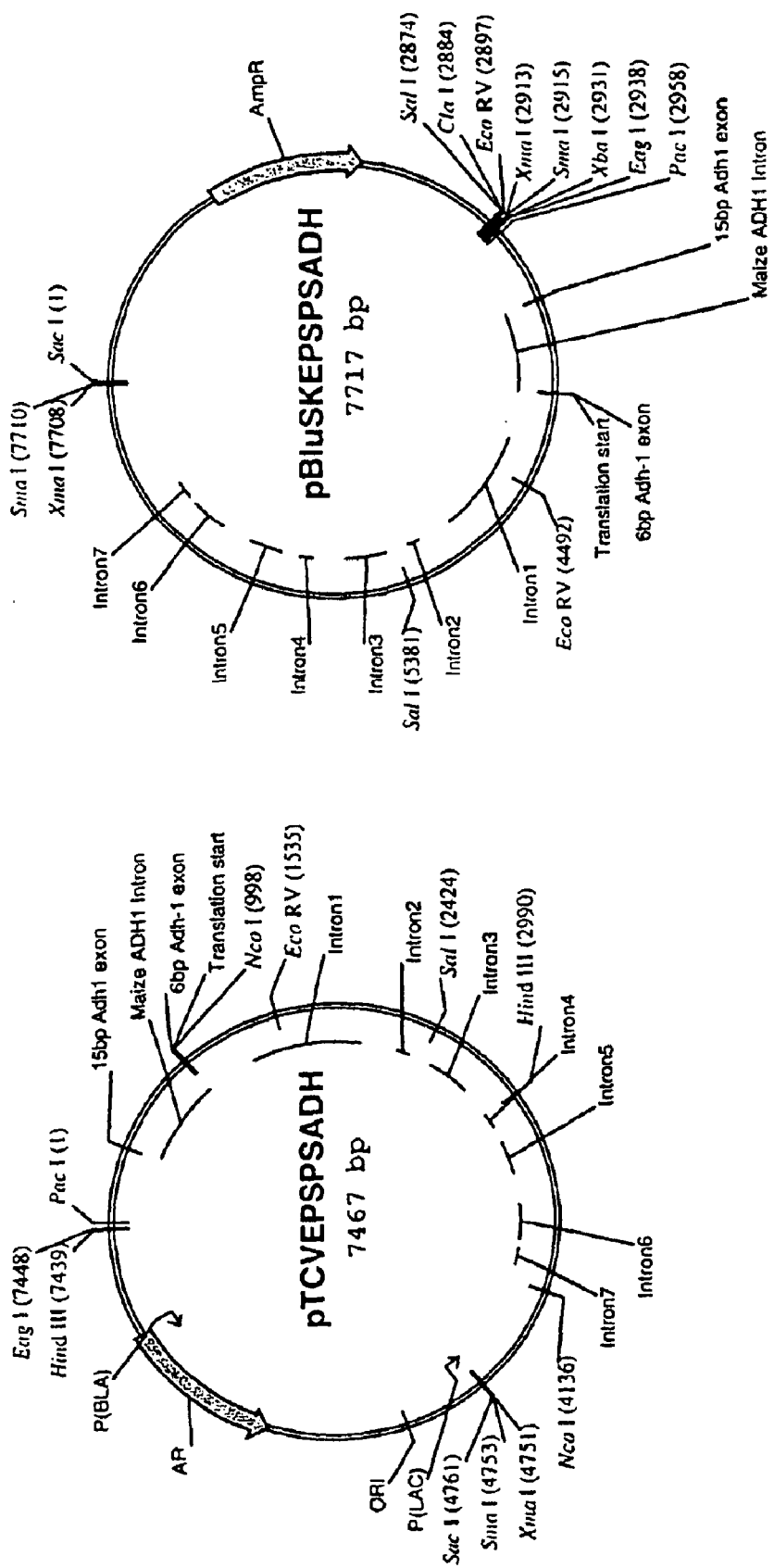

FIG. 10 Vector pTCVEPSPSADH

FIG. 11 Vector pBluSKEPSPSADH (comprises rice dmEPSPS gene and Adh1 intron)

Figure 12:
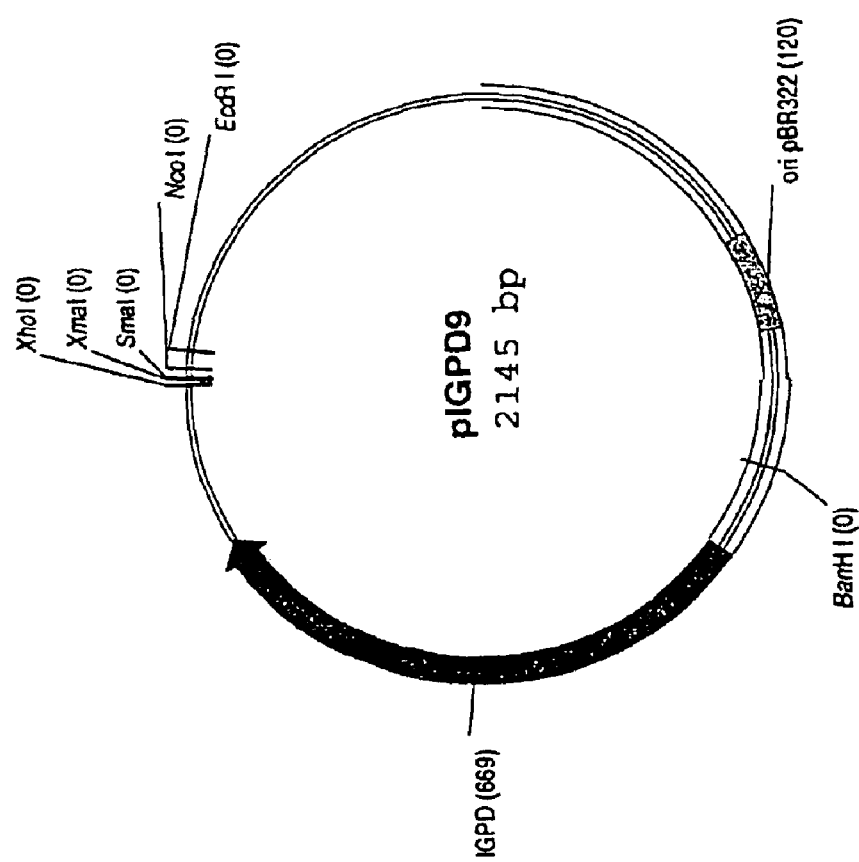

FIG. 12 Vector pIGPD9

Figures 13, 14:
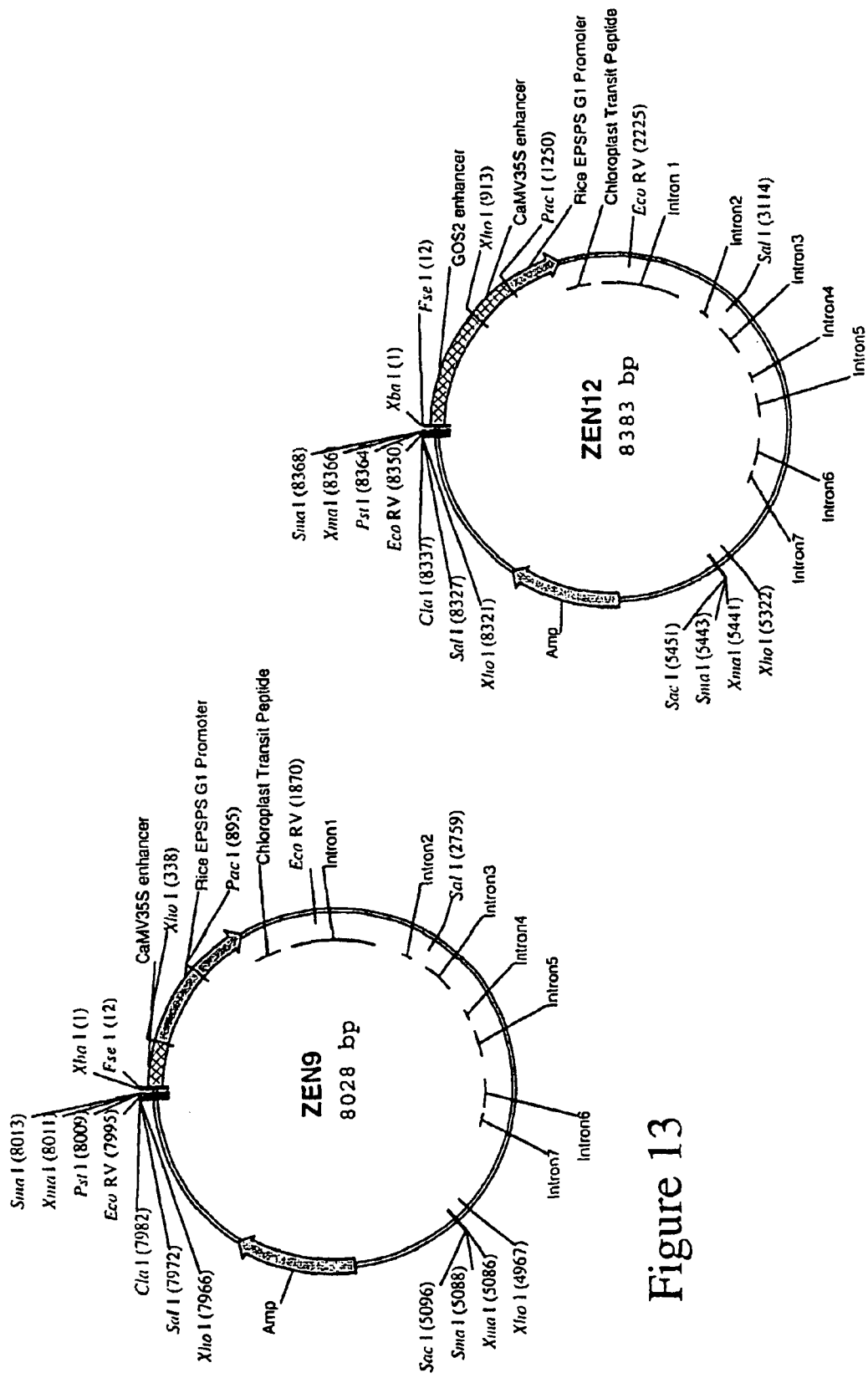

FIG. 13 Vector Zen 9

FIG. 14 Vector Zen 12

Figure 15:
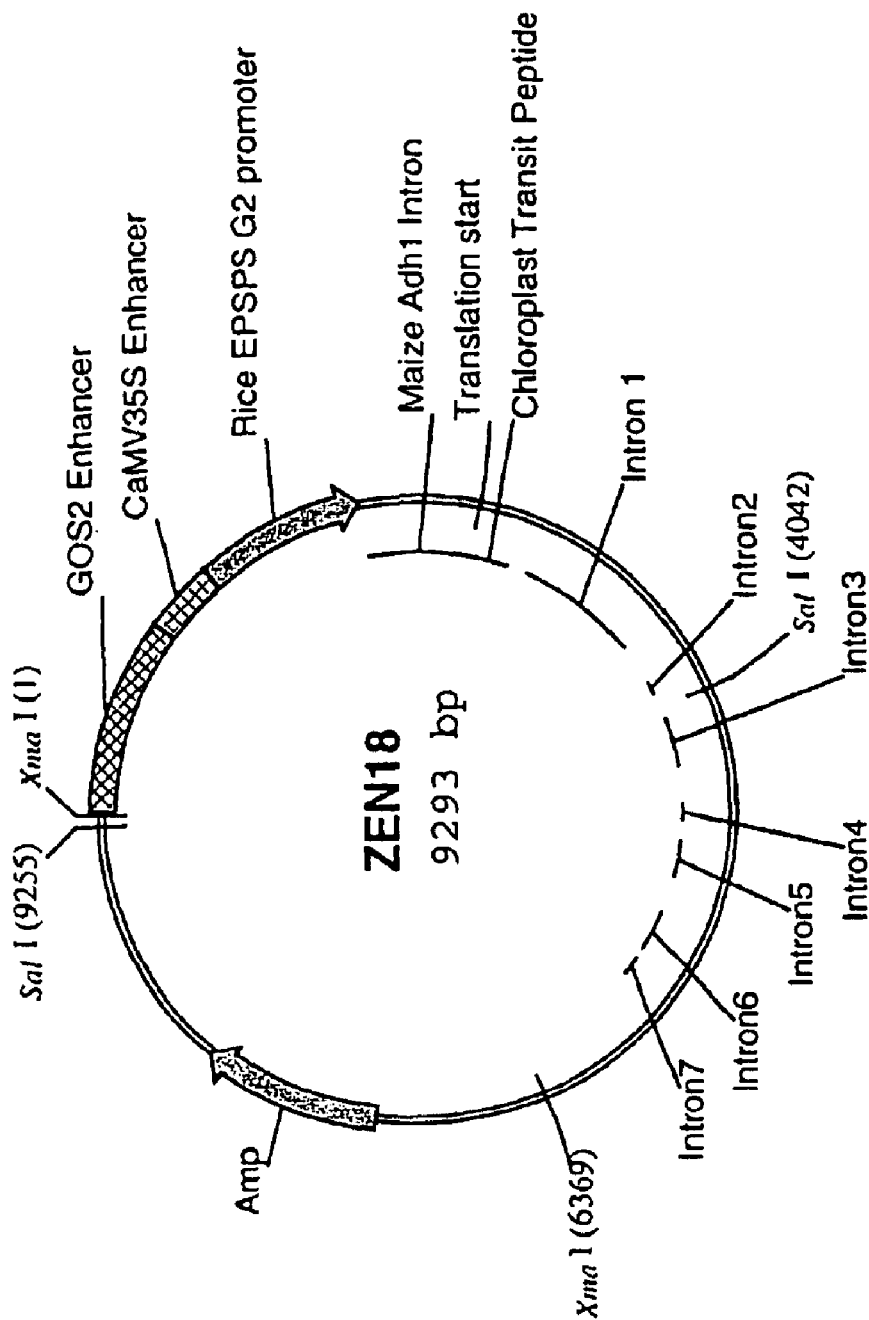

FIG. 15 Vector Zen 18

Figure 16A:
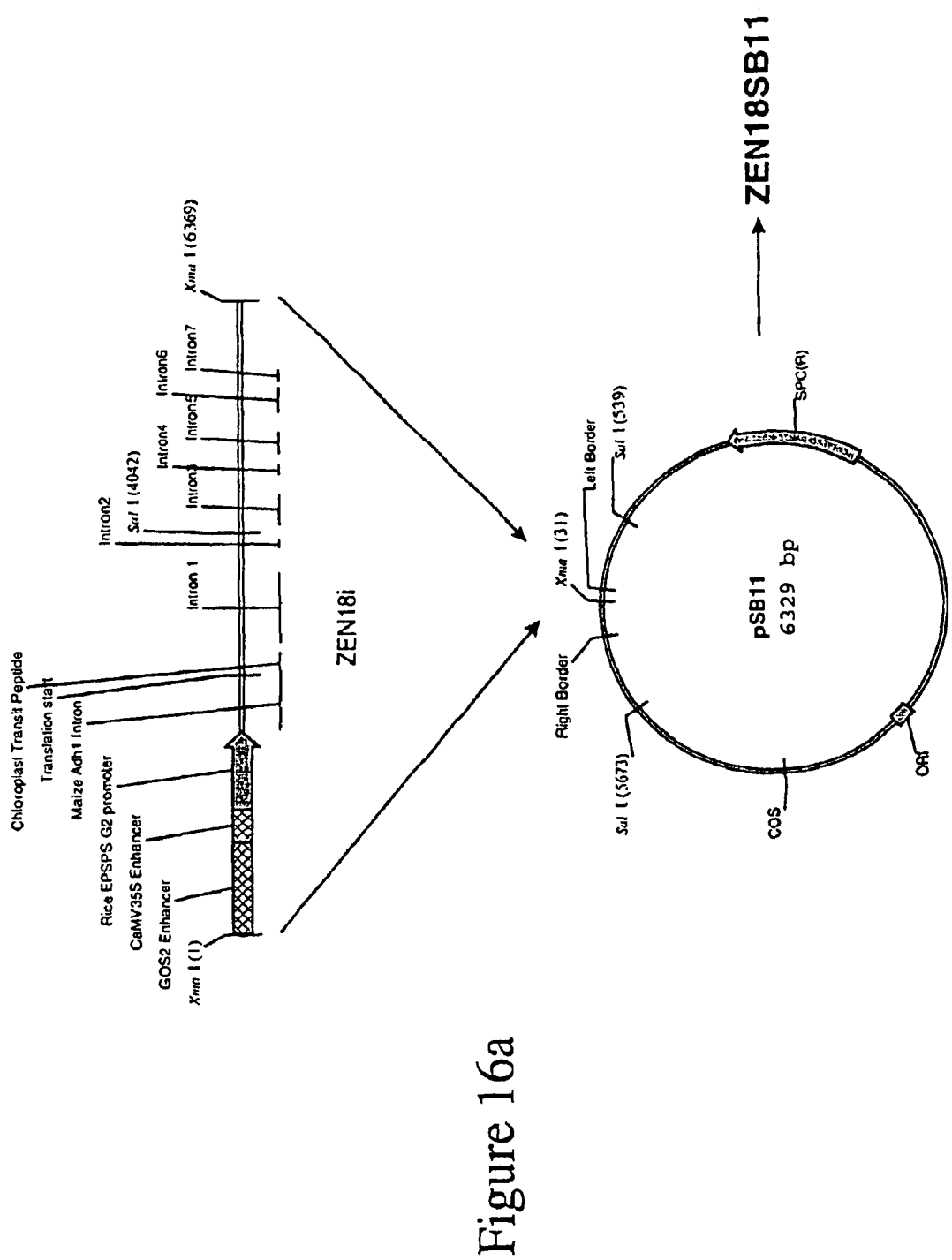
Figure 16B:
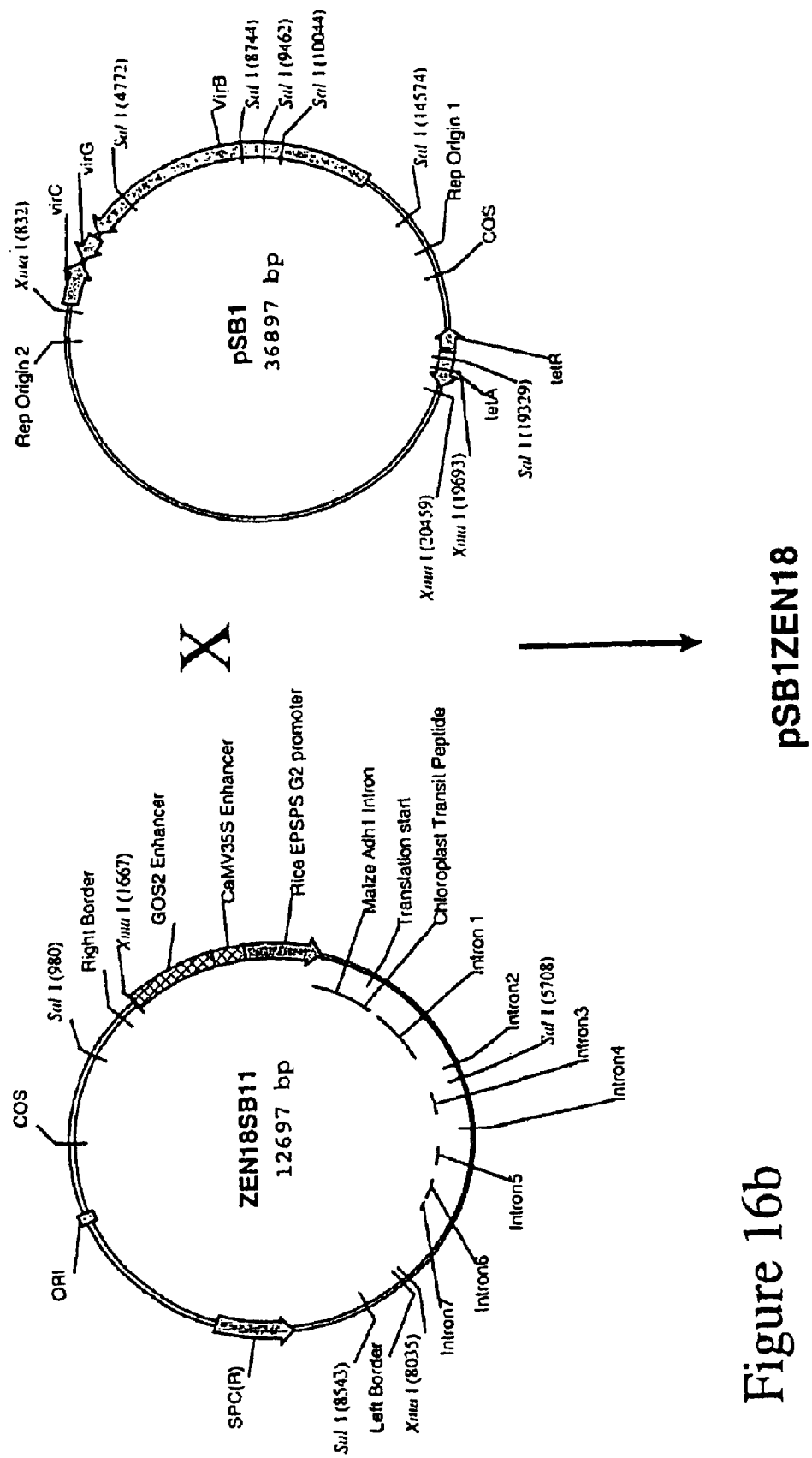
Figure 16C:
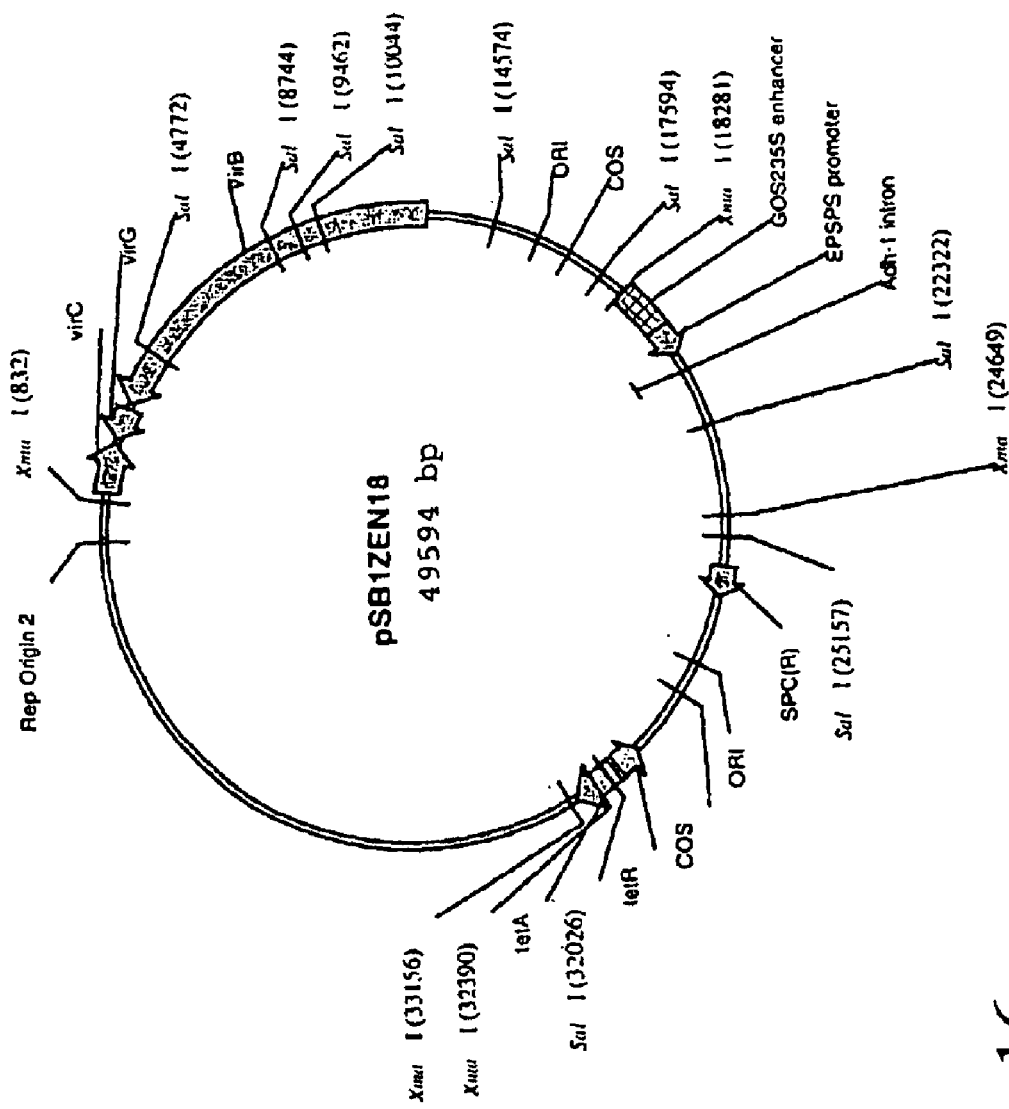

FIG. 16 Introduction of Zen vectors into superbinary vectors isolated from two-week-old rice plants (*Oryza sativa* L.indica var. Koshihikari) using the TRI-ZOL™ method (Life Technologies). First-strand cDNA synthesis is performed using Superscript II reverse transcriptase (Life Technologies) with 200 ng of EPSPS degenerate reverse 10 primer (SEQ ID NO.1) and 2 µg of total RNA according to the supplied protocols. Second strand synthesis and cDNA amplification by PCR is performed using EPSPS degenerate primers 10 and 4 (SEQ ID NO.1 and SEQ ID NO.2) and PCR beads (Pharmacia) according to the manufacturers instructions. All letter codes are standard abbreviations (Eur. J. Biochem. (1985) 150:15)

```
SEQ ID NO.1
EPSPS degenerate reverse 10  5' GCACARGCIGCAAGIGARAAIGCCATIGCCAT 3'

SEQ ID NO.2
EPSPS degenerate forward 4   5' GCWGGAACWGCMATGCGICCRYTIACIGC 3'
```

PRODUCTION OF PLANTS TOLERANT TO GLYPHOSATE TREATMENT THROUGH OVER-EXPRESSION OF A MUTATED EPSPS UNDER THE CONTROL OF A NON-HETEROLOGOUS PROMOTER

The term 'enhancer' as used throughout this specification means those sequences upstream of the promoter which do not comprise the promoter itself but which act to enhance or regulate transcription initiation from the promoter. The term "EPSPS promoter deletion" as used throughout this specification refers to the EPSPS promoter together with nucleotides from the enhancer which is native to the EPSPS gene—i.e. nucleotides which are upstream (5') of the promoter.

In respect of the transformation of plant material, those skilled in the art will recognise that although particular types of target material (e.g. embryogenic cell suspension culture or de-differentiating immature embryos) and particular methods of transformation (e.g. using *Agrobacterium* or particle bombardment) are specified in the examples below, the present invention is not limited to these particular embodiments and such target materials and methods may be used interchangeably. Furthermore, the term "plant cells" as used throughout this description of the invention can refer to isolated cells, including suspension cultures as well as to cells in an intact or partly intact tissue such as embryo, scutella, microspore, microspore-derived embryo or somatic cells from plant organs. Similarly, although the specific examples are limited to maize, wheat and rice, the invention is equally applicable to any of a broad range of agricultural crops and amenity plants which can be transformed using suitable methods of plant cell transformation.

General molecular biological methods are carried out according to Sambrook et al (1989) 'Molecular cloning: A laboratory Manual, 2nd Edn. Cold Spring Harbour Lab. Press.

EXAMPLE 1

Generation of a cDNA Probe for Rice EPSPS

A partial length cDNA encoding rice EPSPS is obtained using reverse transcriptase PCR (RT-PCR). Total RNA is The products are cloned into vector pCR2.1 (Invitrogen) using a TA Cloning kit™ as recommended by the supplier. Plasmid is recovered from selected colonies and the sequence analysed by a process involving computer based homology searches (BLAST) to confirm that the cloned RT-PCR product shows high homology to known plant EPSPS sequences.

EXAMPLE 2

Isolation of Rice EPSPS Genomic Sequence and Cloning of the Rice EPSPS Gene

A region of genomic DNA containing the full rice EPSPS gene and 5' upstream region is isolated from a λ EMBLSP6/T7 genomic library constructed from five-day-old etiolated rice shoots (*Oryza sativa* L.Indica var. IR36) (Clontech). 1×10$^6$ plaque forming units (pfu) are screened using the $^{32}$P-labelled rice EPSPS cDNA probe (example 1) using protocols provided by the manufacturer. Positive plaques are subjected to subsequent rounds of hybridisation screening until plaque purity of a cross-hybridising plaque is obtained. λ-DNA is prepared from the phage pure stock, according to the method described by Sambrook et al., 1989. The DNA obtained is analysed by restriction digest and Southern blotting, using the same $^{32}$P-labelled rice EPSPS cDNA as a probe. Restriction fragments that cross-hybridise are, where applicable, blunt-ended using a method such as Perfectly Blunt™ (Novagen), and cloned into a suitable vector such as pSTBlue (Novagen). The DNA is then sequenced using an ABI377A PRISM automated DNA sequencer. FIG. 1 shows a schematic of the rice EPSPS gene with some of the restriction sites marked.

A 3.86 kb fragment of the rice EPSPS gene, containing the coding region, the EPSPS promoter, some of the 5' upstream region and the terminator is obtained by PCR. Oligonucleotide primer OSGRA1 (SEQ ID NO.3) is used in conjunction with OSEPSPS3 (SEQ ID NO.4) to amplify the desired region. OSEPSPS3 contains additional Sac 1 and Sma 1 restriction enzyme sites to facilitate the subcloning of the gene during the later stages of vector construction. A schematic location of these primers is given in FIG. 1.

```
SEQ ID NO.3
OSSGRA1      5' ATT TCT TCT TCT TCC TCC CTT CTC CGC CTC 3'

SEQ ID NO.4
OSEPSPS3     5' GAG CTC CCC GGG CGA GTG TTG TTG TGT TCT GTC TAA TG 3'
```

High fidelity Pfu Turbo™ polymerase (Stratagene) is used to perform the PCR reaction with DNA obtained from λ preparation (described above) as the amplification template. The PCR product of expected size is cloned into pCRblunt 4-TOPO™ (Invitrogen) and sequenced to check integrity.

EXAMPLE 3

Mutation of T to I and P to S in the Rice EPSPS

The T to I and P to S mutation is obtained by the introduction of two point mutations. These mutations are introduced into the rice genomic EPSPS gene by PCR using oligonucleotide primers containing the desired mutation. A schematic diagram, indicating the binding sites of the primers used, is shown in FIG. 3. Two separate PCR reactions are performed (both using the λ DNA as template).

```
1) EcoRVEnd (SEQ ID NO.5) + OSMutBot (SEQ ID NO.6)
2) OsMutTop (SEQ ID NO.7) + SalIEnd (SEQ ID NO.8)
SEQ ID NO.5
EcoRVEnd     5' GCTTACGAAGGTATGATATCCTCCTACATGTCAGGC 3'

SEQ ID NO.6
OSMutBot     5' GCAGTCACGGCTGCTGTCAATGATCGCATTGCAATTCCAGCGTTCC 3'

SEQ ID NO.7
OsMutTop     5' GGAACGCTGGAATTGCAATGCGATCATTGACAGCAGCCGTGACTGC 3'

SEQ ID NO.8
SalIEnd      5' GGTGGGCATTCAGTGCCAAGGAAACAGTCGACATCCGCACCAAGTTGTTTCAACC 3'
```

The resulting PCR products are joined by using equimolar concentrations of each PCR product as template with the two oligos SalIEnd and EcoRVEnd in a new PCR reaction. An aliquot of the reaction product is analysed by agarose gel electrophoresis and cloned into pCR-Blunt II™ (Invitrogen). Plasmid DNA is recovered and sequenced to detect the successful incorporation of the double mutation.

The DNA fragment containing the double mutation is incorporated into the rice EPSPS genomic clone (FIG. 1) as follows. The clone containing the double mutant is digested with Eco RV and Sal I. The plasmid containing the rice EPSPS DNA PCR product is similarly digested and the Eco RV/Sal I fragment containing the double mutant ligated into the rice EPSPS gene in pCR4Blunt-TOPO™ using standard cloning methods described in Sambrook et al., 1989 and transformed into competent E. coli. Plasmid is recovered from resultant colonies and sequenced in order to confirm the presence of the double mutation with no further alterations. This plasmid, pCR4-OSEPSPS, is shown in FIG. 2.

The genomic rice EPSPS gene containing the double mutant (FIG. 2) is excised from pCR4-Blunt-TOPO™ using Pst 1 and Not 1 and ligated into pTCV1001 (FIG. 4), to generate pTCV1001OSEPSPS (FIG. 5) and this is transformed into E. coli for amplification. Next, the Pac 1/Eco RV restriction fragment is excised from the λ DNA (FIG. 1) and inserted into pTCV1001OSEPSPS (FIG. 5) to generate pTCV1001EPSPSPAC (FIG. 6). The rice EPSPS gene, now containing sequence from Pac 1 to Sac1 (FIG. 6), is excised from pTCV1001EPSPSPAC (FIG. 6) as an Eag 1/Sac 1 fragment and ligated into similarly digested pBluescript SK+ to make pBluSK+EPSPS (FIG. 7). Further rice EPSPS upstream regions and desired enhancers are assembled (as described below) and ligated into the pBluescript SK+ vector using Xba 1/Pac 1.

EXAMPLE 4

Generation of Singly Enhanced: Rice EPSPS Promoter Fusions

FIG. 1 indicates the binding sites of the primers G1 and G2 used to generate a series of deletions at the 5' end of the rice EPSPS gene. The G1 and G2 primers are used in combination with the RQCR10 primer using the rice EPSPS lambda DNA template and Pfu Turbo™ polymerase (Stratagene) using protocols provided by the supplier.

```
SEQ ID NO.9
G1           5' CGCCTGCAGCTCGAGGTTGGTTGGTGAGAGTGAGACACC 3'

SEQ ID NO.10
G2           5' CGCCTGCAGCTCGAGGCCACACCAATCCAGCTGGTGTGG 3'

SEQ ID NO.11
RQCR10       5' GAACCTCAGTTATATCTCATCG 3'
```

The products obtained are analysed by agarose gel electrophoresis and cloned into pCR-Blunt II-TOPO™ vector (Invitrogen). The sequence of the resulting products is determined to ensure that there is no alteration in the sequence of the rice genomic EPSPS clone. Clones to progress are selected based on their orientation within the vector by establishing whether or not Xho I digestion removes only the polylinker sequence rather than the whole insert from the vector.

The sequences of the CaMV35 S and FMV 35S genes and their associated 5' upstream regions are published in the EMBL, database (for example accession v00141 and x06166). Primers are designed so as to amplify only the upstream enhancer regions of the said genes. The CaMV35S enhancer1 (SEQ ID NO. 36) is thus obtained by PCR using primers SEQ ID NO. 12 and SEQ ID NO. 13 in conjunction with Pfu Turbo™ polymerase and pMJB1 DNA (A59870) as the template. Alternatively a different region of the CaMV35S enhancer is obtained using similar methods (SEQ ID NO. 37). The FMV35S enhancer is synthesised chemically (SEQ ID NO. 35).

The following oligonucleotide primers are used.

```
SEQ ID NO.12
35S5         5' CGCTCTAGAGGCCGGCCAACATGGTGGAGCACGACACACTTGTCTAC 3'

SEQ ID NO.13
35S3         5' CGCTGCAGCTCGAGCATCAATCCACTTGCTTTGAAGACG 3'
```

The sequence of the amplified and cloned molecules is confirmed following cloning into the PCR Blunt-II-TOPO vector (Invitrogen). The pCR Blunt-II-TOPO vector, containing the EPSPS 5' UTR deletion is digested with Xba 1/Xho 1. The Enhancer is removed from its respective pCR Blunt-II-TOPO vector also using Xba 1/Xho 1 digestion and ligated into the first vectors containing the EPSPS promoter deletions generated by PCR.

EXAMPLE 5

Generation of Doubly Enhanced: Rice EPSPS Promoter Fusions

In order to further increase expression from the rice EPSPS promoter an additional enhancer may be used in conjunction with either the 35S or FMV enhancer. In one example of a cloning strategy to achieve this, enhancer/EPSPS fusions are initially made (similar to example 4) comprising a single (first) enhancer. Such first enhancers are selected from the upstream regions 5' of the promoters of the rice GOS2, rice actin 1, maize polyubiquitin, CaMV 35S, FMV 35S and barley plastocyanin genes. The nucleotide sequences of these regions are published in the EMBL database (accession number x51910, x15865, u29159, v00141, x06166 and z28347 respectively). Primers are designed so as to amplify only the desired transcriptional enhancer regions 5' to these genes (SEQ ID NO. 15 to 22).

```
SEQ ID NO.15
Barley5      5' CGCTCTAGAGGCCGGCCCCAAAATCTCCCATGAGGAGCACC 3'

SEQ ID NO.16
Barley3      5' CGCTGCAGCTCGAGCCGCCTCTCCATCCGGATGAGG 3'

SEQ ID NO.17
OSGOS5       5' CGCTCTAGAGGCCGGCCGAATCCGAAAAGTTTCTGCACCGTTTTCACC 3'

SEQ ID NO.18
OSGOS3       5' CGCTGCAGCTCGAGGCTGTCCTCCGTTAGATCATCG 3'

SEQ ID NO.19
MPU5         5' GAC TAG TGG CCG GCC ATC AGC GGC CAG CTT TTG TTC 3'

SEQ ID NO.20
MPU3         5' TTA ACT AGT GAG GAG GCC GCC TGC CGT GC 3'

SEQ ID NO.21
RA5          5' CGCCTCTAGAGGCCGGCCGATATCCCTCAGCCGCCTTTCACTATC 3'

SEQ ID NO.22
RA3          5' CGCTGCAGTGCTCGCGATCCTCCTCGCTTTTCC 3' pst?
```

DNA is isolated from greenhouse grown plants (maize, barley or rice) using the DNAeasy protocol (Qiagen) and used as the starting template for PCR amplification. The PCR products are cloned into pCR-Blunt-II-TOPO and sequenced to check authenticity. The enhancer EPSPS fusion is made as described previously in Example 4 (using Xba/Xho1 swap) except in the case of rice actin 1, where the enhancer is inserted as an Xba 1/Pst 1 fragment (a Xho1 site is replaced with a Pst1 site due to the presence of a Xho 1 site in the Rice actin enhancer) and maize polyubiquitin, where the enhancer is inserted as a Spe 1/Xho 1 fragment (the Xba 1 site is replaced with a Spe 1 site due to the presence of a Xba 1 site in the maize polyubiquitin enhancer). Note that an internal Xho1 site is used with respect to the maize polyubiquitin enhancer region. The second enhancer, which can be either the CaMV35S enhancer or the FMV enhancer is amplified using the primers 35SXho and 35S3 (SEQ ID NO 23 and SEQ ID NO. 13) (35S) or FMVXho and FMV3 (SEQ ID NO 25 and SEQ ID NO 26) respectively. These primers facilitate the introduction of a Xho1 site (or Pst 1 site) at the 5' and 3' termini of the enhancer. Alternatively a Pac 1 site is introduced at the 3' end in place of the Xho1 site using primers 35SPac (SEQ ID NO. 24) or FMVPAC3 (SEQ ID. 27).

```
SEQ ID NO.23
35Sxho      5' CTGCAGCTCGAGAACATGGTGGAGCACGACACACTTGTCTAC 3'

SEQ ID NO.24
35SPAC      5' TTAATTAACATCAATCCACTTGCTTTGAAGACG 3'

SEQ ID NO.25
FMVXho1     5' CTCGAGGGCCGGCCGCAGCTGGCTTG 3'

SEQ ID NO.26
FMV3        5' CTCGAGTTTTGTGGTCGTCACTGCGTTCG 3'

SEQ ID NO.27
FMV3Pac     5' TTAATTAATTTTGTGGTCGTCACTGCGTTCG 3'
```

Once sequenced, the PCR product, either Xho 1: Xho 1, Pst 1/Pac 1 (when rice actin is the first enhancer) or Xho 1/Pac 1, is introduced into the construct which comprises the first enhancer: EPSPS gene fusion either at the Xho1 site or between the Xho 1 and Pac 1 or Pst 1 and Pac 1 restriction sites as required. The introduction at the Xho 1 site is used to construct the double enhancer fusion constructs comprising either the G1 or G2 EPSPS promoter deletions. Both the Xho 1/Pac 1 and Pst 1/Pac 1 fragments are used to construct double enhancer fusions comprising the G3 EPSPS promoter deletion. Where the second enhancer is introduced as an Xho 1 fragment the orientation of the enhancer is determined by PCR.

EXAMPLE 6

Insertion of Adh1 Intron into the 5' UTR of the Rice EPSPS Gene

The insertion of the Maize Adh1 intron 1 into the desired rice EPSPS promoter deletion (e.g. made as described in Example 4) is performed prior to the generation of the fusion construct with the desired enhancer(s). In this particular example the Adh1 intron is introduced into the G2 EPSPS promoter deletion. The skilled man will appreciate that similar methodology can be adopted to incorporate the Adh1 intron into other EPSPS promoter deletions. The maize Adh1 intron is inserted into the constructs by PCR. The Adh 1 intron is amplified from a suitable source, such as maize genomic DNA or a vector such as pPAC1 (FIG. 8) using primers Adh5 (SEQ ID NO. 28) and Adh3 (SEQ ID NO. 29):

```
SEQ ID NO.28
Adh5 CCCATCCTCCCGACCTCCACGCCGCCGGCAGGATCAAGTGCAAAGGTCCGCCTTGTTTCTCCTCTG

SEQ ID NO.29
Adh3 GACGCCATGGTCGCCGCCATCCGCAGCTGCACGGGTCCAGGAAAGCAATC
```

The resulting PCR product is denatured and used as a primer in conjunction with Adh5Pac (SEQ ID NO. 30) to amplify the desired product using the vector pTCV1001EPSPSPAC (FIG. 6) as template.

```
SEQ ID NO.30
Adh5Pac CGAGTTCTTATAGTAGATTTCACCTTAATTAAAAC
```

The resulting PCR product is cloned into PCR-Blunt II (Invitrogen). The Pac 1:Hind III fragment is excised from the rice genomic clone (FIG. 1) and inserted into pTCV1001 to generate pTCVEPSPSPH (FIG. 9). Next, the Pac 1/Nco 1 PCR product obtained above and comprising the Adh 1 intron is inserted into pTCVEPSPH as shown by the schematic (FIG. 9). The Pac 1:Eco RV fragment present in the cloned EPSPS gene containing the double mutant (FIG. 10) is excised and replaced with the Pac 1/Eco RV fragment from pTCVEPSPSPH that comprises the Adh 1 intron sequence (FIG. 9). Finally the full EPSPS gene comprising the Adh 1 sequence is excised from pTCVEPSPSADH (FIG. 10) as an Eag 1/Sac 1 fragment and cloned into pBluescript SK+ to give pBluSKEPSPSADH (FIG. 11).

EXAMPLE 7

Introduction of Optimised Pre ATG Consensus Sequence (Kozak) Via Site Directed Mutagenesis for Constructs Comprising the Maize Adh1 Intron Optionally, site directed mutagenesis is performed on constructs containing the Adh1 intron using the Quick-Change Site Directed Mutagenesis kit (Stratagene). This is performed on the Pac1/Sac1 EPSPS fragment in pBluescript SK+ (FIG. 11) prior to fusion with the enhancer: EPSPS promoter fusions. The following oligonucleotide are used according to the supplied protocols to optimise the KOZAK sequence.

```
SEQ ID NO.31
Oskozak     5'GGACCCGTGCAGCTGCGGTACCATGGCGGCGACCATGGC 3'

SEQ ID NO.32
OSkozakrev  5'GCCATGGTCGCCGCCATGGTACCGCAGCTGCACGGGTCC 3'
```

Clones are analysed by restriction analysis, using Kpn 1, on recovered plasmid. The correctly altered DNA is characterised by an additional Kpn 1 restriction site compared to the un-altered DNA. The sequence is then verified by automated DNA sequencing. The altered DNA sequence may be transferred original constructs using the unique restriction enzyme sites of Sph 1 or Pac 1 at the 5' end and Avr II or Eco RV at the 3' end as appropriate for each vector.

EXAMPLE 8

Completion of EPSPS Expression Cassettes Comprising, in the 5' to 3' Direction, Enhancer Region(s), Rice EPSPS Promoter Upstream Region, EPSPS Promoter, EPSPS 5'UTR+ (Optional) Maize Adh1 Intron 1, Rice EPSPS Plastid Transit Peptide Coding Region, Rice Mature EPSPS Coding Region and Rice EPSPS Gene Terminator Region The singly and doubly enhanced rice EPSPS promoter fusions (Examples 4 and 5) contained within the pCR Blunt-II-TOPO vectors are excised using Xba 1 and Pac 1 and inserted into the similarly digested pBluescript SK+ clone containing the remainder of the rice EPSPS sequence (FIGS. 7/11). However, when the maize polyubiquitin enhancer:EPSPS fusion is to be used this is firstly cloned into pBluescript using Spe1/Pac 1. The remainder of the rice EPSPS sequence is then inserted as Pac 1/Sac 1 to complete the expression cassette. This final cloning step results in the required gene constructs. Examples of constructs obtainable using the above strategies are given below in Table 1. Schematic maps are given in FIGS. 13–15.

| Clone | First enhancer | Second enhancer | EPSPS Promoter deletion | Adh1 Intron | EPSPS genomic coding region | EPSPS Terminator |
|---|---|---|---|---|---|---|
| ZEN9 | CaMV35S | None | G1 | No | Yes | Yes |
| ZEN11 | RA | 35S | G1 | No | Yes | Yes |
| ZEN14 | RA | 35S | G3 | No | Yes | Yes |
| ZEN15 | MPU | 35S | G3 | No | Yes | Yes |
| ZEN20 | BPC | 35S | G2 | Yes | Yes | Yes |
| ZEN18 | GOS2 | 35S | G2 | Yes | Yes | Yes |
| ZEN12 | GOS2 | 35S | G3 | No | Yes | Yes |
| ZEN23 | FMV | None | G2 | Yes | Yes | Yes |
| ZEN24 | FMV | 35S | G2 | Yes | Yes | Yes |
| ZEN25 | 35S | FMV | G2 | Yes | Yes | Yes |

EXAMPLE 9

Subcloning of EPSPS Expression Cassettes from Bluescript into pIGPD9

Where desired and especially for transformation of plants by direct DNA methods (whiskers, bombardment and protoplasts), the EPSPS expression constructs are excised from pBluescript using Xma 1 and cloned into pIGPD9 (FIG. 12). The use of this vector for transformation avoids transfer of antibiotic resistance genes to the plant since selection relies on complementation of an auxotrophic his B *E. coli* mutant with the gene expressing IGPD (the his B product). The pIGPD9-derived plasmids deriving from insertion of the Xma 1 fragments of pZEN9, 11, 12, 14, 15, 16, 18, 20, 23, 24 and 25 are termed pZEN9i, pZEN11i, pZEN12i. etc Large DNA preparations for use in plant transformation are obtained using the Maxi-prep procedure (Qiagen) using protocols provided by the Manufacturer.

EXAMPLE 10

Preparation of DNA for Plant Transformation

The above procedure describes the assembly of 'EPSPS expression cassettes' comprising, in a 5' to 3' direction, an enhancer sequence(s), an EPSPS promoter from rice, a region encoding a rice EPSPS transit peptide, a region encoding a mature rice EPSPS enzyme which is resistant to glyphosate through having T to I and P to S changes at the specified positions and a rice EPSPS gene terminator.

Optionally the desired cassettes also further comprise a drug selection marker gene (e.g ampicillin resistance, kanamycin resistance etc.) a T-DNA Left or Right Border region and (optionally) a scaffold attachment region added 5' and/or 3' to the above described construct. The skilled man will recognise that similar methods to those described above can be used to obtain these added components and clone them into the desired positions.

EXAMPLE 11

Transformation of Corn Lines Using an Agrobacterium Strain Containing a Superbinary Vector Which Includes an EPSPS Expression Cassette Between the Right and Left Borders of the T-DNA; Selection and Regeneration of Plant Cells and Plants Which are Resistant to Glyphosate Construction of Agrobacterium Strain Bluescript plasmid DNA (e.g. ZEN9, ZEN11, ZEN14, ZEN15, ZEN18, ZEN20, ZEN12, ZEN23, ZEN24 or ZEN25) is digested with either Xma 1 or with Xba 1/Sac 1 and the thus-obtained (~5–6.5 kb) EPSPS-encoding fragment ligated into a position within the cloning site located between the right and left T-DNA borders of similarly restricted pSB1. In the case, for example, of using the Xma 1 fragment of pZEN 18 this ligation creates the plasmid pZEN18SB11 (FIG. 16). The construction of plasmid pSB11 and the construction of its parent, pSB21, is described by Komari et al (1996, Plant J. 10: 165–174). The T-DNA region of pZEN18 is integrated into the superbinary pSB1 vector. (Saito et al EP 672 752 A1) by a process of homologous recombination (FIG. 16) to create the plasmid, pSB1ZEN18. To achieve this the plasmid pZEN18SB 11 is transformed into E. coli strain HB101 which is then, according to the triple cross method of Ditta et al (1980, Proc. Natl. Acad. Sci. USA 77: 7347–7351), mated with an Agrobacterium LBA4404 harbouring pSB1 to create the transformed strain of Agrobacterium, LBA4404 (pSB1ZEN18) in which the presence of the cointegrate plasmid pSB1ZEN18 is selected for on the basis of resistance to spectinomycin. The identity of pSB1ZEN18 is also confirmed on the basis of Sal 1 restriction analysis (FIG. 16). LBA4404 strains containing the directly analogous constructs pSB1ZEN9, pSB1ZEN11, pSB1ZEN12, pSBZEN14 etc are similarly constructed starting from the Xma1 fragments of pZEN9, ZEN11, ZEN12, ZEN 14 etc.

Alternatively, using similar methods to those described above, a similar fragment of p ZEN9, ZEN 11 etc is homologously recombined into a position between the right and left borders of the superbinary vector pTOK162 (FIG. 1 in U.S. Pat. No. 5,591,616) to generate a similar set of cointegrate plasmids selected for in Agrobacterium on the basis of combined resistance to kanamycin and spectinomycin.

Agrobacterium strain LBA4404 which has a helper plasmid PAL4404 (having a complete vir region) is available from the American Type Culture Collection (ATCC 37349). An alternative useful strain is Agrobacterium EHA101 (1986, Hood et al, J. Bacteriol., 168(3): 1283–1290) which has a helper plasmid having the vir region from the strongly virulent strain Agrobacterium tumefaciens A281.

Preparation of Agrobacterium Suspensions

Agrobacterium strains LBA4404(pSB1ZEN9), LBA4404 (pSB1ZEN11) etc are each streaked onto plates containing 'PHI-L' solid medium and cultured at 28 C. in the dark for 3 to 10 days.

PHI-L medium is as described on page 26 (Example 4) of WO 98/32326. PHI-L medium made up in double-distilled water comprises 25 ml/l of stock solution A, 25 ml/l of stock solution B, 450.9 ml/l of stock solution C and 50 mg/l of spectinomycin. Stock solutions are sterilised by autoclaving or filtration. Stock solution A is 60 g/l $K_2HPO_4$ and 20 g/l $NaH_2PO_4$ adjusted to pH 7.0 with KOH: stock solution B is 6 g/l Mg $SO_4.7H_2O$, 3 g/l KCl, 20 g/l $NH_4Cl$, 0.2 g/l $CaCl_2$ and 50 mg/l $FeSO_4.7H_2O$: stock solution C is 5.56 g/l of glucose and 16.67 g/l of agar (A-7049, Sigma Chemicals, St Louis, Mo., USA)

Alternatively the Agrobacteria are cultured for 3–10 d on a plate containing YP medium (5 g/l yeast extract, 10 g/l peptone, 5 g/l NaCl, 15 g/l agar at pH 6.8) as described by Ishida et al (1996, Nature Biotechnology, 14, 745–750) or, alternatively, as described by Hei et al in U.S. Pat. No. 5,591,616 (AB medium (Drlica and Kado, 1974; Proc. Natl. Acad. Sci. USA 71:3677–3681)) but, in each case, modified to provide the appropriate antibiotic selection (e.g. containing 50 mg/ml spectinomycin in the case of Agrobacterium strain LBA4404(pSB1ZEN9) etc. or containing both 50 mg/ml spectinomycin and 50 mg/ml kanamycin in the case that Agrobacterium containing a pTOK 162-derived superbinary vector is used).

Plates of Agrobacterium made as described above are stored at 4 C. and used within a month of preparation. For preparation of suspensions a single colony from the master plate is streaked out onto a plate containing, at pH 6.8, 5 g/l yeast extract (Difco), 10 g/l peptone (Difco), 5 g/l NaCl, 15 g/l agar (Difco) and 50 mg/l of spectinomycin (or as appropriate for the particular strain of Agrobacterium ). Plates are incubated at 28 C., in the dark for 2d.

Suspensions of Agrobacterium for transformation of plant material are prepared in a similar manner to described in U.S. Pat. No. 5,591,616. (Using good microbiological practice to avoid contamination of aseptic cultures) 3×5 mm loopfuls of Agrobacterium are removed from plates, transferred and suspended in 5 ml of sterile AA liquid medium in a 14 ml Falcon tube. As used here, AA liquid medium at pH 5.2 contains the major inorganic salts, amino acids and vitamins defined by Toriyama and Hinata (1985) in Plant Science 41, 179–183), the minor inorganic salts of Murashige and Skoog medium (Murashige and Skoog, 1962 in Physiol. Plant 15, 473–497), 0.5 g/l of casamino acids (casein hydrolysate), 1 mg/l of 2,4-dichlorophenoxyacetic acid (2,4-D), 0.2 mg/l of kinetin, 0.1 mg/l of gibberellin, 0.2M glucose, 0.2M sucrose and 0.1 mM acetosyringone.

Alternatively, suspensions of Agrobacterium for transformation of plant material are prepared in a similar manner to described in WO 98/32326. 3×5 mm loopfuls of Agrobacterium are removed from plates, transferred and suspended in 5 ml of the sterile PHI-A basic medium as described in Example 4 on page 26 of WO 98/32326 or, alternatively, suspended in 5 ml of the sterile PHI-I combined medium also described in Example 4 on page 26 of WO 98/32326. In either case 5 ml of 100 mM 3'-5'-Dimethoxy-4' hydroxyacetophenone is also added. PHI-A basic medium at pH 5.2 comprises 4 g/l of CHU(N6) basal salts (Sigma C-1416), 1.0 ml/l of Eriksson's vitamin mix (1000×, Sigma E-1511), 0.5 mg/l thiamine. HCl, 1.5 mg/ml of 2,4-D, 0.69 g/l L-proline, 68.5 g/l sucrose and 68.5 g/l glucose. PHI-I combined medium, also adjusted to pH 5.2 with KOH and filter sterilized, comprises 4.3 g/l of MS salts (GIBCO-BRL), 0.5 mg/ml nicotinic acid, 0.5 mg/ml pyridoxine. HCl, 1.0 mg/ml thiamine. HCL, 100 mg/l myo-inositol, 1 g/l vitamin assay casamino acids (Difco), 1.5 mg/ml of 2,4-D, 0.69 g/l L-proline, 68.5 g/l sucrose and 36 g/l glucose.

Alternatively, suspensions of *Agrobacterium* for transformation of plant material are prepared in a similar manner to described by Ishida et al (1996) Nature Biotechnology, 14, 745–750. 3×5 mm loopfuls of *Agrobacterium* are removed from plates, transferred and suspended in 5 ml of LS-inf medium. LS-inf medium (Linsmaier and Skoog, 1965, Physiol. Plant 18, 100–127) adjusted to pH 5.2 with KOH contained LS major and minor inorganic salts, 0.5 mg/ml nicotinic acid, 0.5 mg/ml pyridoxine. HCl, 1.0 mg/ml thiamine. HCL, 100 mg/l myo-inositol, 1 g/l vitamin assay casamino acids (Difco), 1.5 mg/ml of 2,4-D, 68.5 g/l sucrose and 36 g/l glucose.

However produced, the suspension of *Agrobacterium* is vortexed to make an even suspension and the cell population adjusted to between $0.5 \times 10^9$ and $2 \times 10^9$ cfu/ml (preferably the lower). $1 \times 10^9$ cfu/ml corresponds to an OD (1 cm) of ~0.72 at 550 nm.

*Agrobacterium* suspensions are aliquoted into 1 ml lots in sterile 2 ml microcentrifuge tubes and used as soon as possible Corn Lines for Transformation Suitable maize lines for transformation include but are not restricted to, A188, F1 P3732, F1 (A188×B73Ht), F1 (B73Ht×A188), F1 (A188×BMS). Varieties A188, BMS (Black Mexican Sweet) and B73 Ht are obtained from the Ministry of Agriculture, Forestry and Fisheries, which is well known to the skilled man. P3732 is obtained from IWATA RAKUNOU KYODOKUMIAI. Suitable maize lines also include a variety of A188× inbred crosses (e.g PHJ90×A188, PHN46×A188, PHPP8×A188 in table 8 of WO98/32326) as well as elite inbreds from different heterotic groups (e.g PHN46, PHP28 and PHJ90 in table 9 of WO98/32326).

For example immature embryos are produced from "Hi-II" corn. "Hi-II" is a hybrid between inbreds (A188×B73) generated by reciprocal crosses between Hi-II parent A and Hi-II parent B available from the Maize Genetic Cooperation Stock Center, University of Illinois at Champaign, Urbana, Ill.). Seeds, termed 'Hi-II' seeds obtained from these crosses are planted out in a greenhouse or field. The resulting Hi-II plants are self or cross-pollinated with sister plants.

Preparation of Immature Embryos, Infection and Co-cultivation

Transformation of immature embryos of corn is carried out by contacting the immature embryos with the suitable recombinant strains of *Agrobacterium* described above. An immature embryo means the embryo of an immature seed which is in the stage of maturing following pollination. Immature embryos are an intact tissue that is capable of cell division to give rise to callus cells that can then differentiate to produce the tissues and organs of a whole plant. Preferred material for transformation also includes the scutella of embryos which is also capable of inducing dedifferentiated calli with the ability to regenerate normal fertile plants having been initially transformed. Preferred material for transformation thus also includes callus derived from such dedifferentiated immature zygotic embryos or scutella.

Immature corn embryos are isolated aseptically from developing ears as described by Green and Phillips (1976, Crop. Sci. 15: 417–421) or, alternatively, by the methods of Neuffer et al (1982, "Growing Maize for genetic purposes" in *Maize for biological research,* W. F. Sheridan ed., University Press, University of North Dakota, Grand Forks, N. Dak., USA). For example, immature corn embryos between 1–2 mm (preferably 1–1.2 mm) long are aseptically isolated from female spikes at 9–12 (preferably 11) d after pollination using a sterile spatula. Typically ears are surface sterilised with 2.63% sodium hypochlorite for 20 min before washing with sterile deionized water and aseptic removal of immature embryos. Immature embryos (preferably ~100 in number) are dropped directly into a 2 ml microcentrifuge tube containing about 2 ml of the same medium as used for preparing the suspension of *Agrobacterium* (the alternatives for which are described above). The cap of the tube is closed and the contents mixed by vortexing for a few seconds. The medium is decanted off, 2 ml of fresh medium are added and vortexing is repeated. All of the medium is then drawn off to leave the washed immature embryos at the bottom of the tube.

Having prepared the immature maize embryos the next phase of the process, the infection step, is to contact them in with the transformed strain of *Agrobacterium.*

In one example of this process, the infection step takes place in a liquid medium which includes the major inorganic salts and vitamins of N6 medium (1987, Chu C. C. Proc. Symp. Plant Tissue Culture, Science Press Peking. Pp 43–50) as described in example 4 of WO 98/32326. 1.0 ml of suspension of *Agrobacterium* , prepared as described above in PHI-A medium is added to the embryos in the microcentrifuge tube and vortexed for about 30s. Alternatively, 1.0 ml of suspension of *Agrobacterium* prepared, also as described above, in either PHI-I medium or in LS-inf medium is added.

After standing for 5 minutes the suspension of *Agrobacterium* and embryos is poured out into a Petri plate containing either 1) PHI-B medium or 2) PHI-J medium or 3) LS-AS medium according to whether the original suspension of *Agrobacterium* had been prepared in PHI-A medium, PHI-I medium or LS-inf medium, respectively. The *Agrobacterium* suspension is drawn off using a Pasteur pipette, the embryos manipulated so that they sit axis-side downwards onto the medium, the plate sealed with parafilm and incubated in the dark at 23–25 C. for 3 days of cocultivation. PHI-B medium at pH 5.8 comprises 4 g/l of CHU(N6) basal salts (Sigma C-1416), 1.0 ml/l of Eriksson's vitamin mix (1000×, Sigma E-1511), 0.5 mg/l thiamine. HCl, 1.5 mg/ml of 2,4-D, 0.69 g/l L-proline, 0.85 mg/l silver nitrate, 30 g/l sucrose, 100 μM acetosyringone and 3 g/l gelrite (Sigma). PHI-J medium, also adjusted to pH 5.8 comprises 4.3 g/l of MS salts (GIBCO-BRL), 0.5 mg/ml nicotinic acid, 0.5 mg/ml pyridoxine. HCl, 1.0 mg/ml thiamine. HCL, 100 mg/l myo-inositol, 1.5 mg/ml of 2,4-D, 0.69 g/l L-proline, 20 g/l sucrose, 10 g/l glucose, 0.5 g/l MES (Sigma), 100 mM acetosyringone and 8 g/l purified agar (Sigma A-7049). LS-AS medium (Linsmaier and Skoog, 1965, Physiol. Plant 18, 100–127) adjusted to pH 5.8 with KOH contains LS major and minor inorganic salts, 0.5 mg/ml nicotinic acid, 0.5 mg/ml pyridoxine. HCl, 1.0 mg/ml thiamine. HCL, 700 mg/l L-proline, 100 mg/l myo-inositol, 1.5 mg/ml of 2,4-D, 20 g/l sucrose, 10 g/l glucose, 0.5 g/l MES, 100 mM acetosyringone and 8 g/l purified agar (Sigma A-7049).

Following the preparation of immature embryos, as described above, an alternative method of achieving transformation is to infect them during and after a period of dedifferentiation as described in U.S. Pat. No. 5,591,616. Immature embryos are placed on LSD 1.5 solid medium containing LS inorganic salts and vitamins along with 100 mg/ml casamino acids, 700 mg/l L-proline, 100 mg/l myo-inositol, 1.5 mg/ml of 2,4-D, 20 g/l sucrose and 2.3 g/l of gelrite. After 3 weeks at 25 C., calli originating from the scutella are collected in a 2 ml microcentrifuge tube and immersed in 1 ml of *Agrobacterium* suspension prepared, as described above, in AA medium. After standing for 5 minutes, the resultant calli are transferred to 2N6 solid medium containing 100 mM acetosyringone and incubated in the dark at 25 C. for a 3 day period of cocultivation. 2N6 solid medium comprises the inorganic salts and vitamins of N6 medium (Chu C. C., 1978; Proc. Symp. Plant Tissue Culture, Science Press Peking, pp 43–50) containing 1 g/l casamino acids, 2 mg/l 2,4-D, 30 g/l sucrose and 2 g/l of gelrite.

'Resting and Selection of Transformants'

Following cocultivation, embryos are, optionally, transferred to a plate containing PHI-C medium, sealed over with parafilm and incubated in the dark for 3 days for a 'resting step' prior to selection. PHI-C medium at pH 5.8 comprises 4 g/l of CHU(N6) basal salts (Sigma C-1416), 1.0 ml/l of Eriksson's vitamin mix (1000×, Sigma E-1511), 0.5 mg/l thiamine. HCl, 1.5 mg/ml of 2,4-D, 0.69 g/l L-proline, 0.85 mg/l silver nitrate, 30 g/l sucrose, 0.5 g/l MES, 100 mg/l carbenicillin and 8 g/l purified agar (Sigma A-7049). As disclosed in WO 98/32326, the desirability of including this resting step in the overall transformation process varies according to corn line and is a matter of experiment.

For the selection step, about 20 embryos are transferred onto each of a number of fresh plates containing PHI-D selection medium or LSD 1.5 selection medium, sealed with parafilm and incubated in the dark at 28 C. PHI-D selection medium, adjusted to pH 5.8 with KOH, comprises 4 g/l of CHU(N6) basal salts (Sigma C-1416), 1.0 ml/l of Eriksson's vitamin mix (1000×, Sigma E-1511), 0.5 mg/l thiamine. HCl, 1.5 mg/ml of 2,4-D, 0.69 g/l L-proline, 0.85 mg/l silver nitrate, 30 g/l sucrose, 0.5 g/l MES, 100 mg/l carbenicillin, 8 g/l purified agar (Sigma A-7049) and between 0.1 mM and 20 mM of tissue culture grade N-(Phosphonomethyl)-glycine (Sigma P-9556). LSD 1.5 selection medium, adjusted to pH 5.8 with KOH, comprises LS major and minor inorganic salts (Linsmaier and Skoog, 1965, Physiol. Plant 18, 100–127), 0.5 mg/ml nicotinic acid, 0.5 mg/ml pyridoxine. HCl, 1.0 mg/ml thiamine. HCL, 700 mg/l L-proline, 100 mg/l myo-inositol, 1.5 mg/ml of 2,4-D, 20 g/l sucrose, 0.5 g/l MES, 250 mg/l cefotaxime, 8 g/l purified agar (Sigma A-7049) and between 0.1 mM and 20 mM of tissue culture grade N-(Phosphonomethyl)-glycine (Sigma P-9556).

Alternatively, in the case that the starting material for selection are calli-derived from immature embryos as disclosed in WO 5591616 then such calli are washed with sterilised water containing 250 mg/l cefotaxime before culturing on LSD 1.5 selection medium.

The embryos or clusters of cells that proliferate from the immature embryos are transferred (if necessary using a sterile scalpel) to plates containing fresh selection medium at 2 weekly intervals over a total period of about 2 months. Herbicide-resistant calli are then bulked by continued growth on the same medium until the diameter of the selected callus exceeds about 1.5 cm The concentration of N-(Phosphonomethyl)-glycine in the selection medium is chosen appropriately to select a desirable number of genuine transformants and is preferably within the range 0.3–5 mM. Preferably the concentration of N-(Phosphonomethyl)-glycine used in the selection medium is about 1 mM for the first two weeks of selection and about 3 mM thereafter.

Regeneration of Transformants/Propagation and Analysis of Transformed Plant Material The selected calli are regenerated into normal fertile plants according to, for example, the methods described by Duncan et al (1985, Planta, 165, 322–332) by Kamo et al (1985, Bot. Gaz. 146(3), 327–334) and/or by West et al (1993, The Plant Cell, 5, 1361–1369) and/or by Shillito et al (1989) Bio/Technol. 7, 581–587.

For example, selected calli of diameter 1.5–2 cm are transferred to regeneration/maturation medium and incubated in the dark for about 1–3 weeks to allow the somatic embryos to mature. A suitable regeneration medium, PHI-E medium (WO 98/32326) is adjusted to pH 5.6 with KOH and comprises 4.3 g/l of MS salts (GIBCO-BRL), 0.5 mg/ml nicotinic acid, 0.5 mg/ml pyridoxine. HCl, 0.1 mg/ml thiamine. HCL, 100 mg/l myo-inositol, 2 mg/l glycine, 0.5 mg/l zeatin, 1.0 mg/ml of indoleacetic acid, 0.1 mM abscisic acid, 100 mg/l carbenicillin, 60 g/l sucrose, 8 g/l purified agar (Sigma A-7049) and, optionally, between 0.02 mM and 1 mM of tissue culture grade N-(Phosphonomethyl)-glycine (Sigma P-9556).

The calli are then transferred to rooting/regeneration medium and grown at 25 C. under either a schedule of 16 h daylight (270 mE m$^{-2}$s$^{-1}$) and 8 h of darkness or under continuous illumination (~250 mE m$^{-2}$s$^{-1}$) until such a time as shoots and roots develop. Suitable rooting/regeneration media are either LSZ medium as described in the following paragraph (optionally containing no phosphonomethylglycine) or PHI-F medium at pH 5.6 which comprises 4.3 g/l of MS salts (GIBCO-BRL), 0.5 mg/ml nicotinic acid, 0.5 mg/ml pyridoxine. HCl, 0.1 mg/ml thiamine. HCL, 100 mg/l myo-inositol, 2 mg/l glycine, 40 g/l sucrose and 1.5 g/l gelrite.

Alternatively, selected calli are transferred directly to LSZ regeneration medium adjusted to pH 5.8 with KOH and comprising LS major and minor inorganic salts (Linsmaier and Skoog, 1965, Physiol. Plant 18, 100–127), 0.5 mg/ml nicotinic acid, 0.5 mg/ml pyridoxine. HCl, 1.0 mg/ml thiamine. HCL, 700 mg/l L-proline, 100 mg/l myo-inositol, 5 mg/ml of zeatin, 20 g/l sucrose, 0.5 g/l MES, 250 mg/l cefotaxime, 8 g/l purified agar (Sigma A-7049) and, optionally, between 0.02 mM and 1 mM of tissue culture grade N-(Phosphonomethyl)-glycine (Sigma P-9556) is used. After a period of incubation in the dark plates are subject to illumination (continuous or light/day as above)and plantlets regenerated.

Small plantlets are transferred to individual glass tubes containing either PHI-F medium or half strength LSF medium at pH 5.8 comprising LS major salts (Linsmaier and Skoog, 1965, Physiol. Plant 18, 100–127) at half strength, LS minor salts, 0.5 mg/ml nicotinic acid, 0.5 mg/ml pyridoxine. HCl, 1.0 mg/ml thiamine. HCL, 100 mg/l myo-inositol, 20 g/l sucrose, 0.5 g/l MES, 8 g/l purified agar (Sigma A-7049) and grown on for about another week. Plantlets are then transferred to pots of soil, hardened off in a growth chamber (85% relative humidity, 600 ppm $CO_2$ and 250 mE $m^{-2}s^{-1}$) and grown to maturity in a soil mixture in a greenhouse.

The first (T0) generation of plants obtained as above are self fertilised to obtain second generation (T1) seeds. Alternatively (and preferably) the first generation of plants are reciprocally crossed with another non-transgenic corn inbred line in order to obtain second generation seeds. The progeny of these crosses (T1) are then expected to segregate 1:1 for the herbicide resistance trait. T1 seeds are sown, grown up in the glass house or field and the level of resistance, inheritance of resistance and segregation of resistance to the herbicide glyphosate through this and subsequent generations assessed by the observation of differential plant survival, fertility, and symptoms of necrosis in tissue following spray treatment of with glyphosate (suitably formulated and, optionally, as a salt) at a range of rates between 25 and 2000 g/ha and at a range of growth stages between and including V2 and V8 (or, alternatively, at 7–21 days post germination). These assessments are made relative to susceptible segregants and relative to similar, untransformed lines of corn which do not comprise genes of the present invention or prior at sequences capable of conferring resistance to glyphosate. Transgenic lines which exhibit resistance to glyphosate are selected and again selfed or backcrossed to a non-transgenic inbred.

At all stages in the above process tissue samples of transformed callus, plantlets, T0 and T1 plant material are optionally taken and analysed by 1) Southerns and PCR in order to indicate the presence, copy number and integrity of transgenes, 2) Northern (or similar) analysis in order to measure expression of mRNA from transgenes, 3) quantitative Western analysis of SDS gels in order to measure expression levels of EPSPS and 4) measurement of EPSPS enzyme activity levels in the presence and absence of glyphosate in order to assess more accurately how much of the EPSPS which is expressed derives from the transgene.

Such methods of analysis are well known in the art. Suitable methods to test for the presence, integrity and expression of the transgene by PCR, for carrying out Southern analysis, for the cloning and expression of mature rice EPSPS in *E. coli*, for the purification of rice EPSPS, for the generation of polyclonal antibodies to purified rice EPSPS, for Western analysis of EPSPS levels in callus and in plant tissues and for the measurement of EPSPS activity levels in plant-derived extracts at a concentration of glyphosate which discriminates between the endogenous glyphosate-susceptible EPSPS and the glyphosate-resistant product of the EPSPS-encoding transgene are described in more detail below in Examples 17–20.

Table 2 Transgene Expression in Calli Originating from Transformation of Immature Embryos of A188×B73 (Hi-II) Corn with *Agrobacterium* Strain LBA4404 Containing a Superbinary Vector Carrying the EPSPS Expression Cassettes of Bluescript Vectors (pZEN 11, 12, 14 or 15) within the T-DNA Borders The table shows EPSPS enzyme assay (+/−100 $\mu$M glyphosate at 100 $\mu$M PEP) results based upon enzyme assays of extracts of stably transformed callus of regenerable A188×B73 regenerable corn, transformed using *Agrobacterium* containing a superbinary vector carrying the EPSPS expression cassettes of the pZEN11, ZEN12, ZEN14 or ZEN15 Bluescript plasmids. Each callus line represents a single event which is assayed in duplicate. The ratio of the true (allowing for ~8% inhibition) tolerant enzyme activity expressed by the transgene to endogenous susceptible activity (>98% inhibited+glyphosate) is calculated. The mutant EPSPS is expressed relatively strongly in some lines, notably lines 5 and 12, where, allowing for the reduced Vmax of the tolerant enzyme relative to the w/t (about a third) it can be estimated that the tolerant enzyme is expressed at 2–6× the normal level of the endogenous EPSPS (this calculation is complicated by the fact that, in some selected calli, expression of the transgene occurs alongside an apparent ~2–2.5×increase in the background expression of the susceptible endogenous enzyme).

| Event. Line # | DNA Construct | Measured activity (nmol/min/mg) + 100 uM glyphosate (true tolerant activity = measured × 1.08) | Total Activity (nmole/min/ mg) in absence of glyphosate | Ratio of sensitive/ true tolerant EPSPS activity |
|---|---|---|---|---|
| 1 | ZEN15 | 3.4 | 22.69 | 6:1 |
|   |       | 2.5 | 21.72 |     |
| 5 | ZEN15 | 6.6 | 21.72 | 1.9:1 |
|   |       | 7.7 | 23.94 |       |
| 7 | ZEN14 | 5.11 | 18.13 | 2.8:1 |
|   |       | 4.8  | 22.33 |       |
| 10 | ZEN14 | 6.89 | 28.13 | 2.7:1 |
|    |       | 7.17 | 29.13 |       |
| 12 | ZEN11 | 20.31 | 50.16 | 1.6:1 |
|    |       | 16.63 | 53.66 |       |
| 13 | ZEN11 | 4.54 | 20.92 | 3:1 |
|    |       | 5.31 | 21.57 |     |
| 14 | ZEN12 | 3.74 | 22.44 | 6:1 |
|    |       | 2.55 | 23.64 |     |
| 15 | ZEN12 | 12.74 | 39.79 | 2:1 |
|    |       | 11.40 | 39.13 |     |
| 21 | control | 0.0 | 11.85 | — |
|    |         | 0.1 | 12.29 |   |
| 22 | control | −0.5 | 11.59 | — |
|    |         | −.02 | 11.97 |   |

EXAMPLE 12

Transformation of Corn Lines by Bombardment with Particles Coated with DNA Which Includes an EPSPS Expression Cassette; Selection and Regeneration of Plant Cells and Plants Which are Resistant to Glyphosate In a further example, friable embryogenic callus derived from immature maize embryos is initiated on a solid medium and transformed biolistically. Similar to the process described in example 11, transformed callus is then selected on the basis of differential growth rate in medium containing a range of concentrations of glyphosate. Resistant callus is selected and regenerated to provide To plantlets which are transferred to pots, grown to maturity and self or cross fertilised in the glasshouse. The progeny seed (T1) are then grown up to provide further generations of plants which are assessed for resistance to glyphosate and analysed for transgene presence, integrity and expression as described in example 11.

Initiation of Callus from Immature Embryos

Friable embryogenic Type II callus suitable for transformation is derived from immature embryos of, for example, A188×B73 corn. Alternative inbred such as B73-derived and hybrid lines of corn can be also used including, for example, those listed in Example 11. Immature embryos of maize between 1–2 mm long are isolated aseptically from female spikes at, typically, about 11 d after pollination using the methods indicated in example 11.

Immature embryos are plated onto, for example, onto a N6-based medium (Chu et al, 1975, Scientia Sinica, 18, 659–668) adjusted with KOH to pH 5.8 containing 1 mg/l 2,4-D, 2.9 g/l L-proline, 2 mg/l L-glycine, 100 mg/l of casein hydrolysate, N6 major salts, N6 minor salts, N6 vitamins, 2.5 g/l gelrite (or 2 g/l 'Gelgro') and 20 g/l sucrose. Alternative suitable media include, for example, a similar medium but containing MS salts (Murashige and Skoog, 1962, Physiol. Plant, 15, 473–497) in place of N6 salts. Alternatively, the medium may contain ~10 mg/l dicamba in place of 2,4-D.

Immature embryos are incubated in the dark on the above medium at ~25 C. in order to initiate callus. Type II callus material is selected by visual selection of fast growing friable embryogenic cells by methods known in the art and as described for example in WO 98/44140. For example, suitable recipient cells are selected manually by choosing preferred cells which may be at the surface of a cell cluster and further identifiable by their lack of differentiation, small size and high nucleus/cytoplasm volume ratio. A suspension culture is initiated from tissue within the callus which appears the least differentiated, softest and most friable. Tissue with this morphology is transferred to fresh plates of media about 8–16 d after the initial plating of the immature embryos. The tissue is then routinely subcultured every 14–21 d by taking on ~10% of pieces which reach approximately a gram. At each step only material with the desired type II or type III morphology is subcultured on.

Preparation of Cell Suspension Cultures

Preferably within 6 months of the above-described callus initiation, dispersed suspension cultures are initiated in liquid media containing suitable hormones such as 2,4-D and NAA optionally supplied in the form of slow-release hormone capsule treatments as described for example in examples 1 and 2 of U.S. Pat. No. 5,550,318. Optionally, hormone levels within the cultures are maintained by occasional spiking with fresh hormone supplement. Suspension cultures are initiated, for example, by adding approximately 0.5 g of callus tissue to a 100 ml flask containing 10 ml of suspension culture medium. Every 7 days, the culture is further subcultured by transferring, by use of a sterile wide-ended pipette, 1 ml of settled cells and 4 ml of conditioned medium to a fresh flask containing fresh medium. Large aggregates of cells unable to pass through the pipette tip are excluded at each subculturing step. Optionally, suspension cultures are passed through a suitable sieve (e.g. ~0.5–1.0 mm mesh) at each subculturing step. After 6–12 weeks the culture becomes dispersed. Suitable cell suspension culture media include for example, a medium adjusted to pH 6.0 containing Murashige and Skoog (1962) major and minor salts (optionally modified to contain a reduced level, 1.55 g/l, of ammonium nitrate), 30 g/l sucrose, 0.25 mg/l thiamine, 10 mg/l dicamba, 25 mM L-proline, 200 mg/l casein hydrolysate, 100 mg/l myo-inositol, 500 mg/l potassium sulphate and 400 mg/l potassium hydrogen phosphate. Alternatively, in place of dicamba, cell suspension medium contains a 2,4-D and/or NAA.

Cryopreservation of Cell Suspension Cultures

Optionally, suspension cultures obtained as described above, are cryopreserved using cryoprotectants and methods described for example in example 2 of U.S. Pat. No. 5,550,318. Cryopreservation entails adding cryoprotectant at ice temperature to pre-cooled cells, also at ice temperature, in a stepwise manner over a period of one to two hours. The mixture is maintained at ice temperature and the eventual volume of cryoprotectant is equal to the volume of cell suspension. The final concentrations of cryoprotectants are, for example, 10% dimethylsulfoxide, 10% polyethylene glycol (6000 Mw), 0.23 M L-proline and 0.23 M glucose. After a 30 min period of equilibration at ice temperature the mixture is divided into ~0.5 ml aliquots, transferred to 2 ml microcentrifuge tubes, and cooled slowly at a rate of 0.5 C./min down to a temperature of −8 C. Following a period for ice nucleation, the sample is further cooled slowly down to −35 C. and then plunged into liquid nitrogen. When required for use, frozen samples are thawed by first bathing them in their containers in water at ~40 C. for 2 min and then allowing them to slowly thaw completely. The mixture of cells and cryoprotectants is then pipetted onto a filter laid over a layer of BMS 'feeder' cells at 25 C. Once the thawed tissue begins to grow it is transferred back to fresh solid culture medium and, once established (within 1 to 2 weeks) is further transferred into cell suspension culture medium. Once growth in liquid suspension culture is re-established the cells are used for transformation.

Particle-mediated Transformation

Plasmid pIGPD9-derived DNA (FIG. 12) containing Xma1 EPSPS expression cassettes (i.e. pZEN9i, ZEN11i, ZEN12i, ZEN14i etc.) is purified, bulked up (e.g by anion exchange chromatographic or $CsCl_2$ gradient densitometric isolation of plasmid DNA from cells of a suitable HisB-, Rec A-host strain of *E.coli* (e.g. DH5α: hisB-) after growth to stationary phase in a minimal 5×A medium ($K_2HPO_4$ 52.5 g, $KH_2PO_4$ 22.5 g, $(NH_4)_2SO_4$ 5 g and sodium citrate.$2H_2O$ 2.5 g per liter) and provided as a concentrated solution (preferably ~1 mg/ml) in sterile water. DNA is provided as a circular plasmid DNA or, alternatively is restricted with Xma 1 to provide a linear EPSPS-expression cassette-containing fragment and used following purification by agarose gel electrophoresis and electroelution.

Suitable apparatus for bombardment is, for example, the Biorad PDS 1000 Helium gun. The dish is placed 5–6 cm below the stopping screen used to stop the capton macro-projectile. The DNA construct is precipitated onto tungsten or gold particles with an average diameter of ~1.0 μm in a similar manner to that described by Klein et al 1987, Nature, 327, 70–73. For example, 1.25 mg of tungsten or gold particles (pre-washed in ethanol at 65 C. for 12 h) are mixed, in successive order, with ~20–30 mg of DNA, 1.1 M $CaCl_2$ and 8.7 mM spermidine to a final volume of ~0.6 ml. The mixture is vortexed for 10 min at 0–4 C., subject to low speed centrifugation (~500 g) for 5 min and the bulk of the supernatant decanted off to leave the tungsten particles suspended in a final volume of ~30 ml. 1–10 μl aliquots are pipetted onto the macroprojectile of the particle gun.

Suspension cultures derived from type II and/or type II callus are maintained in culture for 3–5 months (or, alternatively, recovered from cryopreservation), freshly subcultured and then sieved through a ~0.5–1.0 mm stainless steel mesh. Approximately 0.5 ml packed cell volume of cells recovered from the filtrate is then pipetted onto 5 cm paper filters and vacuum dried before transfer to a petri dish containing a stack of three 7 cm paper filters moistened with suspension culture medium. Each plate of suspension cells is centred onto the sample plate tray, the petri dish lid removed and bombarded twice at a vacuum of 28 inches of mercury. 0.1 or 1.0 mm screens are placed about 2.5 cm below the stop plate in order to ameliorate injury to the bombarded tissue. After bombardment the plant cells are removed from the filter, resuspended back into cell suspension culture medium and cultured for 2–21 days. Alternatively, the bombarded callus is transferred, plate to plate, onto to a plate containing a similar solid medium (for example containing 8 g/l of purified agar) and similarly cultured at ~25 C. in the dark.

Selection of Transformants

Following transformation, cells growing unselected in liquid or solid culture are transferred to filters and overlayed onto solid medium containing a range (0.1–20 mM) of selecting concentrations of tissue culture grade N-(phosphonomethyl) glycine (Sigma). Suitable solid selection media include media, adjusted to pH 5.8 or 6.0 with KOH, containing either MS or N6 salts (such as those described above for callus initiation or, with suitable addition of agar, those described above for growth of cells in liquid suspension) and N-(phosphonomethyl) glycine. Suitable selection media also include, for example, the selection media described in example 11 but, in this case, modified so as to lack antibiotics. Transformed calli expressing the resistant EPSP synthase enzyme are selected on the basis of their growth at concentrations inhibitory to similar preparations of untransformed cells. Growing clumps are subcultured on to fresh selective medium. Preferably the concentration of N-(Phosphonomethyl)-glycine used in the selection medium is about 1 mM for the first two weeks of selection and about 3 mM thereafter. After 6–18 weeks putative resistant calli are identified and selected.

Regeneration of Transformants/Propagation and Analysis of Transformed Plant Material The selected calli are regenerated into normal fertile plants according to, for example, the methods described by Duncan et al (1985, Planta, 165, 322–332) by Kamo et al (1985, Bot. Gaz. 146(3), 327–334) and/or by West et al (1993, The Plant Cell, 5, 1361–1369) and/or by Shillito et al (1989) Bio/Technol. 7, 581–587.

For example, plants are efficiently regenerated by transferring the embryogenic callus to Murashige and Skoog medium adjusted to pH 6.0 containing 0.25 mg/l 2,4-D, 10 mg/l 6-benzyl-aminopurine and, optionally, 0.02 to 1 mM N-(phosphonomethyl) glycine. After ~2 weeks tissue is transferred to a similar medium but lacking hormones. Optionally the hormone level is decreased step wise through more transfers and over a longer period of time up to 6–8 weeks. Shoots which develop after 2–4 weeks are transferred to MS medium containing 1% sucrose and solidified with 2 g/l Gelgro into which they then root.

Alternatively methods and media used for regeneration are as in example 1 except that the media used do not contain antibiotic.

Methods for growing plants to maturity, for the further propagation of plants through generations, for analysis of the inheritance of resistance to glyphosate and for analysis of the presence, integrity and expression of the EPSPS transgene are as described in example 11.

EXAMPLE 13

Transformation of Corn Lines with DNA Which Includes an EPSPS Expression Cassette Coated onto Silicon Carbide Whiskers; Selection and Regeneration of Plant Cells and Plants Which are Resistant to Glyphosate In a further example, maize lines including, for example, hybrid lines having the genotype A188×B73 are prepared as cell suspensions and transformed by contacting the cells with silicon carbide whiskers coated with DNA using methods essentially as described by Frame et al (1994, Plant J. 6, 941–948). As described in the previous examples, the transformed callus so generated is selected on the basis of differential growth rate in medium containing a range of concentrations of glyphosate, regenerated into plantlets (To) which are grown to maturity and either self or cross fertilised to provide progeny seed (T1) for further breeding. Plants and plant material is assessed for resistance to glyphosate and analysed for transgene presence, integrity and expression as described in the previous examples.

Initiation of Callus from Immature Embryos, Preparation of Cell Suspension Cultures Maize cell suspensions suitable for transformation are optionally cryopreserved and provided in the same manner as described in example 12

Transformation

Plasmid pIGPD9-derived DNA (FIG. 12) containing Xma1 EPSPS expression cassettes (i.e. pZEN9i, ZEN11i, ZEN12i, ZEN14i etc.) is purified, bulked up (e.g by anion exchange chromatographic or $CsCl_2$ gradient densitometric isolation of plasmid DNA from cells of a suitable HisB-, Rec A-host strain of *E.coli* (e.g. DH5αc: hisB-) after growth to stationary phase in a minimal 5×A medium ($K_2HPO_4$ 52.5 g, KH$_2$PO$_4$ 22.5 g, (NH$_4$)2SO$_4$ 5 g and sodium citrate.2H$_2$O 2.5 g per liter) and provided as a concentrated solution (preferably ~1 mg/ml) in sterile water. DNA is provided as a circular plasmid DNA or, alternatively is restricted with Xma 1 to provide a linear EPSPS-expression cassette-containing fragment an used following purification by agarose gel electrophoresis and electroelution.

Transformation is carried out exactly as described by Frame et al 1994. Alternatively the procedure is somewhat modified as described below.

Cells grown in liquid culture in cell suspension medium one day after subculturing are allowed to settle out in a shake flask. Spent medium is decanted and drawn off and 12 ml of N6 medium at pH 6.0 (Chu et al 1975) modified to contain 6 mM L-proline, 20 g/l sucrose, 2 mg/l 2,4-D, 0.25 M sorbitol and 0.25M mannitol is added per 4 ml packed cell volume. The flask is returned to the shaker (rotary shaken at 125 rpm and incubated at 26–28 C.) for 45 min. At the end of this period 1 ml aliquots of cell suspension are removed, using a wide bore pipette, into a series of sterile microcentrifuge tubes. After allowing the cells in each tube to settle out, 0.6 ml of the spent medium supernatant is then removed to leave most of the remaining content as settled cells. 50 mg of silicon carbide whiskers (Silar SC-9 whiskers, Advanced Composite Materials Corp., Greer, S.C. USA) are suspended by vortexing in 1 ml of the modified N6 medium described above. 40 ml of these suspended whiskers and 25 mg of the plasmid or linear DNA including the EPSPS expression cassette are then added to each tube of settled cells. The tubes are finger vortexed 2–3 times, mixomated (in a Mixomat dental amalgam mixer (Degussa, Ontario, Canada) for 1 second and then 0.3 ml of N6 medium (modified as described above) is added to each microcentrifuge tube. The suspended cells are then plated (200 µl/plate)out onto a filter disc overlying solid N6 medium (the same as the modified N6 medium described above but lacking sorbitol, lacking mannitol and containing 30 g/l sucrose and 3 g/l of gelrite). Each plate is then wrapped with Urgopore tape (Stelrico, Brussels) and left to incubate in the dark for 1 week at 26–28 C.

Selection of Transformants

Transformed callus is selected as described in example 12 or, alternatively, as described in Frame et al 1994 except that N-(phosphonomethyl)glycine is used, at a range of concentrations between 1 and 5 mM in place of the bialaphos specified in the Frame et al publication.

Regeneration of Transformants/Propagation and Analysis of Transformed Plant Material Plants are regenerated, propagated, and bred as described in example 12. Plants are analysed for resistance to glyphosate and plant material is analysed for transgene presence, integrity and expression as described in example 12.

EXAMPLE 14

Transformation of Rice Lines Using an Agrobacterium Strain Containing a Superbinary Vector Which Includes an EPSPS Expression Cassette Between the Right and Left Borders of the T-DNA; Selection and Regeneration of Plant Cells and Plants Which are Resistant to Glyphosate In a further example, scutella are isolated from mature seeds of suitable lines of rice (including, for example, varieties Koshihikari, Tsukinohikari and Asanohikari) dedifferentiated and the callus thus-obtained transformed by infection with Agrobacterium. Following selection and regeneration, transgenic plantlets (To) are obtained which are grown to maturity and either self or cross fertilised to provide progeny seed (T1) for further breeding. Plants and plant material are assessed for resistance to glyphosate and analysed for transgene presence, integrity and expression as described in the previous examples. As an alternative to the methods described below the methods described in example 1 of U.S. Pat. No. 5,591,616, suitable adapted so that glyphosate rather than hygromycin is used for selection, are used.

Construction of Agrobacterium Strain; Preparation of Agrobacterium Suspension

A strain of Agrobacterium containing superbinary vector having the desired EPSPS expression cassette between the right and left borders is constructed (using electroporation to transform Agrobacterium with plasmid DNA) as described in example 1. Suspensions are prepared according to the methods described in example 1. Alternatively, the transformed strain of Agrobacterium is grown for 3 days on AB medium (Chilton et al, 1974, Proc. Natl. Acad. Sci. USA, 71, 3672–3676) containing appropriate antibiotic selection (e.g. 50 mg/l spectinomycin in the case of LBA4404 (pSB1ZEN18 etc)) and looped off of the plate to form a suspension in AAM medium (Hiei et al, 1994, The Plant Journal, 6(2), 271–282) at a density of 1–5×10$^9$ cells/ml.

Rice Cultivars, Preparation of Callus from Scutella

Rice cultivars are, for example Oryza sativa L. Tsukinohikari, Asanohikari and Koshihikari.

Mature seeds are dehusked, surface sterilized by washing in 70% ethanol and then soaked for 30 minutes in 1.5% NaOCl. After rinsing in sterile water they are cultured at 30 C., in darkness for 3 weeks on 2N6 medium at pH 5.8 which contains the major salts, minor salts and vitamins of N6 medium (Chu 1978 in Proc. Symp. Plant Tissue Culture., Peking: Science Press, pp 43–50) 30 g/l sucrose, 1 g/l casein hydrolysate, 2 mg/l 2,4-D and 2 g/l gelrite. Proliferated callus derived from the seed scutella is subcultured for 3–7 days on fresh 2N6 medium. Growing callus (1–2 mm in diameter) is selected, suspended in 2N6 liquid medium (without gelrite) and cultured in flasks, in darkness on a rotary shaker at 125 rpm and at 25 C. The medium is changed every 7 days. Cells growing in log phase after 3–4 transformations are used for transformation.

Infection, Transformation and Selection

Suspended rice callus cells are allowed to settle out of suspension and then resuspended in the suspension of Agrobacterium, left in contact for several minutes and then, again, allowed to settle out and, without rinsing, plated out onto 2N6-AS medium (2N6 medium adjusted to pH 5.2 and containing 10 g/l D-glucose and 100 mM acetosyringone) and incubated in the dark at 25 C. for 3–5 days. Growing material is rinsed throroughly with 250 mg/l cefotaxime in sterile water and then transferred onto 2N6-CH medium (2N6 medium adjusted to pH 5.8 with KOH containing 250 mg/l cefotaxime and 0.5–5 mM tissue culture grade N-(phosphonomethyl) glycine) or, alternatively, 2N6K—CH medium (2N6 medium modified as described by Hiei et al 1994 but, in place of hygromycin, containing 0.5–5 mM tissue culture grade N-(phosphonomethyl) glycine) and cultured for 3 weeks in the dark at 25 C. Proliferating colonies are subcultured onto a second plate of selective medium for a further period of 7–14 days.

Regeneration and Analysis of Plants

Growing colonies are plated onto a regeneration medium at pH 5.8 containing half strength N6 major salts, N6 minor salts, N6 amino acids, vitamins of AA medium (Chilton et al 1974), 1 g/l casein hydrolysate, 20 g/l sucrose, 0.2 mg/l napthaleneacetic acid, 1 mg/l kinetin, 3 g/l gelrite and, optionally, 0.04–0.1 mM N-(phosphonomethyl)glycine. These plates are incubated at 25 C. and kept under continuous illumination (~2000 lux). As described in example 11 regenerated plants are eventually transferred to soil in pots and matured in a greenhouse.

Plants are propagated, and bred (for example the transgenic plants are selfed) essentially as described in example 11. Plants are analysed for resistance to glyphosate and plant material is analysed for transgene presence, integrity and expression essentially as described in example 11.

EXAMPLE 15

Transformation of Wheat Lines with DNA Which Includes an EPSPS Expression Cassette by Use of Microprojectile Bombardment; Selection and Regeneration of Plant Cells and Plants Which are Resistant to Glyphosate In a further example, immature embryos are isolated from suitable lines of wheat (including, for example, spring wheat cv BobWhite, or Jaggar) incubated on hormone(2,4-D)-containing medium for 2 days and transformed by bombardment with DNA-coated particles. Following a period for recovery and continued growth of callus, callusing embryos are subcultured through a series of media containing a fixed level of glyphosate and (serially diluted) decreasing levels of 2,4-D such that somatic embryogenesis is induced. The selected material is regenerated to form shoots on a medium also containing glyphosate, transferred to rooting medium and, as in the previous maize-related examples, regenerated into plantlets (To) which are grown to maturity and either self or cross fertilised to provide progeny seed (T1) for further breeding. Plants and plant material are assessed for resistance to glyphosate and analysed for transgene presence, integrity and expression as described in the previous examples. As an alternative to the methods described below the methods described in example 1 of U.S. Pat. No. 5,631,152 are used.

Preparation of Immature Embryos

Wheat plant lines (for example spring wheat *Triticum aestivum* cv BobWhite) are grown to maturity in the greenhouse and caryopses isolated at 11–15 postanthesis. Caryopses are surface sterilised by treatment for 15 minutes in 5% NaOCl and then washed repeatedly in sterile water. Immature embryos are aseptically isolated onto 3 cm squares of nylon netting (mesh size 1.5 mm) overlying A2 medium. A2 medium adjusted to pH 5.8 is 4.32 g/l Murashige and Skoog salts, 20 g/l sucrose, 0.5 g/l L-glutamine, 2 mg/l 2,4-D, 100 mg/l casein hydrolysate, 2 mg/l glycine, 100 mg/l myo-inositol, 0.5 mg/l nicotinic acid, 0.1 mg/l thiamine.HCl and 2.5 g/l gelrite. Embryos are arranged into a solid 2.5 cm disc, comprising approx. 50 in number. Plates are sealed with leukopore tape and incubated at 25° C. in the dark for 2 days. Four hours prior to bombardment embryos are transferred onto plates containing fresh A2 medium supplemented with 36.44 g/l D-sorbitol and 36.44 g/l D-mannitol. The embryos are transferred from plate to plate by means of the nylon net upon which they sit. The embryos sit on this increased osmotic strength medium for 4 h at 25° C. in the dark before being bombarded.

Particle-mediated Transformation

Plasmid pIGPD9-derived DNA (FIG. 12) containing Xma1 EPSPS expression cassettes (i.e. pZEN9i, ZEN11i, ZEN12i, ZEN14i etc.) is purified, bulked up (e.g by anion exchange chroma tographic or $CsCl_2$ gradient densitometric isolation of plasmid DNA from cells of a suitable HisB-, Rec A-host strain of *E.coli* (e.g. DH5α: hisB-) after growth to stationary phase in a minimal 5×A medium ($K_2HPO_4$ 52.5 g, $KH_2PO_4$ 22.5 g, $(NH_4)2SO_4$ 5 g and sodium citrate.$2H_2O$ 2.5 g per liter) and provided as a concentrated solution (preferably ~1 mg/ml) in sterile water. DNA is provided as a circular plasmid DNA or, alternatively is restricted with Xma 1 to provide a linear EPSPS-expression cassette-containing fragment and used following purification by agarose gel electrophoresis and electroelution.

Particles are prepared and coated with DNA in a similar manner to that described by Klein et al 1987, Nature, 327, 70–73. Preparation of DNA-coated particles and operation of the particle gun is as described in example 2. Alternatively, the details are as follows. For example, 60 mg of gold or tungsten particles (~1.0 μm) in a microcentrifuge tube are washed repeatedly in HPLC-grade ethanol and then, repeatedly, in sterile water. The particles are resuspended in 1 ml of sterile water and dispensed into 50 μl aliquots in microcentrifuge tubes. Gold particles are stored at 4 C., tungsten particles at −20 C. 3 mg of DNA are added to each aliquot of (defrosted) particles and the tubes are vortexed at top speed. Whilst maintaining near continuous vortexing, 50 μl of 2.5M $CaCl_2$ and 20 μl of 0.1M spermidine is added. After 10 minutes of further vortexing, samples are centrifuged for 5 seconds in an eppendorf microcentrifuge, the supernatant is drawn off and the particles washed in successive additions of HPLC-grade ethanol. The particles are thoroughly resuspended in 60 μl of ethanol and then dispensed in 10 μl aliquots onto the surface of each macrocarrier to be used in the PDS1000 particle gun Components of the PDS1000 particle gun are surface sterilised by immersion in 70% ethanol and air-drying. Target plates prepared, as described above, with ~50 embryos arranged into an ~2.5 cm disc are placed 6 cm from the stopping screen. 1100 psi rupture discs are then used for bombardment. Each plate is bombarded once or twice.

Bombarded plates are sealed with pore tape and maintained at 25 C. in the dark for ~16 h. Embryos dislodged from the surface of the medium by the helium shock wave are recovered and also incubated overnight on fresh plates of the same mannitol and sorbitol-supplemented A2 medium. The bombarded embryos are then transferred to fresh plates of A2 medium and incubated for 1 week at 25 C. in the dark prior to selection.

Selection and Regeneration of Transformants

After this recovery period callusing embryos are removed from the nets and transferred to A2 2P medium (A2 medium, adjusted to pH 5.8 containing 2 mM N-(phosphonomethyl) glycine), at a density of 20 explants/plate. After one week on A2 2P medium, calli are removed to A1 2P medium (A2 medium containing only 1.0 mg/l 2,4-D and 2 mM N-(phosphonomethyl)glycine) for 2 weeks and thence to A 0.5 2P medium (A2 medium containing only 0.5 mg/l 2,4-D and 2 mM N-(phosphonomethyl)glycine) for a further two weeks. Optionally, the 2 week incubation periods are reduced to 1 week and/or the middle step of incubation on A1 2P medium is omitted. Optionally, the selecting concentration of N-phosphonomethylglycine is between 0.5 and 10 mM although 2 mM is preferred. The overall time for this period of callus induction with descending levels of 2,4-D in the medium is 2–10 weeks, preferably 3–6 weeks and most preferably ~4 weeks.

To encourage maximum shoot growth and to discourage root development the calli are then transferred to Z medium. Z medium is A2 medium but containing 10 mg/l zeatin in place of 2,4-D and also containing 0.1 mM N-(phosphonomethyl)glycine. Optionally, N-(phosphonomethyl)glycine is in the range 0.04 –0.25 mM. Regenerating calli are maintained on this medium for a period of 3 weeks before subculture, at which point well developed shoots are excised. As only one event is likely to be produced on a single callus (which represents a single embryo), the entire callus is removed to a fresh plate and maintained with the excised shoot(s) to ensure multiple clones arising from the same callus do not get counted as separate events. Calli with only partially developed shoots or without regenerating sectors are returned to Z medium for a further 3 weeks. At the end of this period non regenerating calli are discarded.

Shoots are maintained on Z medium until 4 or more well-developed leaves (extending to ~2 cm in length) have formed. The regenerating plant material is then carefully transferred to plastic tubs containing 0.5MS medium. 0.5 MS medium at pH 5.8 is 2.16 g/l of Murashige and Skoog salts, 15 g/l sucrose, 2.5 g activated charcoal, 2.5 g/l gelrite, 1 mg/l glycine, 50 mg/l myo-inositol, 0.25 mg/l nicotinic acid, 0.25 mg/l pyridoxine.HCL, 0.05 mg/l thiamine.HCl and 0.1 mM N-(phosphonomethyl)glycine (optionally 0.0–0.25 mM).

Once plants have rooted they may be potted into soil and weaned, or removed to individual glass boiling tubes containing 0.5MS (with no N-(phosphonomethyl)glycine) and 2.5 g/l charcoal. It is preferred to have charcoal present in the rooting medium to adsorb any remaining PGRs or selection chemical transferred with the plantlet, and to create a dark rooting environment thereby avoiding physiologically aberrant green roots.

Callus induction and the first week of regeneration occurs at 25° C. in the dark. The second week of regeneration occurs at low light at 25° C., then subsequent weeks at approx. 2500 lux on a 16 hour photo period.

Propagation, Breeding and Analysis of Transformed Plant Material

Methods of producing T1 and further progeny are all well known in the art and essentially as described in the previous examples. Methods for analysis of the inheritance of resistance to glyphosate and the presence, integrity and expression of transgenes are as in the previous examples.

EXAMPLE 16

Transformation of Wheat Lines with DNA Which Includes an EPSPS Expression Cassette by Electroporation of Protoplasts; Selection and Regeneration of Plant Cells and Plants which Are Resistant to Glyphosate In a further example, plasmid or linear DNA comprising an EPSPS expression cassette and identical to that used in examples 12, 13 and 15 is used for direct transformation of protoplasts of a line of wheat capable of regeneration into fertile plants (cf U.S. Pat. No. 5,231,019). Isolated protoplasts of wheat, preferably from leaf tissue or cells in culture (cf Gamborg, O. L. and Wetter, L. R., Plant Tissue Culture Methods, 1975, 11–21) are prepared at ~ca $2\times10^6$ protoplasts/ml in 0.4M mannitol at pH 5.8. To this suspension are added first, 0.5 ml of 40% w/v polyethylene glycol (PEG) of molecular weight 6000 in modified F medium (Nature (1982), 296, 72–74) at pH 5.8 and, second, 65 ml of water containing 15 mg of the desired plasmid or linear DNA and 50 mg of calf thymus DNA. The mixture is incubated together for 30 min at 26 C., occasionally agitated and subsequently diluted into F medium (Nature (1982), 296, 72–74). The protoplast are isolated by low-speed centrifugation, taken up in 4 ml of CC. culture medium (Potrykus, Harms, Lorz, (1979) Theor. Appl. Genet., 54, 209–214) and incubated in the dark at 24 C.

Alternatively, and in addition to treatment with PEG, transformation of cereal protoplasts is carried out using further steps of heat shock and/or electroporation (Neumann, E. et al (1982), the EMBO J., 7, 841–845). Thus, for example, wheat protoplasts are incubated in an aqueous solution of DNA and mannitol, heated to 45 C. for 5 min and then cooled to 0 C. over a period of 10 seconds. Then polyethylene glycol is added (Mr 3K -8K) until the final concentration is ~8% w/v. After gentle but thorough mixing treatment is carried out in an electroporator. The chamber of a Dialog 'Porator' (Dialog, Dusseldorf, Germany) is sterilised by washing with 70% ethanol and then drying in sterile air. Suspensions of protoplasts (~ca $2\times10^6$ protoplasts/ml in 0.4M mannitol+the DNA) are adjusted with manganese chloride to a measured electrical resistance of ~1.4 k ohm. Samples of volume ~0.4 ml are subjected, at 10 second intervals, to three pulses of applied voltages of between 1000 and 2000 V. The, thus transformed protoplasts are then collected and diluted back out into CC culture medium.

Those skilled in the art will recognise that many permutations and variations of these transformation procedures are possible and that, for example, transformation may also be improved by raising the pH to 9.5 and/or increasing the concentration of calcium ions in the solution within which transformation is carried out.

After 3–14 days aliquots of the developing cell cultures are transferred to medium containing alternative selecting concentrations of tissue-culture grade N-(phosphonomethyl) glycine (Sigma) between 1 and 5 mM (preferably 2 mM). Resistant cell colonies so identified (exhibiting growth on concentrations of glyphosate at least 2 fold greater than tolerated by untransformed controls) are transferred to fresh agar medium also containing a range of selecting concentrations of glyphosate and, as described, in example 15, subcultured between plates containing successively declining concentrations of 2,4-D. Growing resistant colonies may be analysed (by PCR etc) for the presence of the recombinant DNA. It may or may not be possible to effect much selection at the callus step. In any case all growing calli will be taken forward.

Growing calli are then transferred to shoot regeneration medium containing zeatin and N-(phosphonomethyl)glycine and thence to rooting medium exactly as described in example 15. Fertile transgenic plants expressing glyphosate-resistant EPSP synthase are then regenerated, selected and tested as known in the art and as described in example 15 and using the analytical methods described in example 11.

EXAMPLE 17

Method for Assaying EPSPS Activity and Determination of Kinetic Constants. Method for Assaying EPSPS Activities in Crude Plant Materials and Discriminating the Proportion of the Total Which is Resistant to Glyphosate EPSPS Enzyme Assay Assays are carried out generally according to the radiochemical method of Padgette et al 1987 (Archives of Biochemistry and Biophysics, 258(2) 564–573) with K+ ions as the major species of cationic counterion. Assays in a total volume of 50 μl, in 50 mM Hepes(KOH) pH 7.0 at 25° C., contain purified enzyme or plant extract (see below) diluted appropriately in Hepes pH 7.0 containing 10% glycerol, and 5 mM DTT, $^{14}$C PEP either as variable substrate (for kinetic determinations) or fixed at 100 or 250 μM and shikimate 3 Phosphate (K+ salt) at 2 or 0.75 mM as indicated. Optionally, for assays of crude plant extracts, assays also contain 5 mM KF and/or 0.1 mM ammonium molybdate. Assays are started with the addition of $^{14}$C phosphoenolpyruvate (cyclohexylammonium+salt) and stopped after 2–10 minutes (2 minutes is preferable) with the addition of 50 μl of a solution of 1 part 1M acetic acid and 9 parts ethanol. After stopping, 20 μl is loaded onto a synchropak Ax100 (25 cm×4.6 mm) column and chromatographed using isocratic elution with a 0.28M potassium phosphate pH 6.5 mobile phase flowing at 0.5 ml/min over 35 minutes. Under these conditions the retention times for PEP and EPSP are ~19 and 25 minutes respectively. A CP 525TR scintillation counter is connected to the end of the Ax100 column. It is fitted with a 0.5 ml flow cell, and the flow rate of scintillant (Ultima Flo AP) is set at 1 ml/min. Relative peak areas of PEP and EPSP are integrated to determine the percentage conversion of labelled PEP to EPSP. Apparent $K_m$ and Vmax values are determined by least squares fit to a hyperbola with simple weighting using the Grafit 3.09b from Erithacus Software Ltd. Km values are generally ascertained using 8–9 concentrations of variable substrate ranging from $K_m/2$–10 $K_m$ and triplicate points. Except where specifically noted, data points are only included in the analysis where there is <30% conversion of substrate to EPSP.

Shikimate-3-Pi (S3P) is prepared as follows, To 7 mls of 0.3M TAPS pH 8.5 containing 0.05M Shikimate, 0.0665M ATP (Na salt), 10 mM KF, 5 mM DTT, and 0.05M $MgCl_2.6H_2O$, 75 μl of a 77 unit (μmol min$^{-1}$) ml$^{-1}$ solution of shikimate kinase is added. After 24 hrs at room temperature, the reaction is stopped by brief heating to 95° C. The reaction solution is diluted 50 fold in 0.01M Tris HCl pH 9, and chromatographed by anion exchange on Dowex 1×8–400, using a 0–0.34M $LiCl_2$ gradient. The S3P fractions are combined, freeze dried, and then redissolved in 7 mls distilled $H_2O$. 28 mls of 0.1M $Ba(CH_3COOH)_2$ and 189 mls of absolute ethanol are then added. This solution is left to stir overnight at 4° C. The resulting precipitate of tri-Barium S3P is collected and washed in 30 mls of 67% ethanol. The washed precipitate is then dissolved in ~30 mls distilled $H_2O$. By adding either $K_2SO_4$ the $K^+$ or $TMA^+$ salt of S3P is produced as required. Great care is taken to add a minimal excess of sulphate. The $BaSO_4$ precipitate is removed and the supernatant containing the required salt of S3P freeze dried. Each salt is weighed and analysed by proton NMR. S3P preparations so-prepared are >90% pure according to proton NMR and (according to their weights and integration of 31P NMR) contain only low residues of potassium sulphate.

Preparation of Extracts of Plant Material Suitable for EPSPS Assay

Callus or plantlet material (0.5–1.0 g) is ground to a fine frozen powder in a liquid nitrogen-chilled mortar and pestle. This powder is taken up in an equal volume of a suitable chilled extraction buffer (for example, 50 mM Hepes/KOH buffer at pH 7.5 containing 1 mM EDTA, 3 mM DTT, 1.7 mM 'pefabloc' (serine protease inhibitor), 1.5 mM leupeptin, 1.5 mM pepstatin A, 10% v/v glycerol and 1% polyvinylpyrolidone), resuspended, mixed and centrifuged in a chilled centrifuge to bring down debris. The supernatant is exchanged down a chilled PD10 column of Sephadex G25 into 25 mM Hepes/KOH buffer at pH 7.5 containing 1 mM EDTA, 3 mM DTT and 10% v/v glycerol. Protein is estimated by the Bradford method standardised using bovine serum albumen. A portion of the extract is frozen in liquid nitrogen; a portion is assayed immediately.

EPSPS assays of plant extracts are standardly carried out, as described above, with 0.1 mM $^{14}$C-PEP and 0.75 mM shikimate-3-Pi either in the absence or the presence of 0.1 mM N-(phosphonomethyl)glycine. Under these assay conditions, the resistant form of EPSPS (see below) is estimated to be inhibited by <8.5% whilst the sensitive w/t form is essentially fully inhibited (>98%). Thus, the level of activity observed in the presence of glyphosate (A) is taken to represent ~92% of the level of resistant enzyme derived from expression of the transgene whilst the level of susceptible w/t EPSPS is taken to be the total level of EPSPS activity observed in the absence of glyphosate minus the value of A×~1.08. Because the Vmax of the mutant enzyme is estimated to be only about a third of the Vmax of the w/t enzyme (and because the Km values for PEP of both w/t and mutant forms are estimated to be about 20 μM or less), the level of expression of the mutant enzyme polypeptide relative to the level of expression of the endogenous w/t EPSPS is taken to be about three fold higher than the ratio calculated on the basis of the ratio of their relative observed activities. The total level of EPSPS polypeptide expression (mutant+ w/t) is also estimated by using Westerns (see below).

EXAMPLE 18

Cloning and Expression of w/t and Mutated cDNA Encoding Mature Rice EPSPS in E.coli. Purification and Characterisation of w/t and Mutant Rice EPSPS Expression, Purification and Characterisation of w/t Mature Rice EPSPS Rice EPSPS cDNA is amplified using RT-PCR from RNA isolated from rice variety Koshigari using Superscript RT from BRL according to the recommendation supplied by the manufacturer. PCR is performed using Pfu turbo polymerase from Stratagene according to the methods supplied by the manufacturer. The oligonucleotides below are used in the amplification reaction and the reverse transcription steps.

```
SEQ. ID. NO.33
Rice 3' oligo
GCGCTCGAGTCAGTTCCTGACGAAAGTGCTTAGAACGTCG

SEQ. ID. NO.34
Rice 5' oligo
GCGCATATGAAGGCGGAGGAGATCGTGC
```

The PCR product is cloned into pCRBlunt II using Invitrogens Zero Blunt TOPO kit. The sequence of the insert is confirmed by sequencing and it is verified that the predicted open reading frame corresponds to that of the predicted mature chloroplastic rice EPSPS protein with the exception of the presence of an initiating Met. The cloned and verified rice epsps sequence is excised using Nde 1 and Xho 1 and the purified fragment is cloned into pET24a (Novagen) digested similarly. The recombinant clones are introduced into BL21 (DE3) a codon-optimised RP strain of *E. coli* supplied by Stratagene. The EPSPS protein is expressed in this strain following addition of 1 mM IPTG to the fermenter medium (LB supplemented with 100 ug/ml Kanamycin). The recombinant protein of the correct predicted mass is identified i) on the basis of Coomassie staining of SDS gels of cell extracts and side by side comparison with Coomassie-stained gels of extracts of similar *E. coli* cells transformed with an empty pET24a vector and ii) by western analysis using a polyclonal antibody raised to previously-purified plant EPSPS protein. The mature rice EPSPS protein is purified at ~4 C. as follows. 25 g wet weight of cells are washed in 50 ml of 0.1M Hepes/KOH buffer at pH 7.5 containing 5 mM DTT, 2 mM EDTA and 20% v/v glycerol. Following low-speed centrifugation, the cell pellet is resuspended in 50 ml of the same buffer but also containing 2 mM of 'Pefabloc' a serine protease inhibitor. Cells are evenly suspended using a glass homogenizer and then disrupted at 10000 psi using a Constant Systems (Budbrooke Rd, Warwick, U.K.) Basic Z cell disrupter. The crude extract is centrifuged at ~30,000 g for 1 h and the pellet discarded. Protamine sulphate (salmine) is added to a final concentration of 0.2%, mixed and the solution left to stand for 30 min. Precipitated material is removed by centrifugation for 30 min at ~30,000 g. Aristar grade ammonium sulfate is added to a final concentration of 40% of saturation, stirred for 30 min and then centrifuged at ~27,000 g for 30 min. The pellet is resuspended in ~10 ml of the same buffer as used for cell disruption, further ammonium sulfate is added to bring the solution to ~70% of saturation, the solution is stirred for 30 min and centrifuged again to yield a pellet which is resuspended in ~15 ml of S200 buffer (10 mM Hepes/KOH (pH 7.8) containing 1 mM DTT, 1 mM EDTA and 20% v/v glycerol). This is filtered (0.45 micron) loaded and chromatographed down a K26/60 column containing Superdex 200 equilibrated with S200 buffer. EPSPS-containing fractions detected on the basis of EPSPS enzyme activity are combined and loaded onto an xk16 column containing 20 ml of HP Q-Sepharose equilibrated with S200 buffer. The column is washed with S200 buffer and then EPSPS eluted within a linear gradient developed from 0.0M to 0.2M KCl in the same buffer. EPSPS elutes within a single peak corresponding to a salt concentration at or below 0.1 M. EPSPS-containing fractions detected on the basis of EPSPS enzyme activity are combined and loaded onto a HiLoad xk26/60 column of Superdex 75 equilibrated with Superdex 75 buffer (25 mM Hepes/KOH (pH 7.5) containing 2 mM DTT, 1 mM EDTA and 10% v/v glycerol). EPSPS elutes later from the column that might be expected on the basis of the molecular weight of the presumed dimer. This may be due to interaction of the protein with the gel matrix at low ionic strength. EPSPS-containing fractions identified on the basis of enzyme activity are combined and loaded onto a 1 ml column of MonoQ equilibrated with the same, Superdex 75 buffer. The column is washed with starting buffer and EPSPS eluted as a single peak over the course of a 15 ml linear gradient developed between 0.0 and 0.2M KCl. EPSPS is obtained near (>90% pure) at this stage in the purification. Optionally, EPSPS is further purified by exchange into Superdex 75 buffer containing 1.0 M (Aristar) ammonium sulphate and loading onto a 10 ml column of phenyl sepharose equilibrated in the same buffer. EPSPS is eluted as a single peak early during the course of a linear gradient of declining ammonium sulphate developed between 1.0 and 0.0 M ammonium sulphate.

Cloning, Expression, Purification and Characterisation of Glyphosate-resistant Mutant Rice EPSPS The rice EPSPS cDNA in pCRBlunt is used as a template for two further PCR using the following primer pairs designed to introduce specific changes

```
SEQ. ID. NO. 35
Rice 5'oligo                    GCGCATATGAAGGCGGAGGAGATCGTGC SEQ. ID. NO. 36
Rice mutant reverse to RV  GCAGTCACGGCTGCTGTCAATGATCGCATTGCAATTCCAGCGTTCC SEQ. ID. NO. 37
Rice 3'oligo                    GCGCTCGAGTCAGTTCCTGACGAAAGTGCTTAGAACGTCG SEQ. ID. NO.38
Rice mutant forward to sal GGAACGCTGGAATTGCAATGCGATCATTGACAGCAGCCGTGACTGC
```

The resultant products are gel purified and placed into a tube in eqi-molar concentrations to serve as a template for another round of PCRs with the rice 5' and 3' oligos. The resultant products are cloned into pCRBlunt II using Invitrogens Zero Blunt TOPO kit. It is confirmed that the DNA sequence of the insert and its predicted open reading frame correspond to that of the predicted mature chloroplastic rice EPSPS protein (with the exception of the presence of an initiating Met) and also that the desired changes (the specific mutation of T to I and P to S at specific positions in the EPSPS sequence) are encoded. The thus cloned and verified rice epsps sequence is excised using Nde 1 and Xho 1 and the purified fragment cloned into pET24a (Novagen) digested similarly. The recombinant clones are introduced into BL21 (DE3), a codon optimised RP strain of E. coli supplied by Stratagene. The EPSPS protein is expressed in this strain following addition of 1 mM IPTG to the fermenter medium (LB supplemented with 100 ug/ml Kanamycin). The recombinant protein of the correct predicted mass is identified i) on the basis of Coomassie staining of SDS gels of cell extracts and side by side comparison with Coomassie-stained gels of extracts of similar E.coli cells transformed with an empty pET24a vector and ii) by western analysis using a polyclonal antibody raised to previously-purified plant EPSPS protein. This mutant form of rice EPSPS is purified and characterised in a similar manner to the method described above for w/t rice EPSPS.

The so-obtained mutant form of rice EPSPS, assayed as described above in the presence of 2 mM shikimate-3-Pi, has an apparent Vmax of ~10 μmol/min/mg and a Km for PEP of 22 μM. At 40 μM PEP, the IC50 value for the potassium salt of glyphosate is ~0.6 mM. The estimated Ki value for potassium glyphosate of the mutant EPSPS is ~0.2 mM.

EXAMPLE 19

Preparation of Antibodies to Purified Rice EPSPS and Methods for Western Analysis Standard methods for generation of polyclonal antisera in rabbits are used. Rabbits are young female New Zealand Whites. Immunisation courses consist of 4 doses, each ~100 mg, administered at monthly intervals. Each dose in phosphate buffered saline is administered as an emulsion with Freund's Complete adjuvant (dose 1) or Incomplete adjuvant (doses 2–4) and is injected at four sub-cutaneous sites. A pre-bleed is taken before dose 1 is administered. A test bleed is taken 14 days after the second dose to confirm the immune response. A term bleed is taken 14 days after the fourth dose and used for experimentation. A fifth and final dose is given when at least 6 weeks has elapsed since the fourth dose, and the final bleed (also used for experimentation) is taken 14 days later. Antibodies are raised to both (i) purified native mature wit rice EPSPS (example 8) and also (ii) to SDS-denatured rice EPSPS polypeptide which is eluted from a band cut out of a 12% SDS gel (the correct position of the protein being accurately marked by side by side Coomassie staining of the band).

12% polyacrylamide gels are used for SDS gel electrophoresis and Western blotting. Electrophoresis is performed at a constant current of 100V for 90 minutes. Gels are blotted against nitrocellulose sheets overnight at 4 C. at a constant 30V. Sheets are blocked in 5% Marvel phosphate buffered saline containing 0.1% Tween (PBS-tween) for 1 or 2 hours, washed three times in PBS-tween and incubated in rice EPSPS-Rb1 primary antibody at ~1.3 mg IgG/ml (normally equivalent to a 1:4000 to 1:20,000 dilution of term bleed). These antibody dilutions are applied in PBS (phosphate-buffered saline) containing 1% Marvel and 0.05% Tween 20 for 2 hours. Secondary antibody, Goat anti Rabbit HRP (Sigma A6154) is applied at 1:10,000 or 1:20,000 in PBS containing 0.05% Tween and 1% Marvel. Incubation with secondary antibody is continued for 1 hour, the blott is washed three times in PBS (0.05% tween), ECL substrate is applied for usually 1 minute and film exposed for 10–60 seconds. Negative control blots are blots with (1) preimmune serum at a dilution calculated to yield the same [IgG] as in test immune sera (IgG is routinely purified from an aliquot of each serum and quantitated so that these dilutions can be calculated directly) and also (2) immune serum raised against Freund's adjuvant alone. IgG concentration in control immune sera is adjusted so that controls are at an appropriate concentration of IgG. In order to make this calculation, IgG is purified from crude antiserum by filtration through a 0.45 μm syringe filter and passed down a 1 ml HiTrap protein G column (Pharmacia cat no: 17-0404-01). The bound IgG is eluted from the column with 0.1M glycine HCl pH 2.9 and dialysed vs PBS overnight. The IgG concentration is estimated by UV determination. (a 1 cm pathlength of a 1 mg $ml^{-1}$ solution of pure IgG has an absorbance at 280 nm wavelength of 1.35). From the IgG yield a calculation can be made of IgG concentration in the crude antiserum, and correct dilutions in western blots calculated accordingly.

Plant tissue samples are prepared for example as described in example 17. Alternatively, for Western analysis, a much simpler procedure is used. 100–200 mg of plant tissue to be analysed is rapidly homogenized (for example using an ultra turrax, bead beater or glass homogenizer) in an equal volume of buffer (similar to in example 7), centrifuged for 5 minutes in a chilled eppendorf microcentrifuge and the supernatant a) a small aliquot is analysed for protein using the Bradford method and b) for the most part mixed 1:1 with Laemli SDS 'sample buffer', heated and then stored ready for loading onto gels. Typically SDS slab gels are loaded with 10 protein samples in 10 wells. Typically these are 1 to 10 μg of crude extracts of plant material for analysis alongside a standard curve of between 0 and 20 ng of pure rice EPSPS. In some cases Westerns are run using antibodies raised to purified w/t EPSPS from *Brassica napus* (expressed and purified using similar methods to those described above). In this case the strength of the cross reaction of the antibodies is less strong with rice EPSPS (or with endogenous plant wheat or maize EPSPS) than in the case that antibodies raised to rice EPSPS be used but still, nevertheless, provide sufficient reaction for useful quantitative information in relation to the standard curve to be derivable.

EXAMPLE 20

Isolation of Genomic DNA from Transgenic Plant Material. PCR Analysis. DNA Probe Preparation and Hybiridisation. Copy Number and Integrity of Transgene Genomic DNA is isolated from plants, plantlets and callus material using, for example, the method of Dellporta et al (1983) in Chromosome Structure and Function: Impact of New Concepts, 18'th Stadler Genetics Symposium. J. P. Gustafson and R. Appels, eds). New York: Plenum Press) pp 263–282 or, alternatively, using a DNAeasy kit (Qiagen).

Transgenic callus and plant segregants that contain the mutated rice EPSPS transgene are identified using fluoresence PCR using oligonucleotide primers SEQ. ID NO. 39 and 40 that are specific to the mutations within the rice EPSPS genomic sequence. The fluorescent dye SYBR green, which intercalates with double stranded DNA, is included in the PCR so that samples containing the mutated rice EPSPS gene are identified by an increase in fluoresence in the sample, which is detected using an ABI 3377 machine. Alternatively, those skilled in the art will know that the primers may be fluorescently labelled and technologies such as molecular beacons and 'Scorpions' are available.

```
SEQ. ID NO.39
RiceDM Fwd2-3A
5'- gtg gaa cgc tgg aat tgc aat gca at -3'

SEQ. ID. NO.40
Universal Reverse
5'- gtt gca ttt cca gca gca gca gt -3'
```

A typical PCR reaction consists of, prepared in 96 well Optical plates and sealed with Optical lids (PE Biosystems), is as follows:
5.0 μl gDNA template, (Qiagen DNeasy prep)
12.5 μl 2× SYBR Green premix
2.5 μl 5 pmol/μl Stock Forward Primer
2.5 μl 5 pmol/μl Stock Reverse Primer
2.5 μl ddH2O
25.0 μl Total volume
The following cycling parameters are followed:

| Stage 1: | 50° C. × 2 mins | |
|---|---|---|
| Stage 2: | 95° C. × 10 mins | |
| Stage 3: | 50 cycles of | 95° C. × 15 secs |
| | 60° C. × 45 secs | |

Changes in fluorescence within the samples is recorded every seven seconds from stage 3 of the reaction.

For Southern blotting approximately 10 μg of DNA is used for each restriction digest. Genomic DNA is digested with suitable restriction enzymes (e.g Hind III) according to the manufacturer's instructions (e.g Promega). Restriction enzymes are chosen that cut both within and outside the mutant EPSPS sequence. DNA is separated using TAE (0.04M tris-acetate, 1 mM EDTA) 0.8% agarose gels. Southern blotting is carried out according to methods giving by Sambrook et al., 1989 using HyBond N+ nitrocellulose blotting membrane (AmershamPharmacia). The DNA is cross-linked to the membrane by exposure to UV illumination.

DNA fragments used for generating specific probes are isolated by purification on gels of restriction digests of plasmid DNA or generated by PCR. For example, a 700 bp fragment containing intron 1 of the rice EPSPS gene, is generated by PCR using primers as shown below.

```
SEQ. ID. NO.41
INT1/5 5' cccttcctcttgcgtgaattccatttc 3'

SEQ. ID. NO.42
INT1/3 5' gttgtcccctaataaccagag 3'
```

Such probes are labelled with $^{32}$P using the random priming method, for example Ready-To-Go DNA labelling beads (AmershamPharmacia) and purified using, for example, MicroSpin G-25 columns (AmershamPharmacia).

Blots of DNA gels are prehybridized at 65 C. in 5×SSC, 0.5% SDS, 2×Denhardt's solution, 0.15 mg/ml denatured salmon sperm DNA for at least one hour. The blot is then hybridized with denatured probe for 16–24 h at 65 C. in fresh pre-hybridisation solution. Membranes are blotted dry and visualised using autoradiography.

Where Southern blotting indicates a single integration event of the transgene at a single locus, indicted by the probe hybridising with only a single specific sized restriction fragment, then the result is confirmed through a rehyridisation of the blot using an alternative probe. For controls, untransformed material is used. Additionally the blot may be probed further with hybridisation probes specific to other regions of the transgenic construct (for example the promoter, 5'UTR intron or upstream enhancer sequences) in order to verify the integrity of the construct. Additionally, in the case that *Agrobacterium* transformation is used, specific probes are used to indicate the presence or absence of any DNA extending from beyond the RB and LB of the superbinary vector.

What is claimed is:

1. An isolated polynucleotide comprising the following components in the 5' to 3' direction of transcription:
   (i) at least one transcriptional enhancer sequence, selected from the group consisting of SEQ ID NOS 45, 46, 47, 48, 49, 50, and 51;
   (ii) a sequence selected from the group consisting of SEQ ID NOS 52, 53, and 54, which comprises the promoter from the rice EPSPS gene;
   (iii) the rice genomic sequence which encodes the rice EPSPS chloroplast transit peptide and encodes the rice EPSPS enzyme of SEQ ID NO 43; and
   (iv) a transcriptional terminator sequence;
   wherein the rice EPSPS coding sequence is modified in that a first position is mutated so that the residue at this position is Ile rather than Thr and a second position is mutated so that the residue at this position is Ser rather than Pro, the mutations being introduced into EPSPS sequences which comprise the following conserved region GNAGTAMRPLTAAV (SEQ ID NO 56) in the wild type enzyme (SEQ ID NO 43) such that modified sequence (SEQ ID NO 44) reads GNAGIAMRSLTAAV (SEQ ID NO 57).

2. The polynucleotide according to claim 1, which comprises two transcriptional enhancers selected from the group consisting of the enhancers depicted in SEQ ID Nos 45, 46, 47, 48, 49, 50, and 51.

3. The polynucleotide according to claim 2, in which the transcriptional enhancers are tandemly present in the polynucleotide.

4. The polynucleotide according to claim 1, wherein the 3' end of the enhancer is between about 100 to about 1000 nucleotides upstream of the codon corresponding to the translational start of the EPSPS transit peptide.

5. The polynucleotide according to claim 2, wherein the 3' end of the first enhancer is between about 100 to about 1000 nucleotides upstream of the codon corresponding to the translational start of the EPSPS transit peptide.

6. The polynucleotide according to claim 1, further comprising an intron, and wherein the 3' end of the enhancer is between about 100 to about 1000 nucleotides upstream of the first nucleotide of the intron in the untranslated region.

7. The polynucleotide of claim 6 wherein the intron has the sequence depicted in SEQ ID NO 55.

8. The polynucleotide according to claim 1, wherein the 3' end of the enhancer is between about 300 to about 950 nucleotides upstream of the codon corresponding to the translational start of the EPSPS transit peptide.

9. The polynucleotide according to claim 2, wherein the 3' end of the first enhancer is between about 300 to about 950 nucleotides upstream of the codon corresponding to the translational start of the EPSPS transit peptide.

10. The polynucleotide according to claim 1, further comprising an intron, and wherein the 3' end of the enhancer is between about 300 to about 950 nucleotides upstream of the first nucleotide of the intron in the untranslated region.

11. The polynucleotide of claim 10 wherein the intron has the sequence depicted in SEQ ID NO 55.

12. The polynucleotide according to claim 1, wherein the 3' end of the enhancer is between about 770 to about 790 nucleotides upstream of the codon corresponding to the translational start of the EPSPS transit peptide.

13. The polynucleotide according to claim 2, wherein the 3' end of the first enhancer is between about 770 to about 790 nucleotides upstream of the codon corresponding to the translational start of the EPSPS transit peptide.

14. The polynucleotide according to claim 1, further comprising an intron, and wherein the 3' end of the enhancer is between about 770 to about 790 nucleotides upstream of the first nucleotide of the intron in the untranslated region.

15. The polynucleotide of claim 14 wherein the intron has the sequence depicted in SEQ ID NO 55.

16. The polynucleotide according to claim 1, wherein the 3' end of the enhancer is between about 300 to about 380 nucleotides upstream of the codon corresponding to the translational start of the EPSPS transit peptide.

17. The polynucleotide according to claim 2, wherein the 3' end of the first enhancer is between about 300 to about 380 nucleotides upstream of the codon corresponding to the translational start of the EPSPS transit peptide.

18. The polynucleotide according to claim 1, further comprising an intron, and wherein the 3' end of the enhancer is between about 300 to about 380 nucleotides upstream of the first nucleotide of the intron in the untranslated region.

19. The polynucleotide of claim 18 wherin the intron has the sequence depicted in SEQ ID NO 55.

20. The polynucleotide according to claim 1, wherein the 3' end of the enhancer is between about 320 to about 350 nucleotides upstream of the codon corresponding to the translational start of the EPSPS transit peptide.

21. The polynucleotide according to claim 2, wherein the 3' end of the first enhancer is between about 320 to about 350 nucleotides upstream of the codon corresponding to the translational start of the EPSPS transit peptide.

22. The polynucleotide according to claim 1, further comprising an intron, and wherein the 3' end of the enhancer is between about 320 to about 350 nucleotides upstream of the first nucleotide of the intron in the untranslated region.

23. The polynucleotide of claim 22 wherein the intron has the sequence depicted in SEQ ID NO 55.

24. The polynucleotide according to claim 1, wherein the enhancer has the sequence depicted in SEQ ID NO. 45 or 46.

25. The polynucleotide according to claim 2, wherein in a 5' to 3' direction the first enhancer has the sequence depicted in SEQ ID NO 50 and the second enhancer has the sequence depicted in SEQ ID Nos 45 or 46.

26. The polynucleotide according to claim 2, wherein in a 5' to 3' direction the first enhancer has the sequence depicted in SEQ ID NO 49 and the second enhancer has the sequence depicted in SEQ ID Nos 45 or 46.

27. The polynucleotide according to claim 2, wherein in a 5' to 3' direction the first enhancer has the sequence depicted in SEQ ID NO 51 and the second enhancer has the sequence depicted in SEQ ID Nos 45 or 46.

28. The polynucleotide according to claim 2, wherein in a 5' to 3' direction the first enhancer has the sequence depicted in SEQ ID NO 48 and the second enhancer has the sequence depicted in SEQ ID Nos 45 or 46.

29. The polynucleotide according to claim 2, wherein in a 5' to 3' direction the first enhancer has the sequence depicted in SEQ ID NO 45 and the second enhancer has the sequence depicted in SEQ ID Nos 45 or 46.

30. The polynucleotide according to claim 1, which further comprises a sequence which encodes a protein which confers upon plant material transformed with the polynucleotide at least one of the following traits, resistance to insects, fungi, viruses, bacteria, nematodes, stress, desiccation or herbicides.

31. The polynucleotide according to claim 30, wherein the insect resistance protein is selected from the group consisting of cryIAc, cryIAb, cry3A, Vip 1A, Vip 1B, a cystein protease inhibitor and snow drop lectin; the fungus resistance protein is selected from the group consisting of a defensin, a chitinase, a glucanase and Avr-Cf9; the virus resistance protein is selected from the group consisting of a cecropin and a techyplesin, and the virus resistance protein is selected from the group consisting of a viral coat protein, a movement protein and a viral replicase.

* * * * *